United States Patent
Ervin, Jr.

(10) Patent No.: US 6,939,714 B2
(45) Date of Patent: Sep. 6, 2005

(54) EPITHELIAL CELL GROWTH INHIBITORS

(75) Inventor: Paul R. Ervin, Jr., Ann Arbor, MI (US)

(73) Assignee: Biotherapies, Inc., Ann Arbor, MI (US)

( * ) Notice: Subject to any disclaimer, the term of this patent is extended or adjusted under 35 U.S.C. 154(b) by 181 days.

(21) Appl. No.: 10/028,952

(22) Filed: Dec. 18, 2001

(65) Prior Publication Data

US 2003/0157576 A1 Aug. 21, 2003

Related U.S. Application Data

(63) Continuation of application No. PCT/US00/16900, filed on Jun. 19, 2000.
(60) Provisional application No. 60/139,995, filed on Jun. 18, 1999.

(51) Int. Cl.⁷ .................... G01N 33/48; G01N 33/574; A61K 49/00
(52) U.S. Cl. .................. 436/64; 424/9.1; 435/7.23
(58) Field of Search ................. 436/64; 424/9.1; 435/7.23, 7.92

(56) References Cited

FOREIGN PATENT DOCUMENTS

| WO | WO 96/31625 | 10/1996 |
| WO | WO 98/14577 | 4/1998 |
| WO | WO 99/32625 | 7/1999 |

OTHER PUBLICATIONS

Wiersma et al. (Eur J. Immunol. 1991, vol. 21. No. 10, abstract).*

Ervin, P. et al., "Identification of a Prostate Analog to the Growth Inhibitor Mammastatin", *Proceedings of the 91st Annual Meeting of the American Association for Cancer Research*, p. 251 (Mar. 2000).

* cited by examiner

*Primary Examiner*—Gary B. Nickol
(74) *Attorney, Agent, or Firm*—Merchant & Gould PC

(57) ABSTRACT

Epithelial cell growth inhibitors differentially express in normal and cancerous epithelial cells. The ECGI proteins and nucleic acid sequence encoding them are useful in the diagnosis and treatment of epithelial cell cancers, for example prostate, ovarian, colon cancer, and the like.

6 Claims, 10 Drawing Sheets

FIG. 1
Template mRNA
A. 100 bp ladder
B. Colon
C. Ovary
D. Prostate
E. Spleen
F. Testis
G. Thymus
H. NHMC
I. Control
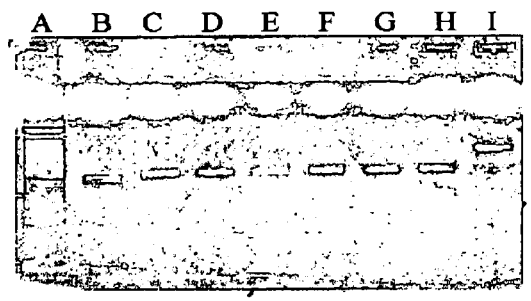
Negative Image
A. 100 bp ladder
B. Colon
C. Ovary
D. Prostate
E. Spleen
F. Testis
G. Thymus
H. NHMC
I. Control
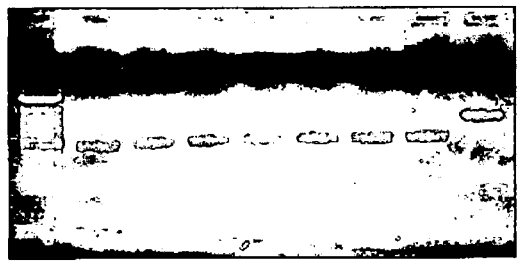
Positive Image

FIG. 1 A

| 1 | 2 | 3 | 4 | 5 | 6 | 7 | 8 | 9 | 10 | 11 | 12 |
|---|---|---|---|---|---|---|---|---|---|---|---|
| whole brain | cerebellum, left | substantia nigra | heart | esophagus | colon, transverse | kidney | lung | liver | leukemia, HL-60 | fetal brain | yeast total RNA |
| cerebral cortex | cerebellum, right | accumbens nucleus | aorta | stomach | colon, desending | skeletal muscle | placenta | pancreas | HeLa S3 | fetal heart | yeast tRNA |
| frontal lobe | corpus callosum | thalamus | atrium, left | duodenum | rectum | spleen | bladder | adrenal gland | leukemia, K-562 | fetal kidney | E. coli rRNA |
| parietal lobe | amygdala | pituitary gland | atrium, right | jejunum | | thymus | uterus | thyroid gland | leukemia, MOLT-4 | fetal liver | E. coli DNA |
| occipital lobe | caudate nucleus | spinal cord | ventricle, left | ileum | | peripheral blood leukocyte | prostate | salivary gland | Burkitt's lymphoma, Raji | fetal spleen | Poly r(A) |
| temporal lobe | hippo-campus | | ventricle, right | ilecocum | | lymph node | testis | mammary gland | Burkitt's lymphoma, Daudi | fetal thymus | human Cot -1 DNA |
| p. g.* of cerebral cortex | medulla oblongata | | inter-ventricular septum | appendix | | bone marrow | ovary | | colorectal adeno-carcinoma, SW480 | total lung | human DNA 100 ng |
| pons | putamen | | apex of the heart | colon, ascending | | trachea | | | lung carcinoma, A549 | | human DNA 500 ng |

* paracentral gyrus urchaser
Is intended to be used for research purposes only. It is not to be used for drug or diagnostic purposes nor is it intended for products may not be resold, modified for resale, or used to manufacture commercial products without written approval of C ONTECH Laboratories, Inc.

INTERNET: www.clontech.com                    CLONTECH Labor

| DNA Gel (Positive) Lane | 1 2 3 4 5 6 7 8 | |
|---|---|---|
| |  | Ethidium Bromide stain of plasmid DNA digested with ECO R1 and Xho1, separated on 1% agarose: 1) Molecular weight ladder, 2) Clone ccp2U-1, 3) Clone ccp2U-2, 4) Clone ccp2U-3, 5) Clone ccp2U-4, 6) Clone ccp2U-5, 7) Clone ccp2U-6, 8) Clone ccp2U-7. |
| Nitrocellulose Membrane | 1 2 3 4 5 6 7 8 9 10 | |
| Putative Prostastatin |  | Southern Blot of plasmid DNA digested with ECO R1 and Xho1, separated on 1% agarose transferred to nitrocellulose and hybridized to digoxin labeled 2U PCR product: 1) Molecular weight ladder, 2) Clone ccp2U-1, 3) Clone ccp2U-2, 4) Clone ccp2U-3, 5) Clone ccp2U-4, 6) Clone ccp2U-5, 7) Clone ccp2U-6, 8) Clone ccp2U-7, 9) Clone ccp2U-8, 10) Clone ccp2U-9 |

Mammastatin and Related Gene Structure

EPITHELIAL CELL GROWTH INHIBITORS

This application is a continuation of international application number PCT/US00/16900, filed Jun. 19, 2000, pending, which claims the benefit of U.S. Provisional Patent Application No. 60/139,995, filed Jun. 18, 1999, the disclosure of which is incorporated in its entirety.

FIELD OF THE INVENTION

This invention relates to a family of epithelial cell growth inhibitors useful in the diagnosis and treatment of epithelial cell cancers.

BACKGROUND OF THE INVENTION

Epithelial cell cancers, for example, prostate cancer, breast cancer, colon cancer, lung cancer, pancreatic cancer, ovarian cancer, cancer of the spleen, testicular cancer, cancer of the thymus, etc., are diseases characterized by abnormal, accelerated growth of epithelial cells. This accelerated growth initially causes a tumor to form. Eventually, metastasis to different organ sites can also occur. Although progress has been made in the diagnosis and treatment of various cancers, these diseases still result in significant mortality.

The treatment of cancer is greatly enhanced by early detection. However, there are difficulties in detecting the disease in its early stages. For example, epithelial tissue-containing organs such as the prostate, ovary, and others, are not easily palpated. The detection of abnormal tumor growth in such organs is difficult without frequent screening and appropriate markers. A substantial drawback of available cancer diagnostic assays is a high rate of false positive and negative results, making the available tests less reliable than desired. For this reason, there is a great need to identify new diagnostic as well as new therapeutic agents to improve diagnosis and treatment of cancer, for example, prostate cancer, breast cancer, colon cancer, lung cancer, pancreatic cancer, ovarian cancer, cancer of the spleen, testicular cancer, cancer of the thymus, etc., A novel, specific, mammary cell growth inhibitor, Mammastatin, has recently been identified and characterized. Mammastatin has been expressed from variant clones, MammA (PCT/US97/18026, ATCC# 97451, deposited 22 Feb. 1996); MammB (PCT/US97/27147, ATCC# PTA-2091, deposited 15 Jun. 2000); and MammC, described in copending PCT application No. PCT/US00/16933, filed on even date herewith (ATCC# PTA-2090, deposited 15 Jun. 2000).

Mammastatin is produced and secreted by normal mammary cells, and is detected in blood samples of normal individuals. Blood concentrations of the mammary cell growth inhibitor, and particularly of the active, phosphorylated form of Mammastatin, are reduced or absent in breast cancer patients. Administration of protein comprising active Mammastatin (secreted from normal human breast cancer cells) is effective to reduce tumor size and number, and to prevent tumor growth in late stage cancer patients.

Epithelial cell growth inhibitors having similarity to Mammastatin have now been discovered, isolated, and characterized. These inhibitors bear partial sequence identity to Mammastatin at the 5' end of the sequence, and have little or no identity at the 3' end of the molecule. Like Mammastatin, the newly discovered family of epithelial cell growth inhibitors (ECGI) are differentially expressed in normal epithelial cell tissues, but not in cancerous epithelial cell tissues. Also, like Mammastatin, the newly discovered family of epithelial cell growth inhibitors are detected in blood samples taken from normal individuals, but not in the blood of patients with epithelial cell cancers, as shown in the Examples below.

SUMMARY OF THE INVENTION

A family of epithelial cell growth inhibitors (ECGI) have now been identified in a number of different epithelial cells. These ECGI are differentially expressed in normal epithelial cells, but not in epithelial cancer cells. As shown in the Examples below, Mammastatin-like ECGI proteins have been discovered in a variety of epithelial cell tissues, including prostate, colon, ovary, lung, spleen, testis, thymus, and others.

The ECGI of the invention are expressed in normal epithelial cells but not in cancerous epithelial cells. The Mammastatin-like ECGI proteins are encoded by nucleic acid sequences that hybridize to nucleic acid sequences encoding Mammastatin. The ECGI proteins also bind anti-Mammastatin antibody. A nucleic acid sequence encoding ECGI in prostate cells (PRT-6, SEQ ID NO: 4) has been isolated and characterized (PRT-6, ATCC# PTA-2092, deposited 15 Jun. 2000), as described in the Examples below.

Because the ECGI of the invention are differently expressed by normal epithelial cells and not by cancerous epithelial cells, the presence or amount of the ECGI can be analyzed to diagnose cancer and/or to monitor treatment. The inventive ECGI proteins and nucleic acids encoding them also provide useful therapeutic agents to inhibit epithelial cell growth, prevent tumor formation, and treat cancer.

BRIEF DESCRIPTION OF THE FIGURES

FIG. 1A is a schematic diagram of an mRNA test panel showing locations of specific tissue mRNAs for analysis; FIG. 1B is a computer scanned image of a Northern blot showing hybridization of Mammastatin nucleic acid sequence to mRNA from a variety of tissues according to the plan shown in FIG. 1A.

FIG. 4 is a computer scanned image of a Western blot assay, showing cell lysates from normal prostate cells (A), LnCap prostate cancer cells (B), normal colon cells (C), and colon cancer cells (D) probed with anti-Mammastatin antibody, 7G6.

FIG. 7 is a computer scanned image of a DNA gel containing putative prostate ECGF DNA clones.

DETAILED DESCRIPTION OF THE INVENTION

Proteins of the Invention

Figure 1:
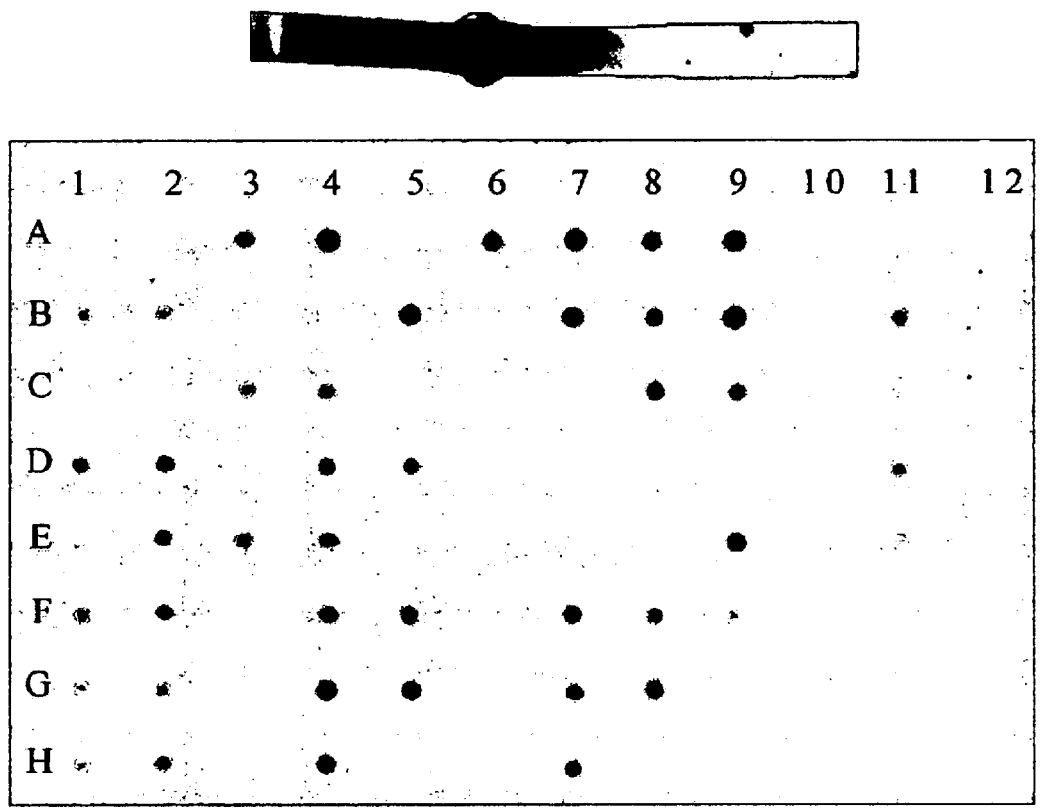
FIG. 1 shows hybridization of a nucleic said sequence encoding Mammastatin to RNA of specific tissues.

"Epithelial cell growth inhibitor (ECGI) proteins" of the invention are defined herein to mean Mammastatin-like proteins produced by and active to inhibit the growth of normal epithelial cells. Active, inhibitory ECGI proteins of the invention are reduced or absent in cancerous epithelial cells. The ECGI protein family disclosed herein appears to include inhibitors that are specific to each epithelial tissue, with little or no inhibitory activity across tissue types. As discussed more fully below, it is postulated that each ECGI protein contains a growth inhibitory domain and a tissue-specificity domain.

The ECGI proteins of the invention exhibit significant homology to Mammastatin, a mammary cell growth inhibitor produced by normal human mammary cells, and previously demonstrated be useful in the diagnosis and treatment of breast cancer (PCT/US97/18026). ECGI proteins bind one or more anti-Mammastatin antibodies such as 7G6 (Neomarkers, Freemont, Calif.), and are encoded by nucleic acid sequences sharing significant homology with nucleic acid sequences encoding Mammastatin.

Biological Deposits

Biological materials, including hybridomas and plasmids recited in the specification having ATCC Accession Numbers, were deposited with the American Type Culture Collection, 10801 University Blvd., Manassas, Va. 20110, under the provisions of the Budapest Treary.

Studies reported in the Examples below demonstrate the differential expression of ECGI proteins in normal epithelial cell tissues, but not in cancerous epithelial cell tissues, including breast, prostate, ovary, and colon. Like Mammastatin, the ECGI proteins of the invention appear, for example, in Western blots, as doublets or triplet bands, with one major band and one or two smaller, less prominent bands. This pattern of expression was demonstrated for Mammastatin to be due to phosphorylation of the protein. Mammastatin has an approximate molecular weight of 53 kilodaltons when phosphorylated at two sites. Smaller sized Mammastatin, 49 and 44 kilodaltons, correspond to one or none of the sites being phosphorylated. Phosphorylation of the Mammastatin protein is correlated with its inhibitory activity.

Western blots of ECGI probed with the anti-Mammastatin antibody 7G6, demonstrate the approximate size of ECGI produced by various epithelial cell tissues. As shown more fully in the Examples below (see, for example, FIGS. 4–5), ECGI from prostate cells migrates in a Western blot to approximately 55 kilodaltons, with less prominent, smaller bands at 51 and 46 kilodaltons suggestive of phosphorylated forms similar to the pattern seen for Mammastatin. ECGI from colon cells migrates to approximately 50 KD, with less prominent bands at approximately 47 and 43 kilodaltons. ECGI from ovarian cells migrates to approximately 60 kilodaltons.

Nucleic Acid Sequences Encoding ECGI

Nucleic acid sequences of the invention are defined herein as those nucleic acid sequences that encode ECGI proteins, as defined above. Nucleic acid sequences encoding ECGI proteins share significant sequence homology to nucleic acid sequences encoding Mammastatin, and hybridize to nucleic acid sequences encoding Mammastatin under conditions of high stringency.

Mammastatin-like epithelial cell growth inhibitors preferably have substantial identity (at least 90%, and preferably at least 95% identity) over approximately 1000 contiguous nucleotides of a nucleic acid sequence encoding Mammastatin. Nucleic acids encoding Mammastatin include those DNA inserts of MammA (PCT/US97/18026, ATCC# 97451, deposited 22 Feb. 1996); MammB (PCT/US97/27147, ATCC# PTA-2091, deposited 15 Jun. 2000); and MammC, described herein (ATCC# PTA-2092, deposited 15 Jun. 2000). Consensus sequences determined for known Mammmastatin clones are shown in the Comparative Sequence Table 5 below, and as SEQ ID NO: 1 (MammA); SEQ ID NO: 2 (MammB); SEQ ID NO: 3 (MammC). Prostate ECGI nucleic acid sequence (SEQ ID NO: 4) is shown in Tables 1, 2, and 5.

ECGI can be amplified from a specific epithelial cell nucleic acid library, for example, using internal Mammastatin primers and/or by hybridization to Mammastatin under conditions of strict stringency. As shown more fully in the Examples below, nucleic acid sequences hybridizing to Mammastatin have been demonstrated in numerous epithelial tissues, including central nervous system, heart, small intestine, large intestine, appendix, rectum, lymphatic cells, bone marrow cells, lung and air passages, bladder, uterus, prostate, testis, ovary, liver, pancreas, adrenal gland, salivary gland, and mammary gland (See FIG. 1).

The nucleic acid sequence of a ECGI isolated from prostate cells, for example, shares greater than 95% identity to Mammastatin at the 5' half of the molecule, with little or no identity of sequence, however, at the 3' half. It is postulated that the 5' end, sharing identity with Mammastatin, includes a growth inhibitory domain of the molecule, whereas the 3' end, having little identity to Mammastatin, includes a tissue-specificity domain.

Diagnostic Methods

The invention further provides an in vitro assay for detecting active, inhibitory ECGI in patient samples, including tissues, cells, and fluids. Epithelial cell cancer and advancing metastatic disease is diagnosed by correlating the presence and type of ECGI protein in a patient's sample with that of normal or cancerous human epithelial cells. A patient's blood or tissue sample is analyzed for the ECGI protein, e.g., for the abundance of the ECGI protein and/or for its molecular weight forms. As discussed below, the absence or loss of ECGI protein, particularly of the higher molecular weight, phosphorylated forms, is correlated with a specific epithelial cell indicative of advancing metastatic disease.

Analysis of ECGI can be performed using a variety of known analytical tools and methods, including immunoassays, hybridization, PCR techniques, and the like. Preferred are immunoassay, including ELISA, Western Blot, and dot-blot analysis of a patient's sample methods, using anti-ECGI antibodies. Preferably, recombinant ECGI standards are used to provide a standard curve for reliable quantitation of inhibitor levels. Such immunoassays are exemplified by the dot-blot assays and Western blot assays shown in the examples below. In an alternative preferred embodiment of the invention, tissue samples, such as tumor biopsies, are analyzed by immunohistochemistry, or by culturing a patient's tumor cells and examining the cultures for expression of ECGI.

In a particularly preferred embodiment, an assay for the diagnosis of an epithelial cell cancer includes at least two specific antibodies: an antibody to identify the sampled tissue as epithelial tissue, such as an anti-cytokeratin antibody, and a specific anti-ECGI antibody. For example, using an immunoblot format, prostate tissue suspected of containing the prostate cancer cells is homogenized, separated on an SDS/PAGE gel, transferred to membrane, and probed with both anti-keratin and anti-prostate ECGI antibodies. Isotype specific second antibodies that are conjugated to a suitable marker system such as peroxidase or alkaline phosphates are used to detect bound antibodies. Membranes containing bound first and second antibodies are then developed using known colormetric or fluorometric techniques and quantitated by known methods.

In the most preferred embodiment, the sample is analyzed for the size and/or phosphorylated forms of the ECGI, such as by Western Blot, using anti-ECGI antibodies. A decline or absence of the high molecular weight ECGI protein form correlates with advancing cancer.

Diagnostic kits of the invention include ECGI protein or nucleic acid sequences encoding ECGI, for example, as controls. Optionally, the diagnostic kit contains one or more antibodies that bind the epithelial cell ECGI to be detected or quantified. The antibodies may bind a Mammastatin-like domain (for example, 7G6), or may be tissue-specific ECGI antibodies. Alternatively, the diagnostic kit includes one or more amplification primer or hybridization probe for the amplification and/or detection of nucleic acid sequences encoding an epithelial cell ECGI, for example, the primers used in the Examples below.

Therapeutic Use

ECGI protein for therapeutic use is produced from epithelial cell cultures under serum free conditions or by recombinant means. Preferably, ECGI protein is produced in yeast or higher eucaryotic cells to achieve phosphorylation of the protein. Recombinant protein is produced in host cells or by synthetic means.

Functional ECGI is administered to patients by known method for the administration of phosphoprotein, preferably by injection, to increase inhibitor levels in the bloodstream and increase the inhibitor's interactions with the desired epithelial.

The protein may be delivered to the patient by methods known in the field for delivery of phosphorylated protein agents. In general, the inhibitor is mixed with the delivery vehicle and administered by injection.

The dosage of inhibitor to be administered may be determined by one skilled in the art, and will vary with the type of treatment modality and extent of disease. Since Mammastatin inhibits approximately 50% of mammary cancer cell growth at a concentration of 10 ng/ml and stops growth at about 20–25 ng/ml in vitro, a useful therapeutic dosage range of ECGI is about 2.5 µg to about 250 µg administered daily dose. Preferred is approximately 125 µg daily administered dose. The aim of the administration is to result in a final body dose that is in the physiological (e.g. 15–50 ng/ml) or slightly higher range (for example, 25–75 ng/ml). For clinical use, the preferred dosage range is about 500 ng/ml for initial treatment of metastatic disease, followed by a maintenance dosage of about 50 ng/ml. In clinical studies using Mammastatin, an administered daily dose of about 50 ng/ml to about 750 ng/ml was sufficient to induce remission to Stage IV breast cancer patients.

Since active ECGI is a phosphorylated protein, it is anticipated that multiple doses of the inhibitor will be required to maintain growth inhibiting levels of ECGI in the patient's blood. Also, since ECGI generally acts as a cytostatic agent rather than a cytocidal agent, it is expected that a maximum effect of the inhibitor will require regular maintenance of inhibitor levels in epithelial cell cancer patients.

In its preferred use, the ECGI is administered in high dosages (>50 ng/ml, preferably about 50–500 ng/ml) to induce tumor regression. Lower, maintenance doses (<50 ng/ml, preferably 20–50 ng/ml) are used to prevent cancer cell growth.

Clinical experience with administered Mammastatin in Stage IV breast cancer patients indicates a useful dose is that which maintains physiological levels of Mammastatin in the blood. Administration is preferably daily, but, may be, for example, by continuous infusion, by slow release depot, or by injection once every 2–3 days. Anecdotal evidence suggests continuous administration may induce feedback inhibition, thus, a preferred administration scheme is to administer daily dose of Mammastatin for approximately 25–28 days, followed by 2–5 days without administration.

Diagnostic Assay

Assays of the present invention for detecting the presence of the functional inhibitor in human tissue and serum are useful in screening patients for epithelial cell cancer, for screening the population for those at high risk of developing epithelial cell cancer, for detecting early onset of epithelial cancer, and for monitoring patient levels of inhibitor during treatment. For example, analysis of a patient's blood ECGI, for example, may indicate a reduced amount of high molecular weight, phosphorylated prostate ECGI, as compared with a normal control or with the patient's prior prostate ECGI profile. Such a change is correlated with increased risk of prostate cancer, with early onset of prostate cancer, and with advancing metastatic prostate cancer. Diagnostic assay for phosphorylated, active, 55 kD prostate ECGI preferably is by Western blot immunoassay, or ELISA using specific anti-ECGI antibodies. Screening, for example, in serum, is preferably by immunoassay, e.g., ELISA, Western blot, or dot blot assay.

For best results, the patient samples should be assayed within a short time of sampling (within one week), stored at 4° C. (less than one year), or frozen for long term storage. Most preferably, samples are frozen until time of assay.

EXAMPLES

The invention may be better understood by reference to the following Examples, which are not intended to limit the invention in any way.

Example 1

Multiple Tissue Expression of ECGI

Northern blot analysis was performed on a multiple tissue expression array (Clonetech, Inc. #7775-1) to demonstrate the expression of ECGI in a variety of epithelial cell tissues. A digoxin-labeled EcoR1 fragment of Mammastatin, containing approximately 1800 base pairs of the 3' region of pMammC, SEQ ID NO: 3 (approximately nucleotide 359–end) was used as a probe. The DIG-labeled Mammastatin cDNA was hybridized to the array in 10 ml easy HYB solution (Roche) for 16 hours at 65° C., with 65° C. washes, anti-DIG antibody hybridization and CSPD development performed according to the manufacture's instructions. The blot was then exposed to Kodak X-OMAT film for 30 minutes at room temperature.

The tissue plan of the multiple tissue expression array is shown in FIG. 1A. Hybridization of the Mammastatin cDNA to the mRNA of the array is shown in FIG. 1B, and demonstrates the variety of epithelial cell tissues expressing a Mammastatin-like ECGI sequence. Specific tissues that hybridized to the Mammastatin cDNA included: central nervous system, heart, small intestine, large intestine, appendix, rectum, lymphatic cells, bone marrow cells, lung and air passages, bladder, uterus, prostate, testis, ovary, liver, pancreas, adrenal gland, salivary gland, and mammary gland.

Example 2

Normal Versus Cancerous Prostate Cells

Normal prostate cells obtained from surgical samples and cancerous prostate cells, LnCap, obtained from the American Type Culture Collection (ATCC) were incubated and analyzed for the production of a prostate ECGI. The cells were cultured in DMEM/F12 media with 40 $\mu$M calcium, supplemented with 5% Chelex-treated horse serum, 10 ng/mL EGF, 10 $\mu$g/mL insulin, 100 ng/mL Cholera toxin and 1 $\mu$g/mL hydrocortisone for four days. Conditioned media samples were then collected and analyzed.

Normal human mammary cells obtained from patient samples were incubated in the same medium and Mammastatin secreted into the culture medium was used as a control. Serum obtained from breast cancer patients was also analyzed and used as a control.

Figure 2:
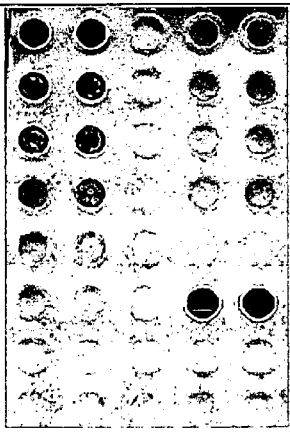
FIG. 2 is a computer scanned image of a dot blot assay showing control, Mammastatin standard protein, serum samples from breast cancer patients, and conditioned medium from normal and cancerous human prostate cells probed with anti-Mammastatin antibody, 7G6.

Sample fluids were collected and loaded by suction onto a nitrocellulose membrane on a dot blot apparatus. The membranes were then probed with the anti-Mammastatin antibody 7G6, and antibody binding was detected with goat-anti mouse antibody labeled with alkaline phosphates. Color was developed with NBT/BCIP substrate system (Life Technologies). The results are shown in FIG. 2.

The anti-Mammastatin antibody recognized a protein produced by normal prostate cells but not cancerous prostate cells. This is analgous to the antibody's recognition of the mammary cell growth inhibitor, Mammastatin, produced by normal mammary cells, but not breast cancer cells. This data, in combination with the data from Example 1, demonstrates the production of Mammastatin-like ECGI in other epithelial cell tissues, and particularly, in prostate cells.

Example 3

Differential Expression of ECGI in Prostate, Colon, and Ovary

Prostate

Figure 3:
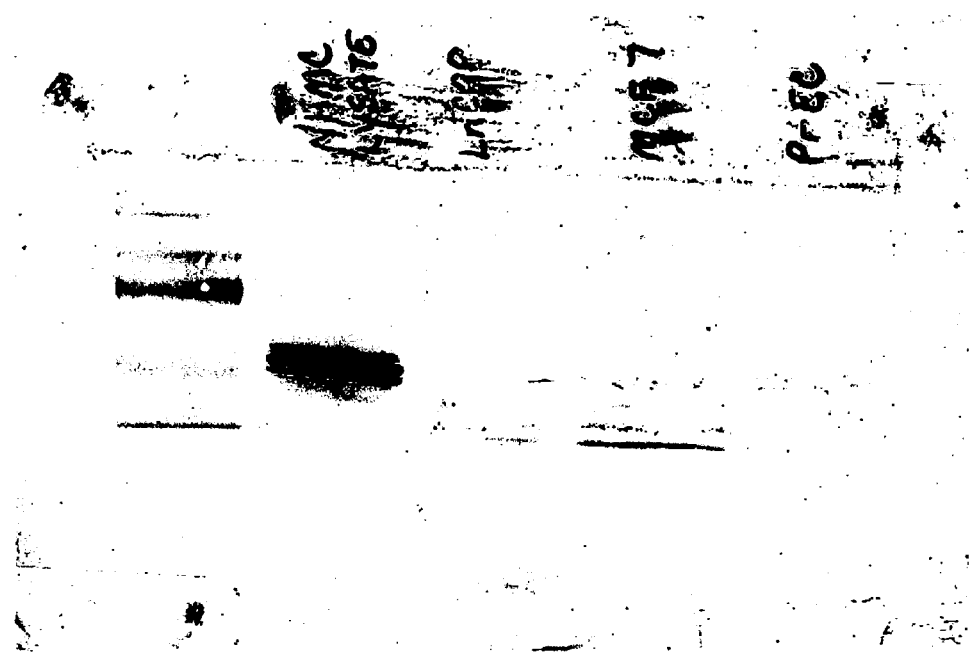
FIG. 3 is a computer scanned image of a Western blot assay, showing normal human mammary cell lysate (A), human prostate cancer LnCap cell lysate (B), MCF7 breast cancer cell lysate (C), and normal human prostate cell lysate (D) probed with anti-Mammastatin antibody, 7G6.

Normal prostate cells (Clonetech, Inc.), LnCap prostate cancer cells (A.T.C.C.), MCF7 breast cancer cells (A.T.C.C.) and normal human mammary cells (obtained from hospital tissue) were incubated as described above for Example 2. After at least 48 hours incubation, cells were lysed in sample loading buffer and analyzed for the presence of ECGI by Western blot, using the anti-Mammastatin antibody, 7G6 as a probe. Normal human mammary cell protein (NHMC) lysate (1 mg/ml) was used as a Mammastatin control (A). The data are shown in FIG. 3.

Normal prostate cell lysate (D) contained a protein that was recognized by anti-Mammastatin antibody, while prostate cancer cells (LnCap) (B) and breast cancer cells (MCF7) (C) did not. The protein recognized in the prostate cell lysate (D) was of a similar size to that of Mammastatin (A).

Colon and Prostate

Normal prostate cells (Clonetech, Inc.), LnCap prostate cancer cells (A.T.C.C.), Sw 948 colon cancer cells (A.T.C.C.), and normal colon epithelial cells (obtained from patient surgery tissue) were incubated as described above for Example 2. Cell lysates were prepared in sample loading buffer and analyzed for expression of ECGI by Western blot, using the anti-Mammastatin antibody, 7G6 as a probe.

Figure 4:
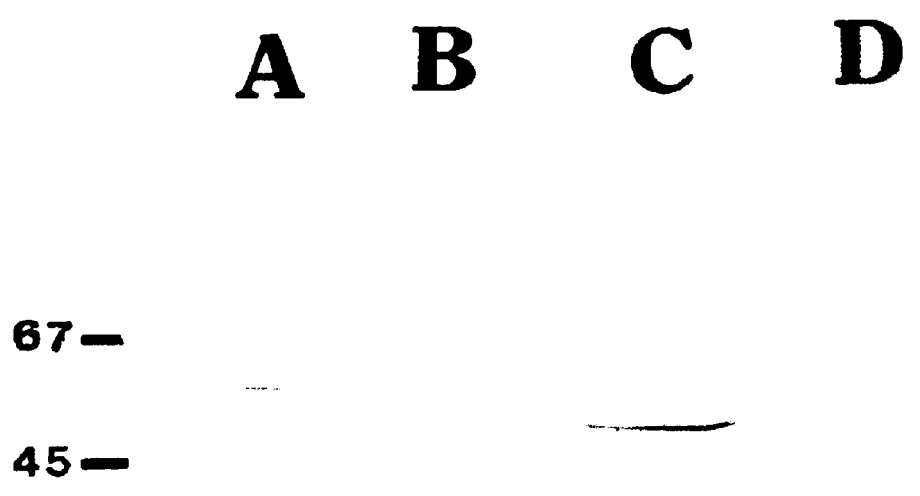

As shown in FIG. 4, normal prostate (A) and normal colon (C) epithelial cells expressed a protein that was recognized by the anti-Mammastatin antibody, while cancer cells from these tissues did not (B,D). The differential expression of protein is similar to that demonstrated for Mammastatin in breast tissue. In addition, the pattern of bands shown in the Western blot for normal prostate and colon tissues is similar to the Phosphorylation pattern demonstrated for Mammastatin produced in normal human mammary cells. A larger prominent band is shown together with two smaller, fainter bands. This pattern has been correlated with Phosphorylation of Mammastatin.

Prostate ECGI is shown in the Western blot analysis (FIG. 4) to have an approximate molecular weight of 51 kilodaltons; Colon ECGI is shown to have an approximate molecular weight of 50 kilodaltons.

Ovary

Figure 5:
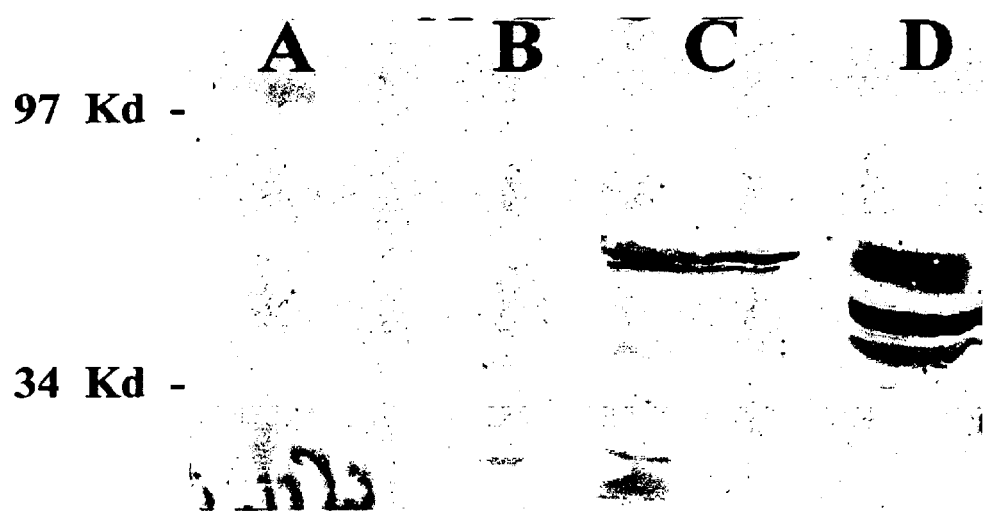
FIG. 5 is a computer scanned image of a Western blot assay, showing cell lysates from human ovarian cancer cells (B), normal human ovarian cells (C), and normal human mammary cells (D) probed with anti-Mammastatin antibody, 7G6. Lane A contained molecular weight standards.

OvCar-ovarian cancer cells (A.T.C.C.), normal human ovarian cells (patient surgery tissue) and normal human mammary cells (patient surgery tissue) were incubated as described above for Example 2. After an incubation period of at least 48 hours, direct lysates were prepared by removing growth media and rinsing cells with saline and SDS-PAGE sample loading buffer until viscous. Lysates were collected and separated on 10% SDS-PAGE, transferred electrophoretically onto nitrocellulose, and probed with the 7G6 anti-Mammastatin antibody. The data are shown in FIG. 5, where lane A contains molecular weight standards; B, OvCar-ovarian cancer cell lysate; C, normal human ovarian cell lysate; and D, normal human mammary cell lysate.

FIG. 5 demonstrates that a Mammastatin-like ECGI protein is produced in normal human ovarian tissues and is recognized by anti-Mammastatin antibody. The protein is not expressed in the ovarian cancer cells analyzed. The ovarian ECGI has an approximate molecular weight of 60 kilodaltons.

Example 4

Differential Detection of Prostate ECGI in Blood

Figure 6:
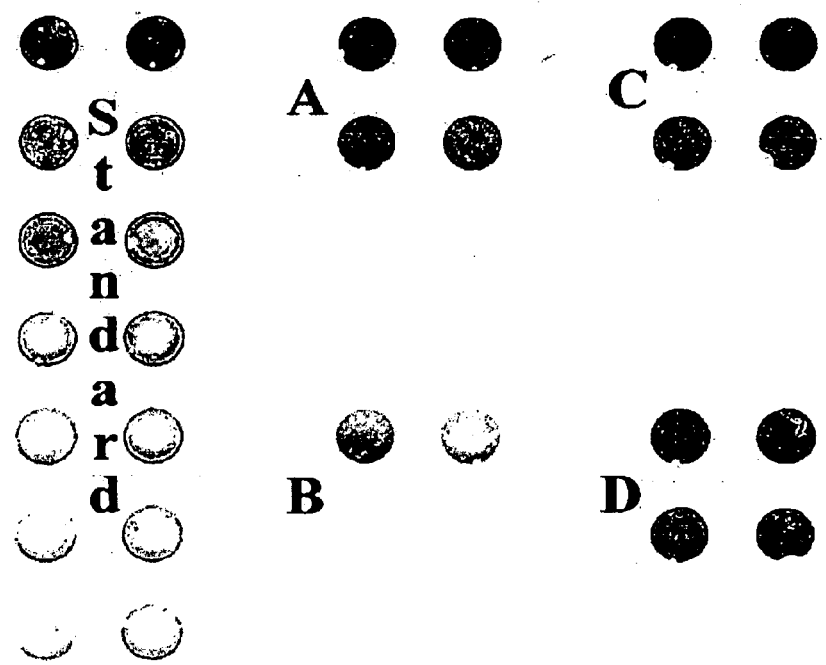
FIG. 6 is a computer scanned image of a dot blot assay showing serum samples from healthy male adults (A,C,D) and from a prostate cancer patient (B) probed with anti-Mammastatin antibody, 7G6.

Serum samples from three healthy male volunteers were analyzed for the presence of the prostate ECGI, and compared with that of serum from a prostate cancer patient. Serum samples were loaded at 400 microliter and 200 microliter samples in duplicate. The samples were drawn onto nitrocellulose by vacuum in a 96 well dot blot apparatus. The filters were then probed with the anti-Mammastatin antibody, 7G6, and developed with NBT/BCIP substrate. The data are shown in FIG. 6.

Normal human mammary cell (NHMC) cultures produced standard conditioned medium for comparison. Standards, in duplicate, contained 400, 200, 100, 50, 25, 12, and 6 microliters of NHCM medium. Serum samples from healthy adult males (A,C,D) and from an adult prostate cancer patient (B) were assayed using 400 and 200 microlites of serum sample. A prominent signal from normal serum (A,C,D) demonstrated the presence of prostate ECGI, while the prostate cancer patient's serum showed only a weak signal.

Example 5

Inhibitory Activity of Prostate ECGI

Normal prostate cells (Clonetech, Inc.), PC3 and LnCap prostate cancer cells (A.T.C.C.) were plated at a density of $5.0 \times 10^4$ cells per milliliter in 12 well plates in RPMI medium containing 10% fetal bovine serum. After 24 hours, the cultures were supplemented with 10% conditioned medium. Each sample was run in triplicate. Plates were allowed to incubate for six days at 37° C. and 5% $CO_2$, and at the end of the incubation period, cells were lysed with Cetrimide and counted using a Colter Counter. Percent inhibition was calculated by comparing treated versus non-treated wells, and the data shown in the table below. Androgen-insensitive PC3 cells were not inhibited by the normal prostate cell media or by the conditioned medium obtained from normal prostate cells. In contrast, LnCap cells were inhibited by the addition of growth medium, with the inhibition somewhat greater by media derived from normal prostate versus media derived from cancer cells.

| Cell Type | % Inhibition by Normal Prostate medium | % Inhibition by Prostate Tumor medium |
|---|---|---|
| LnCap #1 | 22.5 +/− 3.3 | 8.3 +/− 0.4 |
| LnCap #2 | 22.7 +/− 0.6 | 16.7 +/− 15.8 |
| PC3 | 0 | 0 |

Example 6

Isolation and Characterization of Prostate ECGI DNA

Nucleic acid libraries were produced from the mRNA of normal prostate cells (patient surgery tissue) and from LnCap, prostate tumor cells (A.T.C.C.).

The nucleic acid sequences in the normal and cancerous prostate cell libraries were incorporated into vectors and used to transform bacteria. Colonies of bacteria expressing the normal and cancer prostate cell nucleic acid sequences were screened by hybridization with a digoxin-labeled Mammastatin nucleic acid probe under stringent conditions, as described above.

The positive colonies were selected and grown in LB broth. Plasmids obtained from the positive colonies were purified and digested with ECO R1 and Xhol to release the CDNA inserts. The digested DNA was then separated on a 1% agarose gel (see FIG. 7A) and the separated DNA was subjected to Southern blot analysis using the digoxin-labeled Mammastatin fragment as a probe. As shown in FIG. 7 below, two prostate ECGI clones were isolated, each having an approximate size of 2 Kb: One clone was isolated from the normal prostate tissue library (PRN2.1) and one from the LnCap prostate tumor cell library (PRT-6).

Figure 8:
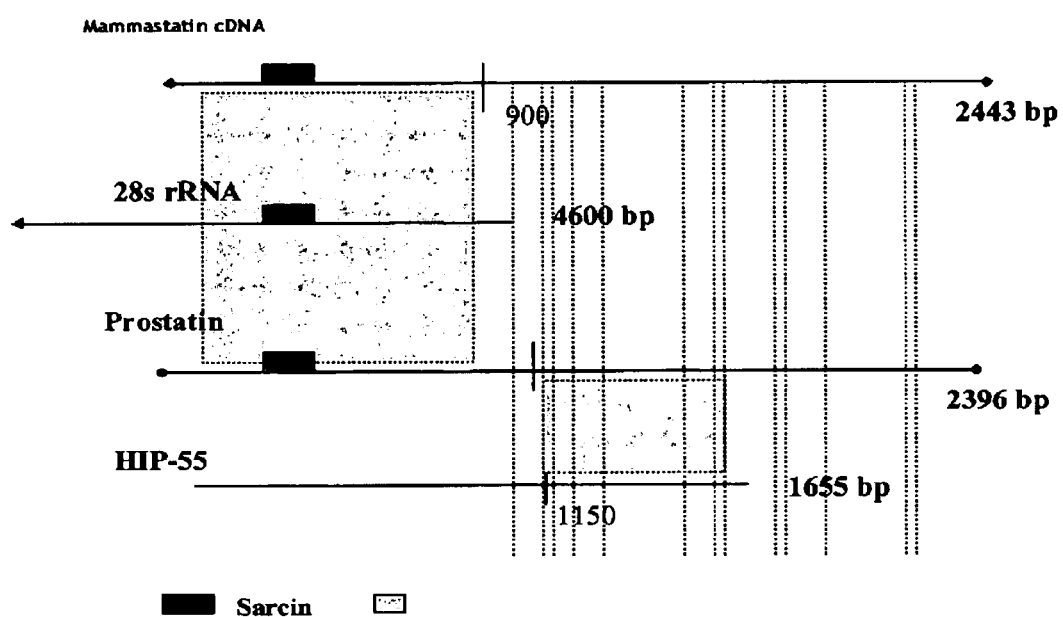
FIG. 8 is a diagramatic representation of Prostate ECGI and its structural relationship to other sequences.

PRT-6 was further characterized, and its nucleic acid sequence was determined. As shown below in Table 1, the nucleic acid sequence encoding Prostate ECGI has substantial identity to Mammastatin (greater than 90%) at the 5' end of the molecule (approximately nucleotides 15–1032 of MammC), with little or no identity at the 3' end of the molecule. These regions of similarity and distinction are shown diagrammatically in FIG. 8.

Example 7

Isolation and Characterization of Prostate ECGI DNA

Nucleic acid libraries were constructed from the mRNA or normal prostate cells (obtained from patient surgery tissue) and from LnCap prostate tumor cells (A.T.C.C.). The library cDNA was used to transfer *E. coli* and plated out for colony hybridization. The colonies were screened with a digoxin-labeled Mammastatin C fragment generated by PCR using external PCR primers M200 and M2200.

M200:   GCGCCGGCCGGGCGCGACCCG [Sequence ID NO: 5]

M2200:  GCAATCTCAGCGCACTGCTGC [Sequence ID NO: 6]

Bacterial colonies expressing prostate ECGI clones were hybridized to the labeled Mammastatin probe under strict hybridization conditions, as described above.

Example 8

Homology of Prostate ECGI

The prostate ECGI sequence (SEQ ID NO: 4) was analyzed against nucleic acid sequences present in GenBank. Portions of two molecules showed some similarity to domains within the prostate ECGI sequence: 28SmRNA (SEQ ID NO: 7)and Hip55 (SEQ ID NO: 8).

28SmRNA homology has been identified in many gene sequences with importance in growth regulation (Hu et al., 1999, PNAS 96:1339–1344; Mauro et al., 1997, PNAS 94:422–427). Hip55 is a protein that binds to hematopoetic progenitor type 1 kinase, a protein involved in the src signal transduction pathway (Ensena et al, 1999, JBC 274:33945–50).

Using the open reading frame known for Hip55, a putative amino acid sequence was deducted for the prostate clone. As shown below in Table 3, the translation includes several internal stop codons.

Also using the Hip55 ORF, a putative amino acid sequence was deduced for MammB and MammC sequences, shown in Tables 4 and 5.

TABLE 1 pMammC and Prostate ECGI

```
                            1                                                  50
    pMamm C      (1)    --------------------------------------------------
Prostate GIP     (1)    GCACGAGATTCCCACTGTCCCTACCTACTATCCAGCGAAACCACAGCCAA
   Consensus     (1)
                            51                                                100
    pMamm C      (1)    ------------------------------------------------GA
Prostate GIP    (51)    GGGAACGGGCTTGGCGGAATCAGCGGGGAAAGAAGACCCTGTTGAGCTTG
   Consensus    (51)
                            101                                              150
    pMamm C      (3)    ATTGGGCACGAG  A  GTGAAGAGACATGAGAGGTGTAGAATAAGTGGGA
Prostate GIP   (101)    ACTGTAGTGTG   A  GGTGAAGAGACATGAGAGGTCTAGAATAAGTGGGA
   Consensus   (101)    A TC       C    GCACGGTGAAGAGACATGAGAGGTGTAGAATAAGTGGGA
                            151                                              200
    pMamm C     (53)    GGCCCCCGGCGCCCCCCCGGTGTCCCCGCGAGGGGCCCGGGCGGGGTCC
Prostate GIP   (151)    GGCCCCCGGCGCCCCCCCGGTGTCCCCGCGAGGGGCCCGGGCGGGGTCC
   Consensus   (151)    GGCCCCCGGCGCCCCCCCGGTGTCCCCGCGAGGGGCCCGGGCGGGGTCC 201                                              250
    pMamm C    (103)    GCCGGCCCTGCGGGCCGCCGGTGAAATACCACTACTCTGATCGTTTTTC
Prostate GIP   (201)    GCCGGCCCTGCGGGCCGCCGGTGAAATACCACTACTCTGATCGTTTTTC
   Consensus   (201)    GCCGGCCCTGCGGGCCGCCGGTGAAATACCACTACTCTGATCGTTTTTC
                            251                                              300
    pMamm C    (153)    ACTGACCCGGTGAGGCGGGGGGCGAGCCCCGAGGGGCTCTCGCTTCTGG
Prostate GIP   (251)    ACTGACCCGGTGAGGCGGGGGGCGAGCCCCGAGGGGCTCTCGCTTCTGG
   Consensus   (251)    ACTGACCCGGTGAGGCGGGGGGCGAGCCCCGAGGGGCTCTCGCTTCTGG
                            301                                              350
    pMamm C    (203)    CGCCAAGCGCCCGGCCGCGCGCCGGCCGGGCGCGACCCGCTCCGGGGACA
Prostate GIP   (301)    CGCCAAGCGCCCGGCCGCGCGCCGGCCGGGCGCGACCCGCTCCGGGGACA
   Consensus   (301)    CGCCAAGCGCCCGGCCGCGCGCCGGCCGGGCGCGACCCGCTCCGGGGACA 351                                              400
    pMamm C    (253)    GTGCCAGGTGGGGAGTTTGACTGGGGCGGTACACCTGTCAAACGGTAACG
Prostate GIP   (351)    GTGCCAGGTGGGGAGTTTGACTGGGGCGGTACACCTGTCAAACGGTAACG
   Consensus   (351)    GTGCCAGGTGGGGAGTTTGACTGGGGCGGTACACCTGTCAAACGGTAACG
                            401                                              450
    pMamm C    (303)    CAGGTGTCCTAAGGCGAGCTCAGGGAGGACAGAAACCTCCCGTGGAGCAG
Prostate GIP   (401)    CAGGTGTCCTAAGGCGAGCTCAGGGAGGACAGAAACCTCCCGTGGAGCAG
   Consensus   (401)    CAGGTGTCCTAAGGCGAGCTCAGGGAGGACAGAAACCTCCCGTGGAGCAG
                            451                                              500
    pMamm C    (353)    AAGGGCAAAAGCTCGCTTGATCTTGATTTTCAGTACGAATACAGACCGTG
Prostate GIP   (451)    AAGGGCAAAAGCTCGCTTGATCTTGATTTTCAGTACGAATACAGACCGTG
   Consensus   (451)    AAGGGCAAAAGCTCGCTTGATCTTGATTTTCAGTACGAATACAGACCGTG 501                                              550
    pMamm C    (403)    AAAGCGGGGCCTCACGATCCTTCTGACCTTTTGGGTTTTAAGCAGGAGGT
Prostate GIP   (501)    AAAGCGGGGCCTCACGATCCTTCTGACCTTTTGGGTTTTAAGCAGGAGGT
   Consensus   (501)    AAAGCGGGGCCTCACGATCCTTCTGACCTTTTGGGTTTTAAGCAGGAGGT
                            551                                              600
    pMamm C    (453)    GTCAGAAAAGTTACCACAGGGATAACTGGCTTGTGGCGGCCAAGCGTTCA
Prostate GIP   (551)    GTCAGAAAAGTTACCACAGGGATAACTGGCTTGTGGCGGCCAAGCGTTCA
   Consensus   (551)    GTCAGAAAAGTTACCACAGGGATAACTGGCTTGTGGCGGCCAAGCGTTCA
                            601                                              650
    pMamm C    (503)    TAGCGACGTCGCTTTTTGATCCTTCGATGTCGGCTCTTCCTATCATTGTG
Prostate GIP   (601)    TAGCGACGTCGCTTTTTGATCCTTCGATGTCGGCTCTTCCTATCATTGTG
   Consensus   (601)    TAGCGACGTCGCTTTTTGATCCTTCGATGTCGGCTCTTCCTATCATTGTG
                            651                                              700
    pMamm C    (553)    AAGCAGAATTCACCAAGCGTTGGATTGTTCACCCACTAATAGGGAACGTG
Prostate GIP   (651)    AAGCAGAATTCACCAAGCGTTGGATTGTTCACCCACTAATAGGGAACGTG
   Consensus   (651)    AAGCAGAATTCACCAAGCGTTGGATTGTTCACCCACTAATAGGGAACGTG 701                                              750
    pMamm C    (603)    AGCTGGG TTAGACCGTCGTGAGACAGGTTAGTTTTACCCTACTGATGAT
Prostate GIP   (701)    AGCTGGA TTAGACCGTCGTGAGACAGGTTAGTTTTACCCTACTGATGAT
   Consensus   (701)    AGCTGGG TTAGACCGTCGTGAGACAGGTTAGTTTTACCCTACTGATGAT
                            751                                              800
    pMamm C    (653)    GTGTTGTTGCCATGGTAATCCTGCTCAGTACGAGAGGAACCGCAGGTTCA
Prostate GIP   (751)    GTGTTGTTGCCATGGTAATCCTGCTCAGTACGAGAGGAACCGCAGGTTCA
   Consensus   (751)    GTGTTGTTGCCATGGTAATCCTGCTCAGTACGAGAGGAACCGCAGGTTCA
                            801                                              850
    pMamm C    (703)    GACATTTGGTGTATGTGCTTGGCTGAGGAGCCAATGGGCGAAGCTACCA
Prostate GIP   (801)    GACATTTGGTGTATGTGCTTGGCTGAGGAGCCAATGGGCGAAGCTACCA
   Consensus   (801)    GACATTTGGTGTATGTGCTTGGCTGAGGAGCCAATGGGCGAAGCTACCA
```

TABLE 1-continued pMammC and Prostate ECGI

```
                  851                                               900
     pMamm C  (753) TCTGTGGGATTATGACTGAACGCCTCTAAGTCAGAATCCCGCCCAGGCGG
Prostate GIP  (851) TCTGTGGGATTATGACTGAACGCCTCTAAGTCAGAATCCCGCCCAGGCGG
   Consensus  (851) TCTGTGGGATTATGACTGAACGCCTCTAAGTCAGAATCCCGCCCAGGCGG
                  901                                               950
     pMamm C  (803) AACGATACGGCAGCGCCGCGGAGCCTCGGTTGGCCTCGGATAGCCGGTCC
Prostate GIP  (901) AACGATACGGCAGCGCCGCGGAGCCTCGGTTGGCCTCGGATAGCCGGTCC
   Consensus  (901) AACGATACGGCAGCGCCGCGGAGCCTCGGTTGGCCTCGGATAGCCGGTCC
                  951                                              1000
     pMamm C  (853) CCCGCCTGTCCCCGCCGGCGGGCCGCCCCCCC  CTCCACGCGCCCCGCG
Prostate GIP  (951) CCCGCCTGTCCCCGCCGGCGGGCCGCCCCCC--CTCCACGCGCCCCGCG
   Consensus  (951) CCCGCCTGTCCCCGCCGGCGGGCCGCCCCCCC  CTCCACGCGCCCCGCG
                 1001                                              1050
     pMamm C  (903) CGCGCGGGAGGGCGCGTGCCCCGCCGCGCGCCGGGACCGGGGTCCGGTGC
Prostate GIP  (999) CGCGCGGGAGGGCGCGTGCCCCGCCGCGCGCCGGGACCGGGGTCCGGTGC
   Consensus (1001) CGCGCGGGAGGGCGCGTGCCCCGCCGCGCGCCGGGACCGGGGTCCGGTGC 1051                                              1100
     pMamm C  (953) GGAGTGCCCTTCGTCCTGGGAAACGGGGCGCGGCCGGAAAGGCGGCCGCC
Prostate GIP (1049) GGAGTGCCCTTCGTCCTGGGAAACGGGGCGCGGCCGGAAAGGCGGCCGCC
   Consensus (1051) GGAGTGCCCTTCGTCCTGGGAAACGGGGCGCGGCCGGAAAGGCGGCCGCC
                 1101                                              1150
     pMamm C (1003) CCCTCGCCCGTCACGCACCGCACGTTCGTGCT---CGTGCCGAATTCGG
Prostate GIP (1099) CCCTCGCCCGTCACGCACCGCACGTTCGTGGGGAAGCTGCGC-TAAACG
   Consensus (1101) CCCTCGCCCGTCACGCACCGCACGTTCGTG   C TG CG T     C
                 1151                                              1200
     pMamm C (1050) AGGAGTAGCACCATTGACAATAGACATACAAGTGCATGTATCTTTATGAT
Prostate GIP (1148) ACTCCATGTCCAGTCCTCA--GCGTGGCAAGCTGAGG-AGCCCTTCCG
   Consensus (1151) AC  A C CCA TC  A G C  CAAG   AGA C   T   T
                 1201                                              1250
     pMamm C (1100) ATAATGAATTGTTTTGCTTTGGGTAGATATCCAGTAGTGGGATTGCTAGA
Prostate GIP (1195) GCA--GAAG-GAGCTCACCCAACCAGAGACCGACT-------TTGGCAGA
   Consensus (1201)    A   GAA  C   TC      AGA A CCA T       TTG AGA 1251                                              1300
     pMamm C (1150) TCACGTGGTAGTCTATTTGTGGTTTATTGAGAAATCTGATACTGATTT
Prostate GIP (1235) GAGGCAGCTGCTGGCATCTGAAAGCCCAGGGCAGATCTCTCTGCTGAG--
   Consensus (1251)     CC GT  T C AT TC  G      G  A ATCT C T CTGA
                 1301                                              1350
     pMamm C (1200) CCATAGAGGTTGTACAAATTTACATGCCTAGCAAGTGATTTTTTTAAATA
Prostate GIP (1283) -----GAGCCGGCGGC------CAGGCAGTCCTCCATGTCTGGTGCAGGCA
   Consensus (1301)      GAG  G C        CA C CT C   TG T T A      A
                 1351                                              1400
     pMamm C (1250) TGAAAGAATGGTCTGGAGAAATGCCCCTGATTAGTATCCCCCTTTTACCT
Prostate GIP (1322) GAAGAGGAGGCTGTGTATGAG-GAACCTCCAGAGCAGGAG------ACCT
   Consensus (1351)   A  AG A GT TG A  G  CCTC  AG A        ACCT 1401                                              1450
     pMamm C (1300) CTCTAGTGCAGAATGACTTGAAGGGGTACAGGTATTTACAAAGTTTGATTA
Prostate GIP (1365) -TCTAC----GAGCAGGCCCACTGGTGCAGCAG----CAAAGTGGTGGC
   Consensus (1401)   TCTAC    GA   C   C A  GGT CAG     CAAG T C
                 1451                                              1500
     pMamm C (1350) TACAGACAAATTGAATATTGAAATTTGTGCATAAGAGGGACAGATTTTA-
Prostate GIP (1406) TCTGAGCACATTGACCAC--CACATTGAGGGCCAGGGGGTCAGTGGGCAA
   Consensus (1451) T   CA ATTGA  A    A TTC G   AG GGC CAG       A
                 1501                                              1550
     pMamm C (1399) GGATTCAAAG----TTGTATGAACAAGGAGAAGTGCTCTAGGCAGTTGCA
Prostate GIP (1454) GGGCTCGTGTGCCCCGTGCCCGTAGCACTACCAGGCAGCCGACAGA--CA
   Consensus (1501) GG TC  G    T    TG AC A  AC AG    C    GAC   CA
                 1551                                              1600
     pMamm C (1445) AAGCTGGAATTGGAAATGTGAGATGAAATACATTTGTAGTAGTACCACCA
Prostate GIP (1502) GAGATCTCCTTTGA---CCCGA-GAACCTCATCACGGGCATCGAGGTGA
   Consensus (1551)  AG T   TT GA    C CGA  GAA   CAT C G A          A 1601                                              1650
     pMamm C (1495) GC-ATATATTCTACTGAATTGGCTTTGTGATCATCATTAATACCTACTTA
Prostate GIP (1548) TGGACGAAGGCTGGTGCGTGCCTATGGCCCGGATGCCATTTTGGCATG
   Consensus (1601)  C A   A  CT TG   TGGCT TG G     AT       C T
                 1651                                              1700
     pMamm C (1544) TTAAAACTAATGAAAAGGGTTTATATCAAATATACTTTAAGGTATAAAAA
Prostate GIP (1598) TCCCCTGCCAACTACGTCGAGCTCATTGAGTGAGGCTGAGGCACATCTT
   Consensus (1651) T T        A   A  GG    AT AT      T A GG A A
                 1701                                              1750
     pMamm C (1594) TCAAAATATAGGCAAAGC-TGTTTCTTAGCATGTTATTTCAAAGAT
Prostate GIP (1648) GCCCTTCCCCTCTCAGACATGGCTGGTAATGCTGGAAGAGGAGGCGTG
   Consensus (1701)    C T       TA C TG  TTC TTA  T AA    A   C
```

TABLE 1-continued pMammC and Prostate ECGI

```
                        1751                                              1800
   pMamm C  (1643) AAAATAACTACCGTCTATTGGCCATTTATACTGTACCAG-ACAATGTGTT
Prostate GIP (1698) GGAGTTGA---C----ATTCAGCACTCTTCCAGGAATAGGACCCCAGTG
   Consensus (1751)    AT G    C    ATT GCA T  TCG A AG AC C    GT 1801                                              1850
   pMamm C  (1692) TGTCACATTTCAAAAATGTTGTGATGGTAATGTTCACAATAATTCTGTAG
Prostate GIP (1741) AGG-ATGAGGCTCAGGGCTGCCTCCAGCTAAG-CAGACTCAGCTTGTCA
   Consensus (1801)   G  A     C    AG TC C    G   TG  CA A T A   CTGT 1851                                              1900
   pMamm C  (1722) GGTGAGAAATAGTCTTACCGTAGTAAGACT-ATTCAGTAAAC---GAAACC
Prostate GIP (1789) CCCCAATGCAGCAATGGCCTGGTGATTCCACACATCCTTCCTGCATCC
   Consensus (1851)          AA   AG  T CTGTA C  A CA       C  G A CC 1901                                              1950
   pMamm C  (1789) TGTCAACCTTGGAGTTCAACTTGCGCAAAGTTAGTAACAGGACTAGGACT
Prostate GIP (1839) CCCGACCCTCCCAGA-CAGCTTAGCTCTTGCCCCTGACAGGATACTGAGC
   Consensus (1901)  C GA CCT   AG  CA CTTG        G     T ACAGGA    GA 1951                                              2000
   pMamm C  (1839) TGAACGTGAAGCATCAG--ACTCGAGATCTCTGCATACCACACTGGTAGC
Prostate GIP (1888) CAAGCCCTGCCTGTGGCCAAGCCGTGAGTGGCCACTGCCAAGCTGCGGGG
   Consensus (1951)   A CC     C  T  C A  CC GA     C  T CCA CTGC  G 2001                                              2050
   pMamm C  (1887) ACATCTGCTGTCATCTTATTTCTGCTCCTGTATATTCGCTTTTTATTT
Prostate GIP (1938) AAGGGTCCTGAGCAGGGGCATCTGGCAGGCCTCTGGCTGCTTCTGCATTT
   Consensus (2001)  A   GT C    CA      TC GG    CT T    T CC TT    ATTT 2051                                              2100
   pMamm C  (1937) CCTTTCCCTTCCTCCCACAACCCCTTTGTTGCCCCCATTTCATTTCTTTCT
Prostate GIP (1988) A-TTTGCCTT---------------TTT-TGTT----TTTCTCTTGCTTCT
   Consensus (2051)    TTT CCTT              TTT TC     TTTCT TT TTCT 2101                                              2150
   pMamm C  (1987) TTTTAATTGTTAATTACATAACTAATACATGCTTAACAGAACAATTGATA
Prostate GIP (2018) AAGGGGTGCTGGCCACCACTGTTTAGAATGACCCTTGGGAAACAGTGAACG
   Consensus (2101)       T GT     CA     TA A    C   T  GAACA T  A 2151                                              2200
   pMamm C  (2037) TAGCACAAAAGGATATAAAGTACGGGTGAGTGAT--AGCTCATCCCTGTA
Prostate GIP (2068) TAG---AGAATTGTTTTTAGCA-GAGTTTGTGACCAAAGTCAGAGTGG--
   Consensus (2151) TAG    A AA  T T AG A G GTGA   A TCA    G 2201                                              2250
   pMamm C  (2085) ATCTAGCACTTTGAAGGCGAAGGCAGGCAGATCACTGAGTCCAGAGT
Prostate GIP (2112) ATCATGGTGGTTGGCAG--CAGGGAATTTGTCTTGTTGGAGCGT---GC
   Consensus (2201) ATC T G   TTTGG AG  CA GG A       T   T GAG C     G 2251                                              2300
   pMamm C  (2135) TGGAGAGCAGCCGTGGGCAACATGGTGAAAGCCTGTCTCTACAAAAAAATA
Prostate GIP (2157) TCTGTGCTCCCGACTCCATTTCTCAGTCCGTGTCCAGGGGCTATGGGAAG
   Consensus (2251) TC   C  CC   CA       TG  CTG CT  C A    A 2301                                              2350
   pMamm C  (2185) CAAAAATTTAGCCGGGCGTGCTGGCCAGACACCTCTAGTCTCCAGCTAGTCT
Prostate GIP (2207) TGGGGAAGCAAGATGGCCAAGCCTCCCAG---CCTCGGGTATTCAAAAAC---
   Consensus (2301)      AT  AG  GG C  GCT CAC    CCTG     TCA    AC 2351                                              2400
   pMamm C  (2235) GAGCCGTGAGGTGGGAAGATTGATTGAGCCCAGGAGGTGGAAGCTGCAGG
Prostate GIP (2251) ---GGCAGACACAACATG-TTCCTCCACGGGGCTCACTCGATGC--GTGC
   Consensus (2351)     GGC GA    AG TT  T  A  C     T GA GC  C GC 2401                                              2450
   pMamm C  (2285) AGTGCGGTGAGATTGGGCCATTGCACTCCAGCCTGGGTGAGAGAGAGAGA
Prostate GIP (2295) AGGCCCAGTGTGTGGCCTCAACTGATTGTGAGTTCAGGAAAAGTAAAA-A
   Consensus (2401)  AG  C CGG  TGC  CA     A TC  CT  G A AG  AAA 2451                        2498
   pMamm C  (2335) CCCTGTCTCAAAAAAAAAAAAA--------------------------
Prostate GIP (2344) A--------AAAAAAAAAAAAAACTCGAGAAGCTTTGGACTTCTTCGCCA
   Consensus (2451)          AAAAAAAAAAA
```

TABLE 2

Prostate ECGI Homology

```
              1                                                  50
28SmRNA    (1) CTTTGGGAGGCCGAGGCCGTAGGATCCCTCGAGGAATCGCCTAACCCTGG
pMammB     (1) --------------------------------------------------
Prostate   (1) --------------------------------------------------
Hip55      (1) --------------------------------------------------

51                                                100
28SmRNA   (51) GGAGGTTGAGGTTGCAGTCACTGAGCCATAGTTGTGTCACTGTGCTCCAG
pMammB     (1) --------------------------------------------------
Prostate   (1) --------------------------------------------------
Hip55      (1) --------------------------------------------------

101                                               150
28SmRNA  (101) TCTGGGCGAAAGACAGAATGAGGCCCTGCCACAGGCAGGCAGGCAGGCAC
pMammB     (1) --------------------------------------------------
Prostate   (1) -------------------------------------------GCACGAG
Hip55      (1) --------------------------------------------------

151                                               200
28SmRNA  (151) GCAGGCAGAAAGACAACAGCTGTATTATGTTCTTCTCAGGGTAGGAAGCA
pMammB     (1) --------------------------------------------------
Prostate   (8) ATTCCCACTGTCCCTACCTACTATCCAGCGAAACCACAGCCAAGGGAACG
Hip55      (1) --------------------------------------------------

201                                               250
28SmRNA  (201) AAAATAACAGAATACAGCACTTAATTAATTTTTTTTTTTTTCCTTCGGACC
pMammB     (1) -----------------------------------------------CGG
Prostate  (58) GGCTTGGCGGAAT-CAGCGGGGAAAGAAGACCCTGTTGAGCTTGACTCTA
Hip55      (1) --------------------------------------------------

251                                               300
28SmRNA  (251) GAGTTTCACTCTTGGTGCCCACGCTGGAGTGCAGTGGCACCATCCTCGCT
pMammB     (4) CACGAGCAC----GGTGAAGAGACATGAGAGGTGTAGAATAAG-TGGGAG
Prostate (107) GTCTGGCAC----GGTGAAGAGACATGAGAGGTGTAGAATAAG-TGGGAG
Hip55      (1) --------------------------------------------------

301                                               350
28SmRNA  (301) CACCGCAAACCTCCACCTCCCGCGTTCAAGCGATTCTCCTGCCTCAGCCTC
pMammB    (49) GCCCCCGCGCCCCCC---CGGTGTCCCCGCGAGGGGCCCGCG----GGTC
Prostate (152) GCCCCCGCGCCCCCC---CGGTGTCCCCGCGAGGGGCCCGCGGGCGCGGTC
Hip55      (1) --------------------------------------------------

351                                               400
28SmRNA  (351) CTGAGTAGC--TGGGATTACAGGGAGGAGCCACCACACCCAGCTGATTTT
pMammB    (93) CGCCGGCCC-GCGGGC-GCCGGTGAAATACCACTACTCTGATCGTTTTTT
Prostate (200) CGCCGGCCCTGCGGGCCGCCGGTGAAATACCACTACTCTGATCGTTTTTT
Hip55      (1) --------------------------------------------------

401                                               450
28SmRNA  (399) GTATTGTTAGTAGAGACGGCATTTCTCCATGTGGTCAGGCTGGTCTCGA
pMammB   (141) CACTGACCCGGTGA-GCGCGGGGC-----GACCCCCGAGGGCTCTCGA
Prostate (250) CACTGACCCGGTGA-GCGCGGGGGC-----GACCCCCGAGGGCTCTCGC
Hip55      (1) ------------ATCGCCGCGAACCT----AGCCGGAACGGGCCAGGCC 451                                               500
28SmRNA  (449) A-CTGCCGACCCCAGTCGATCTGCCCGCCCCCCCCCTCCCAAAATGCTTGG
pMammB   (185) TTCTGCC---CCAAGCG----------CCCGGCCGCCCGCC-GCCCGG
Prostate (295) TTCTGCGC---CCAAGCG----------CCCGGCCGCCCGCC-CCCGG
Hip55     (35) TGCAAGAG--GCCTACC-----------TGCCGGTGGTCACCGACAAGTC 501                                               550
28SmRNA  (498) -GTGCCCAGCGGTGAGCCATCGTCGACTGGCCGGCTACGTTTATCTATTCAT
pMammB   (221) CCCGAGCCCGCTCCGGGACAGTGCC--AGTCGGGGGTTTCACCGGGC---
Prostate (331) CCGCGACCGCTCCGGGACAGTGCCC-AGTCGGGGGTTTCACCGGGC---
Hip55     (72) CCGCGCCCGAGTGGCTCTCTTCGTTCACGTATGAAGCCACAGCGATGACAT--

551                                               600
28SmRNA  (547) TTTCTTAATTCATTTTACTTCTTTTTTAGTGTTCCGATTTTAATCTATTCATT
pMammB   (266) CGGTACACCTGTCAACGGTAACGCACGCTGTCG---TAAGGCCAGCCAG
Prostate (377) CGGTACACCTGTCAA-CGGTAACGCACGCTGTCC---TAAGGCAGCCAG
Hip55    (120) CCGCGTGGCTGGCACAGGGGAG----GCGGGG---TGGAG-GAGATGGT 601                                               650
28SmRNA  (597) TATTTCACATTTATTCATTTATTTATTTATTTACTTATTTATTTATTTCG
pMammB   (313) GGAGGACA--AA-CCTCCCGTGGAGCAGAAGGGCAAAA-------TGATCT
Prostate (424) GGAGGACAGAAACCTCCCGTGGAGCAGAAGGGCAAAAGCTCGCTTGATCT
Hip55    (162) GGAGGAGCTCAAC---------AGCGGAAGC------------TGAGCT
```

TABLE 2-continued

Prostate ECGI Homology

```
                  651                                              700
28SmRNA   (647)   AGACAGAGTCTCGCTCCGCTCCCCAGCCTGGAGTCAGGGGCGTGATC--
pMammB    (355)   TGATTTTCAGTACGAATACAAACGGTGAAAGCGGG---CCCTCA-GATC-T
Prostate  (474)   TGATTTTCAGTACGAATACAAACGGTGAAAGCGGG---CCCTCACGATCCT
Hip55     (191)   ACGCCTTCTGCA-GAGCGAACGAGACCCCAACTCTGC---ACTGCCCAAA- 701                                              750
28SmRNA   (695)   TCGGCTCAC-TGCAACGTCCGCCTCCCCGGTCGCACGCCATTCTCCTGCCT
pMammB    (401)   TCTCACCTTTTGGGTTTTA-AGCAGGAGGTGTCAGAAAAGT----TACCA
Prostate  (522)   TCTCACCTTTTGGGTTTTA-AGCAGGAGGTGTCAGAAAAGT----TACCA
Hip55     (235)   CTTCTGCTCACAACTGGACAGGCGAGGCCGGAACGATC----GCGGA 751                                              800
28SmRNA   (744)   CGGCCTCCCAAGTAGGCTGGGACTACAGGCGCCCGCCACCGTGCCCGGCTA
pMammB    (446)   CAGGGAT--AACTGGCTTGT------GCGGCCA-AGCGTTCAAAGCGA
Prostate  (567)   CAGGGAT--AACTGGCTTGT------GCGGCCA-AGCGTTGATAGCGA
Hip55     (281)   -ACGGA--------CTGT------GCGAGGCA-CG---TGA-GGAC 801                                              850
28SmRNA   (794)   ACTTTTTGTATTTCGAGTAGAGATGCCGTTTCACTGTGGTAGCCAGGATG
pMammB    (486)   CGTCGCTTTTGACCTTCGATGTCGGCTCTTCCTATCATGCGAAG---
Prostate  (607)   CGTCGCTTTTGACCTTCGATGTCGGCTCTTCCTATCATGTGAAG---
Hip55     (309)   CATGGCCAGCT--GCCT--AAGGGCGCCATGTGACCATCA--ACG---

851                                              900
28SmRNA   (844)   GTGTGCATCTCCTGACCCCGTGATCCGCCCACCGTCGGCCTCCCAGG---G
pMammB    (533)   --CA-GAATTCACCAAGCGTTGGATTGGTCACCCACTAATAGGGAACGTG
Prostate  (654)   --CA-GAATTCACCAAGCGTTGGATTGGTCACCCACTAATAGGGAACGTG
Hip55     (350)   --GACGGCCGAGGAGGATGTCGAGCCTGAGTGCA-TGATGCACAAGCTG 901                                              950
28SmRNA   (891)   TCGTGCGGAGG--ACAGGCGTCAGCCACC--GGCCCCGGCGCTA----TTTAT
pMammB    (580)   AGCTGGCTTCTAGACCGTCCTGAGACAGGTTTTGT-TTACCCTACTGATGAT
Prostate  (701)   AGCTGGGATTAGACCGTCCTGAGACAGGTTAGTTTTACCCTACTGATCAT
Hip55     (397)   GCGAAGGCGT--------CAGGTGCGGAACTACAGCTTTCACAG--GGACGG 951                                              1000
28SmRNA   (934)   CTATTAGTAACTTTGAGTCCAGGT----TATG-AAACCAGT--TAGTTTT
pMammB    (629)   GTGTTGTGCCATGGTAATCCTGCTCAGTACG-AGAGGAACGCAGGTT
Prostate  (751)   GTGTTGTGCCATGGTAATCCTGCTCAGTACG-AGAGGAACGCAGGTTC
Hip55     (438)   TGGCCGCTTCCAGGACGTGGGACCCCAGCGCCCGGTGGGCTCTGTGTACC 1001                                             1050
28SmRNA   (934)   TGTAATTTTTTTTTTTTTTTTTTTGAGACGAGGTTTCACCGTGTT
pMammB    (629)   AGACATTTGGTGTAGTG-CTTGCCTGGGAGCCAATGG--GGCGAACGT
Prostate  (751)   AGACATTTGGTGTAGTG-CTTGCCTGGGAGCCAATGG--GGCGAACGT
Hip55     (438)   AGAA----GACCAATGC--CGGCGTCTGAGATTAAAGGGTTGCTAAAGAC 1051                                             1100
28SmRNA   (1028)  GCCAAGGCTTGCAC---CGAGGGATCCACCGGCCCTGCCCTCCAAAAGT
pMammB    (725)   ACCATCTGTGGCATTATTACTGAACGCCTCTAAGTCAAATCCCGCCCAG
Prostate  (847)   ACCATCTGTGGCATTATGACTGAACGCCTCTAAGTCAAATCCCGCCCAG
Hip55     (532)   AGCGTCTGGGCCGA-AGCAGAGTAGGAGG---AGG-AGAAGGGTCGCCTG 1101                                             1150
28SmRNA   (1076)  CGCGGGATGCCAGGCGCGAGGGTAGCGCCCT-GCGA--CGCCCCCTTTCC
pMammB    (775)   GCGGA-ACGATACGGCACGCGC-CGGACCCTCGGTTGGCGCTGGATCGC
Prostate  (897)   GCGGA-ACGATACGGCACGCGC-CGGACCCTCGGTTGGCGCTGGATAGC
Hip55     (577)   AGGTA-G---AAGCGGCGG-GGGC-AGGAAGGCAGAGC-GGGAGCTGG-AGG 1151                                             1200
28SmRNA   (1123)  CCTTCGCCGCTTGTCTTC-GCGATAGAG---AGTTTCACGGCAGAGCTT
pMammB    (823)   CGGTCCCCCGCCTGTCCCGCCGCGGGCGCCCCCCCCCTCACGCGCC
Prostate  (945)   CGGTCCCCCCCTGTCCCGCCGCGGGGCGCGCCCCCCCTCCAGCGCCC
Hip55     (620)   AGCAGGGCGGGAGCGTGAGCTGCGTCA-GGCTGCAGCGCCGGAGGAGC 1201                                             1250
28SmRNA   (1170)  TGGCTGGCGTGCCTTAAACTGATTCTAAATAGAAATTTCCCAGC----GTCA
pMammB    (873)   CCGCGCGCCCGGAGGGCGCGTGCCCCGCCGCGCGCCGGACGGGTCC
Prostate  (994)   CCGCGCGCCCGGAGGGCGCGTGCCCCGCCGCGCGCCGGACGGGTCC
Hip55     (668)   GCTATCAGCAGCAGGTGGCGAGGCCAGCCCCAGA--GGGTGGGAGC 1251                                             1300
28SmRNA   (1216)  GCTTGTG----GCCTCAGGGATCTGAGCGGAGGAGTCCCTG----GTGTG
pMammB    (923)   GGTGCGGAGTGCCCTTCGTCCTGGCAAACGGGGCCGGCCGAAAGGCGG
Prostate  (1044)  GGTGCGGAGTGCCCTTCGTCCTGGAAACGGGGCCGGCCGAAAGGCGG
Hip55     (716)   AG--GAGCAAGAAGTGGTTTCAAGGAACGCAAATGAG-CAGCA--GTTT
```

TABLE 2-continued

Prostate ECGI Homology

```
               1301                                              1350
28SmRNA (1260) TCTATCAGAGGACCCTACGCGTAAGCAGGAGAAAAATCGTAAGCTCAAA
pMammB  ( 973) CCGCCCCTCCCCCGT-CACGCACCG-CACGTTCGTGCT---CGTGCCGA
Prostate(1094) CCGCCCCTCCCCCGT-CACGCACCG-CACGTTCGTGGGAACCTGGCGC
Hip55   ( 761) CCGTGCAGCCAGGCA-GATTTTCAA-GCAGAAGGAGAGGGCAGTGC- 1351                                              1400
28SmRNA (1310) GTCAGTCCTTTTGTGATACAGAAATACACGGATTCACCCAAAACACAGAA
pMammB  (1018) ATTCGGCACGAGTAGCACCATTCACAATAGA---GATACAGTGCATTCTA
Prostate(1142) -TAAACCCCTCCATCTCCAGTCCTCA--GC---CTGGCAGCTGAGCAG
Hip55   ( 808) ----ACCCCCTCCATCTCAGTCCTCA--GC---CTGCAAGCTGAGCAG 1401                                              1450
28SmRNA (1360) AGCAGCCTTTAGAAATGGCC TCGCCCTGGTGTGGTGCCACTCCTTCT
pMammB  (1065) TGT-TTATTATATAA------GAATTCTTTT--CCTTTGGGCAGATA--
Prostate(1186) CCCTTCCTGCAGAA------GCAGCTCAC----CCAACC---AGAGA--
Hip55   ( 849) CCCTTCCTGCAGAA------GCAGCTCAC----CCAACC---AGAGA--

1451                                              1500
28SmRNA (1410) TTTGGCTTGGACCTTGACTCAGAGGATTCCCAGTCGGTCCTTCTCTCT
pMammB  (1104) -TCCAGTAGTGGGATTCCTAGATCACCTGGTAGTTCTATTTCTGCTTTAT
Prostate(1221) -CCCACTC-------TTGCAGAGAGCCAGCTGCTGCCATCTCAAGGCCA
Hip55   ( 884) -CCCACTC-------TTGCAAGAGCCAGCTGCTGCCATCTCAAAGGCCA 1501                                              1550
28SmRNA (1460) GCACGGCAGCTTCAGAGCCTCCGATGGCTGGCCACTTAGGCTGCGTCC
pMammB  (1153) TGAGAAATCTTCATACTGATTTCCATAGGTTGTACAAATTTACATTCC
Prostate(1263) GGGCAGATCTCCCTGCTGAG--------GAGCCGCGCC------CAGCAC
Hip55   ( 926) GGGCAGATCTCCCTGCAAG--------AGCCGCGCC------AGCAG 1551                                              1600
28SmRNA (1510) CCCAGGAGCCCTGGCCGATTAGTTGTGGCATCCCTTCGAGGGCGCGGT
pMammB  (1203) TACCAAGTCATTTTTTTA--AATATGAAAGAATGGTCTCGAGAAAT----
Prostate(1300) TCCTCCATGTCTGGTGCA---GGCAGAAGAGGAGCCTGTGTATGAG-----
Hip55   ( 963) TCCTCCATGTCTGGTGCA---GGCAGAAGAGGAGCCTGTGTATGAG-----

1601                                              1650
28SmRNA (1560) CACCAGTGTGCTGTGGCAGC--CTCCATCCTCCCCCACCCCTCCCC
pMammB  (1247) GCCCGTCATTAGTATCCCCCTTTACCTCTCTACTGCAGAGATGCTTGA
Prostate(1343) GAACCTCCAGAGCAGGAC------ACCT-TCTAC----GAGCAGCCCCA
Hip55   (1006) GAACTCCAGAGCAGGAC------ACT-TCAG----GAGCAGCCCCA 1651                                              1700
28SmRNA (1608) AGGGGGATCCCAATTCATTCGGCCTGACACGCTCACTGGGAGGCGCCCG
pMammB  (1297) GGGGTA-----CAGGTATTTACAAGTCT-CATTAC-ACAGACA---AATCA
Prostate(1382) CTGGTG----CAGCAG----GAAGCTG-CTGGCT-CTGAGCA--CATTCA
Hip55   (1045) CTGGTG----CAGCAG----GAAGCTG-CCGGCT-CTGAGCA--CATTCA 1701                                              1750
28SmRNA (1658) GCATCACCTAGCGGTCCTGTTACTCTGAAAACGGACCCTCCACAGAGGA
pMammB  (1339) ATATTGAAATTTCTGCATTAG-AGGCACGCATTTTAGGATTCAAAGTTGT
Prostate(1420) CCA--------CCACATTCA-GGGCCCC------GGGCTCA--GT---
Hip55   (1083) CCA--------CCACATTCA-GGGCCAG------GGGCTCA--GT---

1751                                              1800
28SmRNA (1708) AGGGAGCACCACCCGCCTCGCGACACCCTGGGCAACTGTGTCCTCTCC
pMammB  (1388) A----AGAACAAGGACAAGTGGTCTAGGGACTTCAAAACCTGCAACTGAA
Prostate(1448) -----------GGCAAGGCGTTCTGTCCCCGTGCCCTGTACGACTACCAG
Hip55   (1111) -----------GGCAAGGCGTTCTGTCCCCGTGCCCTGTACGACTACCAG 1801                                              1850
28SmRNA (1758) ACCGCCCCGCC-CCCACCTCCAAGTTCCTCCCTCCCTTGCTGCCTAGCA
pMammB  (1435) ATCTCAGAACAAATACATTTCTAGTAGTACCACCAGCATAATTCTACTG
Prostate(1487) GCAGCCGACGCACACAGCAGATCCCTTTGACCCCGACAACCTCATCACGGG
Hip55   (1150) GCAGCCGACGCACACAGCAGATCCCTTTGACCCCGACAACCCATCACGGG 1851                                              1900
28SmRNA (1807) AGCGCCCACTTCGCGACGGGGTCTGATTGACCTTTGATCAGGCAAAAC
pMammB  (1485) AACTGGCTTCTGATCATCATTTACCTACTTATT---------AAAAC
Prostate(1537) CATCGAG---CTGATCGACGAAGCCTGCTGGGCCTGG---------CTATG
Hip55   (1200) CCTCGAG---GCCATCGAGGAAGCCTGGCGCCGTGG---------CTCTG 1901                                              1950
28SmRNA (1857) GAACAAACAGATAAATAAATCAAATAAGACAAGAGCCACTAACCT-AAGTA
pMammB  (1526) TAATGAAAAGGGTTTATATCAAATATAGCTTAAGGTAAAAAATCAAATT
Prostate(1575) GGCCGGATGGCCATTTTGGCTGTTCCGTGCCACTCGTGGAGCTCATT
Hip55   (1238) GGCCGGATGCCCATTTTGGCTGTTCCTGCCACTCGTGGAGCTCATT
```

TABLE 2-continued

Prostate ECGI Homology

```
                      1951                                              2000
28SmRNA   (1906)  AAATAXGTCAAXACAACXCATTAXAATACAATAAGATAXGATACGATXGG
pMammB    (1576)  ATAGGXAAAGCTGTTTTCTTTTGCATTTTAAT----TTCAAAACAAAAA
Prostate  (1625)  GAGTGAC--GCXGAGGGCA-CATC-TTGCCCT----TCCCTCTCAGACA
Hip55     (1288)  GAGTGAC--GCXGAGGGXGGCCXX-TACACTA----GTXTAGAGAXAXAA 2001                                              2050
28SmRNA   (1956)  ATGCGATAGGATACGATAGGATACAATACAATAGGATACGATACAATACA
pMammB    (1622)  TAGCTACCGTCTAT--TGGGCATTTATACTGTACCAGACACTGTGTTTGT
Prostate  (1667)  TGCCTTCCTTAT---------------TGCTGGAAGAGGAGGCCTGGGAGT
Hip55     (1331)  C-------------------------------------------------

2051                                              2100
28SmRNA   (2006)  ATACAATACAATACAATACAATACAATACAATACAATACAATACAATACA
pMammB    (1670)  -CACATTTCAAAAATGTTCTC-ATGGTAATGTTCA----CAATA------A
Prostate  (1703)  -TGACATTCAGCACTCTTCCA-GGAATAGGACCCC---CAGTG------A
Hip55     (1332)  --------------------------------------------------

2101                                              2150
28SmRNA   (2056)  ATACGCCGGGCGCGGTGGCTCATGCCTGTCATCCCGTCACTTTGGGATGC
pMammB    (1709)  TTCTGTAGGGTGAGAA--------------ATAGTCTTACCGTAGTAAGA
Prostate  (1742)  GGATG-AGCCCTCAGGG--------------CTCCCTCCGGCTTGGCAGAC
Hip55     (1332)  --------------------------------------------------

2151                                              2200
28SmRNA   (2106)  CGAGGTGGACGCATCACCT--GAAGTCGGGAGTTGGAGACAAGCCCGACC
pMammB    (1746)  CTATT_AGAAACGAAACCTCTGAACCTTGGAGTTCAACTTGCCCAA-AGT
Prostate  (1778)  TCAGCCTCTCACCCCAAAT--GCAGCAATGGCCTGGTGATTCCCAC-ACA
Hip55     (1332)  --------------------------------------------------

2201                                              2250
28SmRNA   (2154)  AACATGGAGAAATCCCGTCTCAATTGAAAATACAAAACTAGCCGGGCGCG
pMammB    (1795)  TAGTAACAGGACTAGGACTTGAACCCTGAACCATCACACT---CCAGATCT
Prostate  (1825)  TCCTTCCTGCATCCCCCGACCCTCCCAGACAGCTTGGCT---CTTGGCCC
Hip55     (1332)  --------------------------------------------------

2251                                              2300
28SmRNA   (2204)  GTGGCACATGCCTATAATCCCAGCTGCTAGGAAGGCTGAGGCAGGAGAAT
pMammB    (1842)  CT----CCATACC-ACACTGCTAGCACAT------CTGCCTCTCATCTTATT
Prostate  (1872)  TG----ACAGGAT-ACTGAGCCAAGCCCT------GCCTGTGGGCAAGCCCT
Hip55     (1332)  --------------------------------------------------

2301                                              2350
28SmRNA   (2254)  CGCTTGAACCTGGGAAGCGGAGGTTGCAGTGAGCCGAGATTGCGCCACTG
pMammB    (1883)  CCTGGCTCCCTKYTTATTTCCT-TTCCCTTCCTCCCACAACCCCTTTTTC
Prostate  (1913)  GAGTGCCCACTGCCAAGCTGCC-GGGAAGGGTCCTGAGCAGGGCCATCTG
Hip55     (1332)  --------------------------------------------------

2351                                              2400
28SmRNA   (2304)  CACTCCAGTCTGAGCAACAAGAGCGAAACTCCGTCTCAAAAATAAATACA
pMammB    (1932)  CCCCCATTTCTTTTCT-----------TCTTTTTATTTGTTAATTACA
Prostate  (1962)  GGAGGCTCTGGCTGCC-----------TCTGCATTTATTTGCCTTTTT
Hip55     (1332)  --------------------------------------------------

2401                                              2450
28SmRNA   (2354)  TAAATAAATACATACATACATACATACATACATACATACATACATACATA
pMammB    (1970)  TAACTAA----------------------TACATCTTTATCAGAACA
Prostate  (2000)  TCTTTTT-------------------------CTCTTCCTTCTAAGGGT
Hip55     (1332)  --------------------------------------------------

2451                                              2500
28SmRNA   (2404)  AATTAAAATAAATAAATAAAATAAAATAAATGGGCCCTGCGCGCTG
pMammB    (1995)  ATTGATATAGCACAAAAGGATATAAAGTAC-----GGG---TGAGTGATA
Prostate  (2025)  GGTGCCACCACTGTTTAGAATGACCCTTG------GGA---ACAGTGAAC
Hip55     (1332)  --------------------------------------------------

2501                                              2550
28SmRNA   (2454)  GCTCAAGCCTGTCATCCCCTCACTTTGGGAGGCCAA----GGCC-GTGG
pMammB    (2037)  GCTCATCCCTGTAATC-TAGCACTTTGAAGGCCAAGGCAGGCAGATCAC
Prostate  (2067)  GTAGAGAATTGTTTT-TAGCAGAGTTTGTGACCAA----AGTCAGAGTGG
Hip55     (1332)  --------------------------------------------------

2551                                              2600
28SmRNA   (2499)  ATCAAGAGGCGGTC-AGACCAACAGGGCCAGTATGGTGAAACCCCGTCTC
pMammB    (2086)  TTGATCCAGAGTTCGAGACCAGCCTGGCCAACATGGTGAAACCCTGTCTC
Prostate  (2112)  ATCATGGTC-GTTTGCAGCAGGGAATTTGTCTTGTTCGAGCCTGCTCTG
Hip55     (1332)  --------------------------------------------------
```

TABLE 2-continued

Prostate ECGI Homology

```
                 2601                                              2650
28SmRNA  (2548)  TACTCAC-AATACACAACATTAGCCGGGCGCTGTGCTGTGCTGTACTGTC
pMammB   (2136)  TACAAAAAATACAAAAATTTAGCCGGGCGTGCTG-----GCACAC--ACC
Prostate (2161)  TGCTCCCCACTCCATTTCTCTGTCCCTCTGCCTGG----GCTATG--GGA
Hip55    (1332)  --------------------------------------------------

2651                                              2700
28SmRNA  (2597)  TGTAATCCCAGCTACTCGGGAGGCCGAGCTGAGGCAGGAGAATCGCTTGA
pMammB   (2180)  TGTAGTCTCAGCTACTCTGAGGGCTGAGGTG------GGAAGATTGATTGA
Prostate (2205)  AGTGGGGATGCAGATGGCCAAGCTCCCACCC-----TGGGTATTCAAAAA
Hip55    (1332)  --------------------------------------------------

2701                                              2750
28SmRNA  (2647)  ACCTGGGAGGCGGAGGTTGC----AGTGAGCCGAGATCGCGCCACTGCAAC
pMammB   (2225)  GCCCAGGAGGTGGAAGCTGCAGCAGTGCGCTGAGATTGCGCCATTGCACT
Prostate (2250)  CGGCAGACACAACATGTTCCTCCACGCGGCTCACTCGATGCC--TGCAGG
Hip55    (1332)  --------------------------------------------------

2751                                              2800
28SmRNA  (2694)  CCAGCCTGGGCGACAGAGCGAGACTCCGTCTCCAAAAAATGAAAATGAAA
pMammB   (2275)  CCAGCCTGGGTGAGAGAGAGAGACCCTGTCTTCAAAAAAAAAAAAAAAAA
Prostate (2298)  CCCCAGTGTGTCCCTCA-ACTGATTCTGACTTCAGGAAAAGTAAAAAAAA
Hip55    (1332)  --------------------------------------------------

2801                                              2850
28SmRNA  (2744)  ATGAAACGCAACAAAATAATTAAAAAGTGAGTTTCTGGGGAAAAAGAAGA
pMammB   (2325)  AA------------------------------------------------
Prostate (2347)  AAAAAAAAAAACTCGAGAAGCTTTGGACTTCTTCGCCA-------------
Hip55    (1332)  --------------------------------------------------

2851                                              2900
28SmRNA  (2794)  AAAGAAAAAGAAAAAAACAACAAAACAGAACAACCCCACCGTGACATAC
pMammB   (2327)  --------------------------------------------------
Prostate (2384)  --------------------------------------------------
Hip55    (1332)  --------------------------------------------------

2901                                              2950
```

TABLE 3

Putative Prostate ECGI Amino Acid Sequence

```
         H   E   I   P   T   V   P   T   Y   Y   P   A   K   P   Q
  1  GCACGAGATT CCCACTGTCC CTACCTACTA TCCAGCGAAA CCACAGCCAA
     CGTGCTCTAA GGGTGACAGG GATGGATGAT AGGTCGCTTT GGTGTCGGTT
       . E   R   A   W   R   N   Q   R   G   K   K   T   L   L   S
 51  GGGAACGGGC TTGGCGGAAT CAGCGGGGAA AGAAGACCCT GTTGAGCTTG
     CCCTTGCCCG AACCGCCTTA GTCGCCCCTT TCTTCTGGGA CAACTCGAAC
       T   L   V   W   H   G   E   E   T   *   E   V   *   N   K   W
101  ACTCTAGTCT GGCACGGTGA AGAGACATGA GAGGTGTAGA ATAAGTGGGA
     TGAGATCAGA CCGTGCCACT TCTCTGTACT CTCCACATCT TATTCACCCT
       . A   P   G   A   P   P   V   S   P   R   G   A   R   G   G
151  GGCCCCCGGC GCCCCCCCGG TGTCCCCGCG AGGGGCCCGG GGCGGGGTCC
     CCGGGGGCCG CGGGGGGGCC ACAGGGGCGC TCCCCGGGCC CCGCCCCAGG
       . R   P   C   G   P   P   V   K   Y   H   Y   S   D   R   F
201  GCCGGCCCTG CGGGCCGCCG GTGAAATACC ACTACTCTGA TCGTTTTTTC
     CGGCCGGGAC GCCCGGCGGC CACTTTATGG TGATGAGACT AGCAAAAAAG
       T   D   P   V   R   R   G   E   P   R   G   A   L   A   S
251  ACTGACCCGG TGAGGCGGGG GGGCGAGCCC CGAGGGGCTC TCGCTTCTGG
     TGACTGGGCC ACTCCGCCCC CCCGCTCGGG GCTCCCCGAG AGCGAAGACC
       . A   K   R   P   A   A   R   R   P   G   A   T   R   S   G
301  CGCCAAGCGC CCGGCCGCGC GCCGGCCGGG CGCGACCCGC TCCGGGACA
     GCGGTTCGCG GGCCGGCGCG CGGCCGGCCC GCGCTGGGCG AGGCCCTGT
       . A   R   W   G   V   *   L   G   R   Y   T   C   Q   T   V
351  GTGCCAGGTG GGGAGTTTGA CTGGGGCGGT ACACCTGTCA AACGGTAACG
     CACGGTCCAC CCCTCAAACT GACCCCGCCA TGTGGACAGT TTGCCATTGC
       Q   V   S   *   G   E   L   R   E   D   R   N   L   P   W   S
401  CAGGTGTCCT AAGGCGAGCT CAGGGAGGAC AGAAACCTCC CGTGGAGCAG
     GTCCACAGGA TTCCGCTCGA GTCCCTCCTG TCTTTGGAGG GCACCTCGTC
       . R   A   K   A   R   L   I   L   I   F   S   T   N   T   D
451  AAGGGCAAAA GCTCGCTTGA TCTTGATTTT CAGTACGAAT ACAGACCGTG
     TTCCCGTTTT CGAGCGAACT AGAACTAAAA GTCATGCTTA TGTCTGGCAC
       . S   G   A   S   R   S   F   *   P   F   G   F   *   A   G
501  AAAGCGGGGC CTCACGATCC TTCTGACCTT TTGGGTTTTA AGCAGGAGGT
     TTTCGCCCCG GAGTGCTAGG AAGACTGGAA AACCCAAAAT TCGTCCTCCA
         V   R   K   V   T   T   G   I   T   G   L   W   R   P   S   V
```

TABLE 3-continued

Putative Prostate ECGI Amino Acid Sequence

```
 551 GTCAGAAAAG TTACCACAGG GATAACTGGC TTGTGGCGGC CAAGCGTTCA
     CAGTCTTTTC AATGGTGTCC CTATTGACCG AACACCGCCG GTTCGCAAGT
     . S  D  V    A  F  *    S  F  D  V   G  S  S      Y  H
 601 TAGCGACGTC GCTTTTTGAT CCTTCGATGT CGGCTCTTCC TATCATTGTG
     ATCGCTGCAG CGAAAAACTA GGAAGCTACA GCCGAGAAGG ATAGTAACAC
     . A  E  F    T  K  R    W  I  V  H   P  L  I      G  N
 651 AAGCAGAATT CACCAAGCGT TGGATTGTTC ACCCACTAAT AGGGAACGTG
     TTCGTCTTAA GTGGTTCGCA ACCTAACAAG TGGGTGATTA TCCCTTGCAC
       S  W  D  *  T  V  V    R  Q  V   S  F  T     L  M
 701 AGCTGGGATT AGACCGTCGT GAGACAGGTT AGTTTTACCC TACTGATGAT
     TCGACCCTAA TCTGGCAGCA CTCTGTCCAA TCAAAATGGG ATGACTACTA
     . C  C  C    H  G  N  P    A  Q  Y   E  R  N     R  R
 751 GTGTTGTTGC CATGGTAATC CTGCTCAGTA CGAGAGGAAC CGCAGGTTCA
     CACAACAACG GTACCATTAG GACGAGTCAT GCTCTCCTTG GCGTCCAAGT
     . H  L  V    Y  V  L    G  *  G    A  N  G  A     K  L
 801 GACATTTGGT GTATGTGCTT GGCTGAGGAG CCAATGGGGC GAAGCTACCA
     CTGTAAACCA CATACACGAA CCGACTCCTC GGTTACCCCG CTTCGATGGT
       S  V  G  L   *  L  N    A  S  K    S  E  S  R    P  G
 851 TCTGTGGGAT TATGACTGAA CGCCTCTAAG TCAGAATCCC GCCCAGGCGG
     AGACACCCTA ATACTGACTT GCGGAGATTC AGTCTTAGGG CGGGTCCGCC
     . T  I  R    Q  R  R  G    A  S  V    G  L  G    *  P
 901 AACGATACGG CAGCGCCGCG GAGCCTCGGT TGGCCTCGGA TAGCCGGTCC
     TTGCTATGCC GTCGCGGCGC CTCGGAGCCA ACCGGAGCCT ATCGGCCAGG
     . R  L  S    P  P  A    G  R  P  P     L  H  A    P  R
 951 CCCGCCTGTC CCCGCCGGCG GGCCGCCCCC CCCTCCACGC GCCCCGCGCG
     GGGCGGACAG GGGCGGCCGC CCGGCGGGGG GGGAGGTGCG CGGGGCGCGC
       R  G  R  A   R  A  P    P  R  A    G  T  G  V    R  C
1001 CGCGGGAGGG CGCGTGCCCC GCCGCGCGCC GGGACCGGGG TCCGGTGCGG
     GCGCCCTCCC GCGCACGGGG CGGCGCGCGG CCCTGGCCCC AGGCCACGCC
     . V  P  F    V  L  G  N    G  A  R    P  E  R    R  P
1051 AGTGCCCTTC GTCCTGGGAA ACGGGGCGCG GCCGGAAAGG CGGCCGCCCC
     TCACGGGAAG CAGGACCCTT TGCCCCGCGC CGGCCTTTCC GCCGGCGGGG
     . R  P  S    R  T  A    R  S  W  G    T  W  R       T
1101 CTCGCCCGTC ACGCACCGCA CGTTCGTGGG GAACCTGGCG CTAAACCACC
     GAGCGGGCAG TGCGTGGCGT GCAAGCACCC CTTGGACCGC GATTTGGTGG
       S  I  S  S    P  Q  P    G  K  L    R  S  P  F    L  Q
1151 TCCATCTCCA GTCCTCAGCC TGGCAAGCTG AGGAGCCCCT TCCTGCAGAA
     AGGTAGAGGT CAGGAGTCGG ACCGTTCGAC TCCTCGGGGA AGGACGTCTT
     . Q  L  T    Q  P  E  T    H  F  G    R  E  P     A  A
1201 GCAGCTCACC CAACCAGAGA CCCACTTTGG CAGAGAGCCA GCTGCTGCCA
     CGTCGAGTGG GTTGGTCTCT GGGTGAAACC GTCTCTCGGT CGACGACGGT
     . S  R  P    R  A  D    L  P  A  E    E  P  A    P  S
1251 TCTCAAGGCC CAGGGCAGAT CTCCCTGCTG AGGAGCCGGC GCCCAGCACT
     AGAGTTCCGG GTCCCGTCTA GAGGGACGAC TCCTCGGCCG CGGGTCGTGA
       P  P  C  L   V  Q  A    E  E  E    A  V  Y  E    E  P
1301 CCTCCATGTC TGGTGCAGGC AGAAGAGGAG GCTGTGTATG AGGAACCTCC
     GGAGGTACAG ACCACGTCCG TCTTCTCCTC CGACACATAC TCCTTGGAGG
     . E  Q  E    T  F  Y  E    Q  P  P    L  V  Q    Q  Q
1351 AGAGCAGGAG ACCTTCTACG AGCAGCCCCC ACTGGTGCAG CAGCAAGGTG
     TCTCGTCCTC TGGAAGATGC TCGTCGGGGG TGACCACGTC GTCGTTCCAC
     . G  S  E    H  I  D    H  H  I  Q    G  Q  G     L  S
1401 CTGGCTCTGA GCACATTGAC CACCACATTC AGGGCCAGGG GCTCAGTGGG
     GACCGAGACT CGTGTAACTG GTGGTGTAAG TCCCGGTCCC CGAGTCACCC
       Q  G  L  C   A  R  A  L   Y  D   Y  Q  A  A    D  D
1451 CAAGGGCTCT GTGCCCGTGC CCTGTACGAC TACCAGGCAG CCGACGACAC
     GTTCCCGAGA CACGGGCACG GGACATGCTG ATGGTCCGTC GGCTGCTGTG
     . E  I  S    F  D  P  E    N  L  I    T  G  I    E  V
1501 AGAGATCTCC TTTGACCCCG AGAACCTCAT CACGGGCATC GAGGTGATCG
     TCTCTAGAGG AAACTGGGGC TCTTGGAGTA GTGCCCGTAG CTCCACTAGC
     . E  G  W    R  G    Y  G  P  D    G  H  F     G  M
1551 ACGAAGGCTG GTGGCGTGGC TATGGGCCGG ATGGCCATTT GGCATGTTC
     TGCTTCCGAC CACCGCACCG ATACCCGGCC TACCGGTAAA CCGTACAAG
       P  A  N  Y   V  E  L    I  E  *    G  *  G  H    I  L
1601 CCTGCCAACT ACGTGGAGCT CATTGAGTGA GGCTGAGGGC ACATCTTGCC
     GGACGGTTGA TGCACCTCGA GTAACTCACT CCGACTCCCG TGTAGAACGG
     . F  P  S    Q  T  W  L    P  Y  C    W  K  R    R  P
1651 CTTCCCCTCT CAGACATGGC TTCCTTATTG CTGGAAGAGG AGGCCTGGGA
     GAAGGGGAGA GTCTGTACCG AAGGAATAAC GACCTTCTCC TCCGGACCCT
     .  *  H  S    A  L  F    Q  E  *  D   P  Q  *    G  *
1701 GTTGACATTC AGCACTCTTC CAGGAATAGG ACCCCCAGTG AGGATGAGGC
     CAACTGTAAG TCGTGAGAAG GTCCTTATCC TGGGGTCAC TCCTACTCCG
       L  R  A  P   S  G  L    A  D  S    A  C  H  P    K  C
1751 CTCAGGGCTC CCTCCGGCTT GGCAGACTCA GCCTGTCACC CCAAATGCAG
     GAGTCCCGAG GGAGGCCGAA CCGTCTGAGT CGGACAGTGG GGTTTACGTC
     . N  G  L    V  I  P  T    H  P  S    C  I  P    R  P
1801 CAATGGCCTG GTGATTCCA CACATCCTTC CTGCATCCCC GACCCTCCC
     GTTACCGGAC CACTAAGGGT GTGTAGGAAG GACGTAGGGG GCTGGGAGGG
```

TABLE 3-continued

Putative Prostate ECGI Amino Acid Sequence

```
          .  T    A    W    L    L    P    L    T    G    Y    *    A    K    P    C
1851 AGACAGCTTG GCTCTTGCCC CTGACAGGAT ACTGAGCCAA GCCCTGCCTG
     TCTGTCGAAC CGAGAACGGG GACTGTCCTA TGACTCGGTT CGGGACGGAC
          W    P    S    P    E    W    P    L    P    S    C    G    E    G    S    *
1901 TGGCCAAGCC CTGAGTGGCC ACTGCCAAGC TGCGGGGAAG GGTCCTGAGC
     ACCGGTTCGG GACTCACCGG TGACGGTTCG ACGCCCCTTC CCAGGACTCG
          .  G    G    S    G    R    L    W    ;    P    S    A    P    I    C    L
1951 AGGGGCATCT GGGAGGCTCT GGCTGCCTTC TGCATTTATT TGCCTTTTTT
     TCCCCGTAGA CCCTCCGAGA CCGACGGAAG ACGTAAATAA ACGGAAAAAA
          .  F    S    L    A    S    K    G    W    W    P    P    L    P    R    M
2001 CTTTTTCTCT TGCTTCTAAG GGGTGGTGGC CACCACTGTT TAGAATGACC
     GAAAAAGAGA ACGAAGATTC CCCACCACCG GTGGTGACAA ATCTTACTGG
          L    G    N    S    E    R    R    E    L    F    L    A    E    F    V    T
2051 CTTGGGAACA GTGAACGTAG AGAATTGTTT TTAGCAGAGT TTGTGACCAA
     GAACCCTTGT CACTTGCATC TCTTAACAAA AATCGTCTCA AACACTGGTT
          .  V    R    V    D    H    G    G    L    A    A    G    N    L    S    C
2101 AGTCAGAGTG GATCATGGTG GTTTGGCAGC AGGGAATTTG TCTTGTTGGA
     TCAGTCTCAC CTAGTACCAC CAAACCGTCG TCCCTTAAAC AGAACAACCT
          .  L    L    C    A    P    H    S    I    S    L    S    L    C    L    G
2151 GCCTGCTCTG TGCTCCCCAC TCCATTTCTC TGTCCCTCTG CCTGGGCTAT
     CGGACGAGAC ACGAGGGGTG AGGTAAAGAG ACAGGGAGC GGACCCGATA
          G    L    W    G    C    R    W    P    S    S    H    P    G    Y    S    K
2201 GGGAAGTGGG GATGCAGATG GCCAAGCTCC CACCCTGGGT ATTCAAAAAC
     CCCTTCACCC CTACGTCTAC CGGTTCGAGG GTGGGACCCA TAAGTTTTTG
          .  A    D    T    T    C    S    S    T    R    L    T    R    C    L    Q
2251 GGCAGACACA ACATGTTCCT CCACGCGGCT CACTCGATGC CTGCAGGCCC
     CCGTCTGTGT TGTACAAGGA GGTGCGCCGA GTGAGCTACG GACGTCCGGG
          .  V    C    A    S    T    D    S    D    F    R    K    S    S    K    D    K
2301 CAGTGTGTGC CTCAACTGAT TCTGACTTCA GGAAAAGTAA AAAAAAAAAA
     GTCACACACG GAGTTGACTA AGACTGAAGT CCTTTTCATT TTTTTTTTTT
          K    K    L    E    K    L    W    T    S    S             [SEQ ID NO: 9]
2351 AAAAAACTCG AGAAGCTTTG GACTTCTTCG CCA [SEQ ID NO: 4]
     TTTTTTGAGC TCTTCGAAAC CTGAAGAAGC GGT
```

TABLE 4

Putative MammC Amino Acid Sequence

```
          I    R    H    E    H    G    E    E    T    *    E    V    *    N    K
1    GAATTCGGCA CGAGCACGGT GAAGAGACAT GAGAGGTGTA GAATAAGTGG
     CTTAAGCCGT GCTCGTGCCA CTTCTCTGTA CTCTCCACAT CTTATTCACC
          E    A    P    G    A    P    P    V    S    P    R    G    A    R    G    G
51   GAGGCCCCCG GCGCCCCCCC GGTGTCCCCG CGAGGGGCCC GGGGCGGGGT
     CTCCGGGGGC CGCGGGGGGG CCACAGGGGC GCTCCCCGGG CCCCGCCCCA
          .  R    R    P    C    G    P    P    V    K    Y    H    Y    S    D    R
101  CCGCCGGCCC TGCGGGCCGC CGGTGAAATA CCACTACTCT GATCGTTTTT
     GGCGGCCGGG ACGCCCGGCG GCCACTTTAT GGTGATGAGA CTAGCAAAAA
          .  T    D    P    V    R    R    G    G    E    P    R    G    A    L    A
151  TCACTGACCC GGTGAGGCGG GGGGGCGAGC CCCGAGGGGC TCTCGCTTCT
     AGTGACTGGG CCACTCCGCC CCCCCGCTCG GGGCTCCCCG AGAGCGAAGA
          G    A    K    R    P    A    A    R    R    P    G    A    T    R    S    G
201  GGCGCCAAGC GCCCGGCCGC GCGCCGGCCG GGCGCGACCC GCTCCGGGGA
     CCGCGGTTCG CGGGCCGGCG CGCGGCCGGC CCGCGCTGGG CGAGGCCCCT
          .  S    A    R    W    G    V    *    L    G    R    Y    T    C    Q    T
251  CAGTGCCAGG TGGGGAGTTT GACTGGGCGG GTACACCTGT CAAACGGTAA
     GTCACGGTCC ACCCCTCAAA CTGACCCGC CATGTGGACA GTTTGCCATT
          .  Q    V    S    *    G    E    L    R    E    D    R    N    L    P    W
301  CGCAGGTGTC CTAAGGCGAG CTCAGGGAGG ACAGAAACCT CCCGTGGAGC
     GCGTCCACAG GATTCCGCTC GAGTCCCTCC TGTCTTTGGA GGGCACCTCG
          R    R    A    K    A    R    L    I    L    I    F    S    T    N    T    D
351  AGAAGGGCAA AAGCTCGCTT GATCTTGATT TTCAGTACGA ATACAGACCG
     TCTTCCCGTT TTCGAGCGAA CTAGAACTAA AAGTCATGCT TATGTCTGGC
          .  E    S    G    A    S    R    S    F    *    P    F    G    F    *    A
401  TGAAAGCGGG GCCTCACGAT CCTTCTGACC TTTTGGGTTT TAAGCAGGAG
     ACTTTCGCCC CGGAGTGCTA GGAAGACTGG AAAACCCAAA ATTCGTCCTC
          .  V    R    K    V    T    T    G    I    T    G    L    W    R    P    S
451  GTGTCAGAAA AGTTACCACA GGGATAACTG GCTTGTGGCG GCCAAGCGTT
     CACAGTCTTT TCAATGGTGT CCCTATTGAC CGAACACCGC CGGTTCGCAA
          H    S    D    V    A    F    *    S    F    D    V    G    S    S    Y    H
501  CATAGCGACG TCGCTTTTTG ATCCTTCGAT GTCGGCTCTT CCTATCATTG
     GTATCGCTGC AGCGAAAAAC TAGGAAGCTA CAGCCGAGAA GGATAGTAAC
          .  E    A    E    F    T    K    R    W    I    V    H    P    L    I    G
551  TGAAGCAGAA TTCACCAAGC GTTGGATTGT TCACCCACTA ATAGGGAACG
     ACTTCGTCTT AAGTGGTTCG CAACCTAACA AGTGGGTGAT TATCCCTTGC
```

TABLE 4-continued

Putative MammC Amino Acid Sequence

```
       .  S  W  V  *  T  V     V  R  Q  V     S  F  T     L  L
 601   TGAGCTGGGT TTAGACCGTC GTGAGACAGG TTAGTTTTAC CCTACTGATG
       ACTCGACCCA AATCTGGCAG CACTCTGTCC AATCAAAATG GGATGACTAC
        M  C  C     H  G  N     P  A  Q     Y  E  R  N     R  R
 651   ATGTGTTGTT GCCATGGTAA TCCTGCTCAG TACGAGAGGA ACCGCAGGTT
       TACACAACAA CGGTACCATT AGGACGAGTC ATGCTCTCCT TGGCGTCCAA
       .  R  H  L     V  Y  V  L     G  *     G  A  N  G     A  K
 701   CAGACATTTG GTGTATGTGC TTGGCTGAGG AGCCAATGGG GCGAAGCTAC
       GTCTGTAAAC CACATACACG AACCGACTCC TCGGTTACCC CGCTTCGATG
       .  S  V  G     L  *     L     N  A  S  K     S  E  S     R  P
 751   CATCTGTGGG ATTATGACTG AACGCCTCTA AGTCAGAATC CCGCCCAGGC
       GTAGACACCC TAATACTGAC TTGCGGAGAT TCAGTCTTAG GGCGGGTCCG
        G  T  I  R     Q  R  R     G  A  S     V  G  L  G     *  P
 801   GGAACGATAC GGCAGCGCCG CGGAGCCTCG GTTGGCCTCG GATAGCCGGT
       CCTTGCTATG CCGTCGCGGC GCCTCGGAGC CAACCGGAGC CTATCGGCCA
       .  P  R  L     S  P  P  A     G  R  P     P  P  S     T  R
 851   CCCCCGCCTG TCCCCGCCGG CGGGCCGCCC CCCCCCCTCC ACGCGCCCCG
       GGGGGCGGAC AGGGGCGGCC GCCCGGCGGG GGGGGGGAGG TGCGCGGGGC
       .  R  A  G     G  R  V     P  R  R  A     P  G  P     G  S
 901   CGCGCGCGGG AGGGCGCGTG CCCCGCCGCG CGCCGGGACC GGGGTCCGGT
       GCGCGCGCCC TCCCGCGCAC GGGGCGGCGC GCGGCCCTGG CCCCAGGCCA
        A  E  C  P     S  S  W     E  T  G     R  G  R  K     G  G
 951   GCGGAGTGCC CTTCGTCCTG GGAAACGGGG CGCGGCCGGA AAGGCGGCCG
       CGCCTCACGG GAAGCAGGAC CCTTTGCCCC GCGCCGGCCT TTCCGCCGGC
       .  P  L  A     R  H  A  P     H  V  R     A  R  A     E  F
1001   CCCCCTCGCC CGTCACGCAC CGCACGTTCG TGCTCGTGCC GAATTCGGCA
       GGGGGAGCGG GCAGTGCGTG GCGTGCAAGC ACGAGCACGG CTTAAGCCGT
       .  S  S  T     I  H  N     R  H  T  S     A  C     I  F  M
1051   CGAGTAGCAC CATTCACAAT AGACATACAA GTGCATGTAT CTTTATGATA
       GCTCATCGTG GTAAGTGTTA TCTGTATGTT CACGTACATA GAAATACTAT
        *  *     I  L     F  L  W     V  D  I     Q  *     W  D     C  *
1101   TAATGAATTC TTTTCCTTTG GGTAGATATC CAGTAGTGGG ATTGCTAGAT
       ATTACTTAAG AAAAGGAAAC CCATCTATAG GTCATCACCC TAACGATCTA
       .  T  W  *     F  Y  F  W     F  I  E     K  S  S     Y  *
1151   CACCTGGTAG TTCTATTTCT GGTTTATTGA GAAATCTTCA TACTGATTTC
       GTGGACCATC AAGATAAAGA CCAAATAACT CTTTAGAAGT ATGACTAAAG
       .  *  R  L     Y  K  F     T  S  L  P     S  D  F     F  K
1201   CATAGAGGTT GTACAAATTT ACATCCCTAC CAAGTGATTT TTTTAAATAT
       GTATCTCCAA CATGTTTAAA TGTAGGGATG GTTCACTAAA AAAATTTATA
        E  R  M  V     W  R  N     A  P  H     *  Y  P  P     F  T
1251   GAAAGAATGG TCTGGAGAAA TGCCCCTCAT TAGTATCCCC CTTTTACCTC
       CTTTCTTACC AGACCTCTTT ACGGGGAGTA ATCATAGGGG GAAAATGGAG
       .  L  L  Q     N  D  F  K     G  Y  R     Y  L  Q     V  S
1301   TCTACTGCAG AATGACTTCA AGGGGTACAG GTATTTACAA GTTTCATTAT
       AGATGACGTC TTACTGAAGT TCCCCATGTC CATAAATGTT CAAAGTAATA
       .  R  Q  I     E  Y  *     N  F  C  I     R  G  T     D  F
1351   ACAGACAAAT TGAATATTGA AATTTCTGCA TAAGAGGCAC AGATTTTAGG
       TGTCTGTTTA ACTTATAACT TTAAAGACGT ATTCTCCGTG TCTAAAATCC
        I  Q  S  C     M  N  K     D  K  C     S  R  D  L     Q  S
1401   ATTCAAAGTT GTATGAACAA GGACAAGTGC TCTAGGGACT TGCAAAGCTG
       TAAGTTTCAA CATACTTGTT CCTGTTCACG AGATCCCTGA ACGTTTCGAC
       .  N  W  K     S  Q  M  K     Y  I  S     S  S  T     T  S
1451   GAATTGGAAA TCTCAGATGA AATACATTTC TAGTAGTACC ACCAGCATAT
       CTTAACCTTT AGAGTCTACT TTATGTAAAG ATCATCATGG TGGTCGTATA
       .  S  T  E     L  A  L     *  S  S  L     I  P  T     Y  *
1501   ATTCTACTGA ATTGGCTTTG TGATCATCAT TAATACCTAC TTATTAAAAC
       TAAGATGACT TAACCGAAAC ACTAGTAGTA ATTATGGATG AATAATTTTG
        *  *  K  G     F  I  S     N  I  L     *  G  I  K     I  K
1551   TAATGAAAAG GGTTTATATC AAATATACTT TAAGGTATAA AAATCAAATT
       ATTACTTTTC CCAAATATAG TTTATATGAA ATTCCATATT TTTAGTTTAA
       .  *  V  K     L  F  S     L  A  F  *     F  Q  N     I  K
1601   ATAGGTAAAG CTGTTTTCTT TAGCATTTTA ATTTCAAAAC ATAAAATAGC
       TATCCATTTC GACAAAAGAA ATCGTAAAAT TAAAGTTTTG TATTTTATCG
       .  P  S  I     G  H  L     Y  C  T  R     H  C  V     C  H
1651   TACCGTCTAT TGGGCATTTA TACTGTACCA GACACTGTGT TTGTCACATT
       ATGGCAGATA ACCCGTAAAT ATGACATGGT CTGTGACACA AACAGTGTAA
        S  K  M  F     S  W  *     C  S  Q     *  F  C  R     V  R
1701   TCAAAAATGT TCTCATGGTA ATGTTCACAA TAATTCTGTA GGGTGAGAAA
       AGTTTTTACA AGAGTACCAT TACAAGTGTT ATTAAGACAT CCCACTCTTT
       .  S  L  T     V  V  R  L     F  S  K     R  N  L     *  T
1751   TAGTCTTACC GTAGTAAGAC TATTCAGTAA ACGAAACCTC TGAACCTTGG
       ATCAGAATGG CATCATTCTG ATAAGTCATT TGCTTTGGAG ACTTGGAACC
       .  F  N  L     R  K  V     S  N  R  T     R  T     *  T  *
1801   AGTTCAACTT GCGCAAAGTT AGTAACAGGA CTAGGACTTG AACCTGAACC
       TCAAGTTGAA CGCGTTTCAA TCATTGTCCT GATCCTGAAC TTGGACTTGG
        I  T  L  Q     I  S  P     Y  H  T     A  S  T  C     A  C
1851   ATCACACTCC AGATCTCTCC ATACCACACT GCTAGCACAT GTGCCTGTCA
```

TABLE 4-continued

Putative MammC Amino Acid Sequence

```
      TAGTGTGAGG TCTAGAGAGG TATGGTGTGA CGATCGTGTA CACGGACAGT
      . L   I   P   G   S   C   Y   F   P   F   Y   F   L   S   L
1901  TCTTATTCCT GGCTCCTGTT ATTTCCCTTT TTATTTCCTT TCCCTTCCTC
      AGAATAAGGA CCGAGGACAA TAAAGGGAAA AATAAAGGAA AGGGAAGGAG
      . T   T   P   F   S   P   H   F   F   S   F   F   L   I   V
1951  CCACAACCCC TTTTTCCCCC CATTTCTTTT CTTTCTTTTT AATTGTTAAT
      GGTGTTGGGG AAAAAGGGGG GTAAAGAAAA GAAAGAAAAA TTAACAATTA
      Y   I   T   N   T   C   L   S   E   Q   L   I   *   H   K   R
2001  TACATAACTA ATACATGCTT ATCAGAACAA TTGATATAGC ACAAAAGGAT
      ATGTATTGAT TATGTACGAA TAGTCTTGTT AACTATATCG TGTTTTCCTA
      . *   S   T   G   E   *   *   L   I   P   V   I   L   A   L
2051  ATAAAGTACG GGTGAGTGAT AGCTCATCCC TGTAATCCTA GCACTTTGGA
      TATTTCATGC CCACTCACTA TCGAGTAGGG ACATTAGGAT CGTGAAACCT
      . A   K   A   G   R   S   L   E   S   R   V   D   Q   P
2101  AGGCCAAGGC AGGCAGATCA CTTGAGTCCA GAGTTCGAGA CCAGCCTGGG
      TCCGGTTCCG TCCGTCTAGT GAACTCAGGT CTCAAGCTCT GGTCGGACCC
      Q   H   G   E   T   L   S   L   Q   K   N   T   K   I   *   P
2151  CAACATGGTG AAACCCTGTC TCTACAAAAA AATACAAAAA TTTAGCCGGG
      GTTGTACCAC TTTGGGACAG AGATGTTTTT TTATGTTTTT AAATCGGCCC
      . V   L   A   H   T   C   S   L   S   Y   S   E   G   *   G
2201  CGTGCTGGCA CACACCTGTA GTCTCAGCTA CTCTGAGGGC TGAGGTGGGA
      GCACGACCGT GTGTGGACAT CAGAGTCGAT GAGACTCCCG ACTCCACCCT
      . I   D   *   A   Q   E   V   E   A   A   V   R   *   D
2251  AGATTGATTG AGCCCAGGAG GTGGAAGCTG CAGCAGTGCG CTGAGATTGC
      TCTAACTAAC TCGGGTCCTC CACCTTCGAC GTCGTCACGC GACTCTAACG
      A   I   A   L   Q   P   G   *   E   R   E   T   L   S   Q   K
2301  GCCATTGCAC TCCAGCCTGG GTGAGAGAGA GAGACCCGT  CTCAAAAAAA
      CGGTAACGTG AGGTCGGACC CACTCTCTCT CTCTGGGACA GAGTTTTTTT
      . K
2351  AAAAA      [SEQ ID NO: 10]
      TTTTT      [SEQ ID NO: 3]
```

TABLE 5

Comparison MammA, MammB, MammC, Prostate

```
                 1                                                50
pMamm A    (1)  ----------------------------------------TGGGGCTC
pMamm B    (1)  --------------------------------------------------
pMamm C    (1)  --------------------------------------------------
  pPros    (1)  GCACGAGATTCCCACTGTCCCTACCTACTATCCAGCCGAAACCACAGCCAA 51                                               100
pMamm A    (9)  CACCCCGGTGGCGGCCGCTCTAGAACTAGTGGATCCCCCGGGCTGCAGGA
pMamm B    (1)  --------------------------------------------------
pMamm C    (1)  ------------------------------------------------GA
  pPros   (51)  GGGAACGGGCTTGGCGGAATCAGCGGGGAAAGAAGACCCTGTTGAGCTTG 101                                              150
pMamm A   (59)  ATTGGCACGAGAACGGTGAAGAGACATGAGAGGTGTAGAATCCGTGGCG
pMamm B    (1)  ---CGGCACGAGAACGGTGAAGAGACATGAGAGGTGTAGAATAAGTGGGA
pMamm C    (3)  ATTCGGCACGAGAACGGTGAAGAGACATGAGAGGTGTAGAATAAGTGGGA
  pPros  (101)  ACTAGTAGTGTGAGCGTGAAGAGACATCAGACCTGTAGAATAAGTGGGA 151                                              200
pMamm A  (109)  GGGCCCGGCGCCCCCCCGGTGTCCCCGCGAGGGGCTGGGGCG
pMamm B   (48)  GGGCCCGGCGCCCCCCCGGTGTCCCCGCGAGGGG----CGGTCG
pMamm C   (53)  GGGCCCGGCGCCCCCCCGGTGTCCCCGCGAGGGGCGGGCGGGTCG
  pPros  (151)  GGGCCCGGCGCCCCCCCGGTGTCCCCGCGAGGGGCGGGCGGGTCG 201                                              250
pMamm A  (159)  GCCGGCCTGCGGGGCCGGTGAAATACCACTACGCTATCGTTTTTT
pMamm B   (94)  GCCGGCC-GCGGGCCACCGGTGAAATACCACTACGCGATCGTTTTTT
pMamm C  (103)  GCCGGCCTGCGGGCCGGTGAAATACCACTACGCGATCGTTTTTT
  pPros  (201)  GCCGGCCTGCGGGCCGGTGAAATACCACTACGCGATCGTTTTTT 251                                              300
pMamm A  (209)  ACTGACCCGGCGACGGCCAGCCCCGAGGGGCTCTCGCTTCT
pMamm B  (142)  ACTGACCCGG-GAGGCGGGCGAGCCCCGAGGGGCTCTCGCTTCT
pMamm C  (153)  ACTGACCCGGCCAGGCCAGGGGCGAGCCCCGAGGGGCTCTCGCTTCT
  pPros  (251)  ACTGACCCGGCCAGGCCAGGGGCGAGCCCCGAGGGGCTCTCGCTTCT
```

TABLE 5-continued

Comparison
MammA, MammB, MammC, Prostate

```
                  301                                                350
pMamm A  (259)   ...
pMamm B  (191)   ...
pMamm C  (203)   ...
pPros    (301)   ...

351                                                400
pMamm A  (309)   GTGCCAG G GGGAGTTTGACTGGGGCGGTACACCTGTCAAACGGTAA
pMamm B  (241)   GTGCCAG - GGGGAGTTTGACTGGGGCGGTACACCTGTCAAACGGTAA
pMamm C  (253)   GTGCCAG G GGGAGTTTGACTGGGGCGGTACACCTGTCAAACGGTAA
pPros    (351)   GTGCCAG G GGGAGTTTGACTGGGGCGGTACACCTGTCAAACGGTAA 401                                                450
pMamm A  (359)   ...G AACCTCCCGTGGAGCA
pMamm B  (290)   ...A AACCTCCCGTGGAGCA
pMamm C  (303)   ...G AACCTCCCGTGGAGCA
pPros    (401)   ...G AACCTCCCGTGGAGCA 451                                                500
pMamm A  (409)   AAGGGCAAA GCTCGCT  ATCTTGATTTTCAGTACGAATACAGACC
pMamm B  (339)   AAGGGCAAA --------  ATCTTGATTTTCAGTACGAATACAGACC
pMamm C  (353)   AAGGGCAAA GCTCGCT  ATCTTGATTTTCAGTACGAATACAGACC
pPros    (451)   AAGGGCAAA GCTCGCT  ATCTTGATTTTCAGTACGAATACAGACC 501                                                550
pMamm A  (459)   T AGCGGGGCCTC C GATC C  TGACCTTTTGGGTTTTAAGCAGGA
pMamm B  (382)   A AGCGGGGCCTC A GATC -  TGACCTTTTGGGTTTTAAGCAGGA
pMamm C  (403)   A AGCGGGGCCTC C GATC C  TGACCTTTTGGGTTTTAAGCAGGA
pPros    (501)   A AGCGGGGCCTC C GATC C  TGACCTTTTGG TTTTAAGCAGGA 551                                                600
pMamm A  (509)   ...AGAAAAGTTACCACAGGGATAACTGGCTTGTGGCGGCCAAGCCTT
pMamm B  (430)   ...AGAAAAGTTACCACAGGGATAACTGGCTTGTGGCGGCCAAGCCTT
pMamm C  (453)   ...AGAAAAGTTACCACAGGGATAACTGGCTTGTGGCGGCCAAGCCTT
pPros    (551)   ...AGAAAAGTTACCACAGGGATAACTGGCTTGTGGCGGCCAAGCCTT 601                                                650
pMamm A  (559)   T TAG  ACGTCGCTTTTTGATCCTTCGATGTCGGCTCTTCCTATCATT T
pMamm B  (480)   A AGC  ACGTCGCTTTTTGATCCTTCGATGTCGGCTCTTCCTATCATT GG
pMamm C  (503)   T AGC  ACGTCGCTTTTTGATCCTTCGATGTCGGCTCTTCCTATCATT T
pPros    (601)   T AGC  ACGTCGCTTTTTGATCCTTCGATGTCGGCTCTTCCTATCATT T 651                                                700
pMamm A  (609)   T AGAATTCACCAACCGTTGGATTGTTCACCCACTAATAGGGAA...
pMamm B  (530)   A AGAATTCACCAACCGTTGGATTGTTCACCCACTAATAGGGAA...
pMamm C  (553)   A AGAATTCACCAACCGTTGGATTGTTCACCCACTAATAGGGAA...
pPros    (651)   A AGAATTCACCAACCGTTGGATTGTTCACCCACTAATAGGGAA...

701                                                750
pMamm A  (659)   AGCTGG T  TAGACCGTCGTGAGACAGG A T TTACCCTACTGATGA
pMamm B  (580)   AGCTGG T  TAGACCGTCGTGAGACAGG - T TTACCCTACTGATGA
pMamm C  (603)   AGCTGG T  TAGACCGTCGTGAGACAGG AG T TTACCCTACTGATGA
pPros    (701)   AGCTGG A  TAGACCGTCGTGAGACAGG AG T TTACCCTACTGATGA 751                                                800
pMamm A  (709)   TGT TGTTGCCATG T  CTGCTCAGTACGAGAGGAACCGCAGGTT
pMamm B  (629)   GTG TGTTGCCATG A  CTGCTCAGTACGAGAGGAACCGCAGGTT
pMamm C  (653)   GTG TGTTGCCATG A  CTGCTCAGTACGAGAGGAACCGCAGGTT
pPros    (751)   GTG TGTTGCCATG A  CTGCTCAGTACGAGAGGAACCGCAGGTT 801                                                850
pMamm A  (759)   ACATTTGGTGTATGTGCTTGGC A  AGCCAATGGGCGAAGCTAC
pMamm B  (679)   ACATTTGGTGTATGTGCTTGGC G  AGCCAATGGGCGAAGCTAC
pMamm C  (703)   ACATTTGGTGTATGTGCTTGGC A  AGCCAATGGGCGAAGCTAC
pPros    (801)   ACATTTGGTGTATGTGCTTGGC A  AGCCAATGGGCGAAGCTAC 851                                                900
pMamm A  (809)   CTGTGGGATTA G ACTGA CGG - CTAAGTCA T AATCCCGCCCAGG
pMamm B  (729)   CTGTGGGATTA A TACTGA A CGG C CTAAGTC A - AATCCCGCCCAGG
pMamm C  (753)   CTGTGGGATTA G ACTGA A CGG C CTAAGTC A - AATCCCGCCCAGG
pPros    (851)   CTGTGGGATTA G ACTGA A CGG C CTAAGTC A - AATCCCGCCCAGG 901                                                950
pMamm A  (857)   ...GATACGGCAGCGCCGCGGAGCCTCGGTTGGCCTC... TA CCCGG
pMamm B  (778)   ...GATACGGCAGCGCCGCGGAGCCTCGGTTGGCCTC... G-GCCGG
pMamm C  (802)   ...GATACGGCAGCGCCGCGGAGCCTCGGTTGGCCTC... A-GCCGG
pPros    (900)   ...GATACGGCAGCGCCGCGGAGCCTCGGTTGGCCTC... A-GCCGG
```

TABLE 5-continued

Comparison
MammA, MammB, MammC, Prostate

```
              951                                              1000
pMamm A  (907) CCCCGCCTGTCCCCGCCGGCGGCCGCCCCCCCCTCCACGCGCCCC
pMamm B  (827) CCCCGCCTGTCCCCGCCGGCGG-GTCGCCCCCCTCCACGCGCCCC
pMamm C  (851) CCCCGCCTGTCCCCGCCGGCGGCCGCCCCCCCTCCACGCGCCCC
 pPros   (949) CCCCGCCTGTCCCCGCCGGCGG--CGCCCCCCTCCACGCGCCCC 1001                                             1050
pMamm A  (957) GGCGCGGGAGGGCGCGTGCCCCGCCGCGCGCCGGGACCGGGCTC
pMamm B  (876) GGCGCGGGAGGGCGCGTGCCCCGCCGCGCGCCGGGACCGGGCTC
pMamm C  (901) GGCGCGGGAGGGCGCGTGCCCCGCCGCGCGCCGGGACCGGGCTC
 pPros   (997) GGCGCGGGAGGGCGCGTGCCCCGCCGCGCGCCGGGACCGGGCTC 1051                                             1100
pMamm A (1007) GGAGTGCCCTTCGTCCTGGGAAACGGGGCGCGGCCGGAAAGGC
pMamm B  (926) GGAGTGCCCTTCGTCCTGGGAAACGGGGCGCGGCCGGAAAGGC
pMamm C  (951) GGAGTGCCCTTCGTCCTGGGAAACGGGGCGCGGCCGGAAAGGC
 pPros  (1047) GGAGTGCCCTTCGTCCTGGGAAACGGGGCGCGGCCGGAAAGGC 1101                                             1150
pMamm A (1057) CCCTCGCCCGTCACGCACCGCACGTTCGCT---CGTCCCAATCG
pMamm B  (976) CCCTCGCCCGTCACGCACCGCACGTTCGCT---CGTCCCAATCG
pMamm C (1001) CCCTCGCCCGTCACGCACCGCACGTTCGCT---CGTCCCAATCG
 pPros  (1097) CCCTCGCCCGTCACGCACCGCACGTTCGTGGAAGCTGGC-TAAA 1151                                             1200
pMamm A (1104) GCAGGAGTGCACCCATTCACAATATAGATAAAATGCATGTATTTATG
pMamm B (1023) GCACGAGTAGCACCATTCACAATAGAGATACAATGCATGTCTTTATT
pMamm C (1048) GCACGAGTAGCACCATTCACAATAGAGATACAATGCATGTCTTTATG
 pPros  (1146) CCAGCTCCATCTCAGTCCTCA--GCGTGGCAAACTGAGGAGCCCTGC 1201                                             1250
pMamm A (1154) ATATATGATTTTTTCCTTTGGGTAGATATCAGTAGTGGGATTCCTA
pMamm B (1073) ATATAATGATTCTTTTCCTTTGGGCAGATATCCAGTAGTGGGATTCCTA
pMamm C (1098) ATATAATGATTCTTTTCCTTTGGGTAGATATCCAGTAGTGGGATTCCTA
 pPros  (1193) CTGCA--GAAG-CAGCTGACCCAACCAAAGACCCACTC------TTGCA 1251                                             1300
pMamm A (1204) GATCACCTGGAGTTGTATTCTGCTTTATTGAGAAATCTATATATGAT
pMamm B (1123) GATCACCTGGAGTTGTATTCTGCTTTATTGAGAAATCTATATATGAT
pMamm C (1148) GATCACCTGGAGTTCTATTCTGCTTTATTGAGAAATCTATATATGAT
 pPros  (1233) GAGAGCCAGCTGCTGGCATCTCAAAGCCCAGCGGCAGATCCGCTGCTCA- 1301                                             1350
pMamm A (1254) TTCCATAGAGTTGTACAAATTTACATCCCACAAAGTCATTTTTTAA
pMamm B (1173) TTCCATAGAGTTGTACAAATTTACATCCCACCAA-GTCATTTTTTAA
pMamm C (1198) TTCCATAGAGTTGTACAAATTTACATCCCCACCAA-GTCATTTTTTAA
 pPros  (1282) ------GGAACCGACGACCAG---CACTGGT-CGA---TGTCAGGTGCAG 1351                                             1400
pMamm A (1304) ATATGAAAAATCGTCTGGAGAAATCCCCCATTACTATCCCCCTTTTA
pMamm B (1222) ATATGAAAAATCGTCTGGAGAAATCCCCTATTACTATCCCCCTTTTA
pMamm C (1247) ATATGAAAAATCGTCTGGAGAAATCCCCTATTACTATCCCCCTTTTA
 pPros  (1319) GCAGAAAAGGAGGCTGTCTATGAG-GAAACTCCAGAGCAGGAG------A 1401                                             1450
pMamm A (1354) CCTCTCTAATGCAGAATGAATTCAAGGCCAACGTATTTAAAATTTCA
pMamm B (1272) CCTCTCTAATGCAGAATGAATTCAAGGCGAACGTATTTACAAATTTCA
pMamm C (1297) CCTCTCTAATGCAGAATGAATTCAAGGCGAACGTATTTACAAATTTCA
 pPros  (1362) CGT-TCTAG----GAGCAGCCCGCACTGGTGCAGC----AGTAAGGTGCT 1451                                             1500
pMamm A (1404) TTATACAGAAAAATTGAATATTGAAATTTCTGCATAAGACCACAGATT
pMamm B (1322) TTATACAGACAAATTGAATATTGAAATTT-CTGCATTAGAGCCACAGATT
pMamm C (1347) TTATACAGACAAATTGAATATTGAAATTT-CTGCATAAGAGCCACAGATT
 pPros  (1403) GGCTCTGAGCACATTCACCACC-ACATTC----------AAAGGCCAG---

1501                                             1550
pMamm A (1454) TTAGGATTCCAAGTTCTATGAACAAGGACAAGTCCTCAGGACTGCAA
pMamm B (1371) TTAGGATTCCAAGTTCTAAGAACAAGGACAAGTCCTCAGGACTTGCAA
pMamm C (1396) TTAGGATTCCAAGTTCTATGAACAAGGACAAGTCCTCAGGACTGCAA
 pPros  (1439) ---GGCTCA-----GT--------GGCAAGGCCAGTGTCCCGTGCC 1551                                             1600
pMamm A (1504) AGCTGCAATGGCAATCTCAGTGAATACATTCCAGCAGTCCACCAG
pMamm B (1421) AGCTGCAATGGCAATCTCACAGAATACATTCCAGCAGTCCACCAG
pMamm C (1446) AGCTGCAATGGCAATCTCAGTGAATACATTCCAGCAGTCCACCAG
 pPros  (1473) TGTACGACTACCGGCAGCCGACCACACAGAGATCCCTTGACCCGGAA
```

TABLE 5-continued

Comparison
MammA, MammB, MammC, Prostate

```
              1601                                              1650
pMamm A (1554) CTTAAATCTACTGAATTGGCTTTTCTAACATCATTAATACCTACTTAT
pMamm B (1471) CTTATATTCTACTGAATTGGCTTT-GTAACATCATTTATACCTACTTAT
pMamm C (1496) CATATATTCTACTGAATTGGCTTT-GTAACATCGATTAATACCTACTTAT
 pPros  (1523) AGCCTCATG------ACGGGGATC-GATGTGATCG---------AAG---

1651                                              1700
pMamm A (1604) TAAAACTAATCAAAAGCGTTATATAAAATATCTTAAGCTATAAAAAT
pMamm B (1520) TAAAACTAATCAAAAGGGTTATATCAAAATATCTTAAGCTAAAAAAT
pMamm C (1545) TAAAACTAATCAAAAGCGTTATATCAAATATACTTAAGCTATAAAAAT
 pPros  (1554) -AAGGCTGGTGGCGTGGCTAAGGGCGGGATGGCCATTTTCCATGTTCCC 1701                                              1750
pMamm A (1654) CAAATTATAGCTAAAGCTGTTTCTTTACCATTTTATTTCTAAACATAA
pMamm B (1570) CAAATTATAGCAAAAGCTGTTTCTTTGCATTTTATTTCAAAACAAAA
pMamm C (1595) CAAATTATAGCTAAAGCTGTTTCTTTACCATTTTATTTCAAAACATAA
 pPros  (1603) TGCCAACTACCTGGAGCCATTGAGTGAAGGC---GGAGGGCACATGTTGC 1751                                              1800
pMamm A (1704) AATAGCTACGGTCTATTGCGAT--TTATA-CTGTACCAGACACTGTGTT
pMamm B (1620) AATAGCTACGGTCTATTGGGAT--TTATA-CTGTACCAGACACTGTGTT
pMamm C (1645) AATAGCTACGGTCTATTGCGAT--TTATA-CTGTACCAGACACTGTGTT
 pPros  (1650) CCCTCTCCTGTCAGACATGGGTTCCCTATGTGGAAGAGGAGGCCTGGG 1801                                              1850
pMamm A (1751) TGTCACATTTCAAAATGTTCTCATCGTAATTTACAATAACTCTGTCG
pMamm B (1667) TGTCACATTTCAAAATGTTCTCATCGTAATTTACAATAATCTGTAG
pMamm C (1692) TGTCACATTTCAAAAAGTTCTCATCGTAATTTTACAATAATCTGTAG
 pPros  (1700) AGTTGACATGCAGCACCCTGCG-CAGGAATAGGACCCGCAG--T---GAA 1851                                              1900
pMamm A (1801) GCTCAGAAAATCTCTTACGTAGAAACATTCAGTAAAAGAGACCT
pMamm B (1717) GCTGGAGAAATAGTCTTACGTAGAAACATTCAGCAG--AAAGAGACCT
pMamm C (1742) GCTGAG-AAATAGTCTTACGTAGAAACATTCAGCT--AAAGAGACCT
 pPros  (1743) GATCAGGCCCTCAGGGCTCCGC----GCCGGCTGGCAGC--ACTCC--AGCGCG 1901                                              1950
pMamm A (1851) CGGATCCTTGGCGTTCAACTTGCCGAAAGTTCGAACGGACGAGGATT
pMamm B (1765) CTGAACCTTGGAGGTCAACTTGCCGAAAGTTCGAACGGACGAGGACT
pMamm C (1790) CTGAACCTTGGAGCTCAACTTGCCGAAAGTTCGAACGGACGAGGATCT
 pPros  (1785) GTCCACGCCA--GATGCAGCAATGCGCTGCGGATTCCGCACATCCTTCCG 1951                                              2000
pMamm A (1901) CAC--GTGACCATCACACTCCAGAA--CTCT----AAACCACACTGC
pMamm B (1815) CAA--CCTGACCATCACACTCCAGAT--CTCT----CCATACCACACTGC
pMamm C (1840) CAA--CCTGACCATCACACTCCAGAT--CTCT----CCATACCACACTGC
 pPros  (1833) GCTTCGCCGGCTCCGAGAGCTGGCGTGCGCTGACAGGATAG 2001                                              2050
pMamm A (1944) AAGCAATC---TGCCTGG----CATCTTAGTCCGCGTC----------
pMamm B (1858) TAGCACATG---TGCCTGG----CATCTTATCCTGGCTCC----------
pMamm C (1883) TAGCAGATG---TGCCTGG----CATCTTATCCTGGCTCGTGTTATT-TC
 pPros  (1883) GGAGCCAAGCCCGGCTGGGGCCAAGCCCTGAGTGCCAGTGCCAAGCTG 2051                                              2100
pMamm A (1978) CTTTTTTATTCCTTCCCTT--CCTCCACTACGCTTTTTGCCCCCG--
pMamm B (1892) CTKYTT-ATTCCTTCCCTT--CCTCCACTACGCCTTTTTCCCCCG--
pMamm C (1926) CCTTTTTATTCCTTCCCTT--CCTCCACTACGCCTTTTTCCCCCG--
 pPros  (1933) GGGGGAAGGGTCCTGAGGAGGGGCAGTGGGAGGGTCTGGCCGCCTTCTG 2101                                              2150
pMamm A (2024) --ATTCCTT-CTGCTTTTATTGTAATCACAAACTATACATTGT
pMamm B (1937) -ATTCTTTTCTTTCTTTTATTGTAATCACAAACTATACATGTT
pMamm C (1972) -ATTCCTTCTGCTCTTTTAATGTAATCACAAACTATACATGCTT
 pPros  (1983) CATTTATTCGGCTT--TTTTCTGTTCTCGTGGTT--GTAAGGGGTGGTG 2151                                              2200
pMamm A (2072) ATCAGATCAATTGATCTACCACAAAAAGCTATCAACTACGGCGAGTGA
pMamm B (1986) ATCAGAAGAATTGATCTACCACAAAAAGGTATAAAGTACGGCTGAGTGA
pMamm C (2021) ATCAGAAGAATTGATCTACCACAAAAGGGATATAAAGTACGGCTGAGTGA
 pPros  (2029) GCCACCAATGTCTAGAATGACCCTTGCAA---ACAGTGAACG-------T 2201                                              2250
pMamm A (2122) ACTCATCCCCGTAATCCTCGCCTTTGGAGGCCAAGCAG-CCAGATC
pMamm B (2036) AGCTCATCCCCGTAATG-TAGCCTTTGGAGGCCAAGCAG-CCAGATC
pMamm C (2071) AGCTCATCCCCGTAATCCTCGCCTTTGGAGGCCAAGCAG-CCAGATC
 pPros  (2069) AAAGAATTGTTTTAGG-AG-AGTTGTGAC-CAAAGTCAGAGTCGATC
```

TABLE 5-continued

Comparison
MammA, MammB, MammC, Prostate

```
                2251                                          2300
pMamm A (2171)  ACTTTCAGTCCAGACTCCAGCCCAACCTGGGCAAAATCGTCAAACCTG
pMamm B (2084)  ACTT-CA-TCCAGAGTTCAGCCCAACCTGGGCAAAATCGTCAAACCTG
pMamm C (2120)  ACTT-CAGTCCAGAGTTCAGCCCAACCTGGGCAAAATCGTCAAACCTG
 pPros  (2115)  ATGGTG--------CTTTGCAGCAGGGAATTTGTGTTCTTGAGCGTGC 2301                                          2350
pMamm A (2221)  TCGCTACAAAAAGAGAAAAAA-GTGAGCGGCGCGTCCTGGCACACACC
pMamm B (2132)  TCGCTACAAAAAGAGACAAAA--TTGAGCGGCGCGTCCTGGCACACACC
pMamm C (2169)  TCGCTACAAAAAGAGAGAAAA--TTGAGCGGCGCGTCCTGGCACACACC
 pPros  (2157)  GGCGTGGTCCCCACTCGATTTCTCGGCCCTCTGGCTGGCTATGGGAAG 2351                                          2400
pMamm A (2270)  TCTAGTCTCAGCTACTGTGAGGGCTGAGGTGGCAGATTGCATTGAGCCCA
pMamm B (2180)  TGTAGTCTCAGCTACTGTGAGGGCTGAGGTGGCAGATTGCATTGAGCCCA
pMamm C (2217)  TGTAGTCTCAGCTACTGTGAGGGCTGAGGTGGCAGATTGCATTGAGCCCA
 pPros  (2207)  GGGAATGCAGAGGGCGAAGCTCCCACCCGGGTCG--TCCAAAACGGCA 2401                                          2450
pMamm A (2320)  GGAGGTGGCAGCTGCAGCAGTGCGCGCAGATTGCGCCATTGCACTCCAGC
pMamm B (2230)  GGAGGTGGCAGCTGCAGCAGTGCGCGCAGATTGCGCCATTGCACTCCAGC
pMamm C (2267)  GGAGGTGGCAGCTGCAGCAGTGCGCGCAGATTGCGCCATTGCACTCCAGC
 pPros  (2255)  GACACAACGATGTTCGTCCACGCGCGGCACTCGATCG--TCCGGCGCCA 2451                                          2500
pMamm A (2370)  CTGGGTGAGAGCGAGACCCTGTCTTCCAAAGAAAAAAAAAAAAAAAA-
pMamm B (2280)  CTGGGTGAGAGCGAGACCCTGTCTTCCAAAAAAAAAAAAAAAAA---
pMamm C (2317)  CTGGGTGAGAGCGAGACCCTGTCTCCAAAAAAAAAAA-----------
 pPros  (2303)  GCGTGCTCCTCA-ACTGATTCTGACTTCAGGAAAAGTAAAAAAAAAAA 2501                2532
pMamm A (2419)  --------------------------------
pMamm B (2327)  --------------------------------
pMamm C (2356)  --------------------------------
 pPros  (2352)  AAAAACTCGAGAAGCTTTGGACTTCTTCGCCA
```

---

I claim:

1. A method for detecting prostate, colon or ovarian cell cancer, comprising:
   a) analyzing body tissue or fluid for a protein having the following characteristics:
      i. a molecular weight of approximately 50–60 kDa;
      ii. produced by normal prostate, colon, or ovarian cells, but not by prostate, colon, or ovarian cancer cells;
      iii. binds antibody 7G6 (ATCC Accession No. PTA-4606); and
   b) correlating reduction or absence of the protein, relative to a control sample, with the presence of prostate, colon, or ovarian cell cancer.

2. The method of claim 1, wherein said analyzing comprises immunoassay.

3. The method of claim 2, wherein said immunoassay is a dot-blot assay.

4. The method of claim 2, wherein said immunoassay is a Western-blot.

5. The method of claim 1, wherein said body tissue or fluid is blood.

6. The method of claim 1, wherein said protein is produced by normal prostate cells, and is encoded by SEQ ID NO: 4.

* * * * *

UNITED STATES PATENT AND TRADEMARK OFFICE
CERTIFICATE OF CORRECTION

PATENT NO. : 6,939,714 B2
DATED : September 6, 2005
INVENTOR(S) : Ervin

It is certified that error appears in the above-identified patent and that said Letters Patent is hereby corrected as shown below:

Column 4,
Line 15, "Mammmastatin" should read -- Mammastatin --.

Columns 11 and 12,
TABLE 1, lines 553, 651 are incorrect - the PTO duplicated the 503 and 601 lines here instead of the correct lines as indicated on the application.

Column 15,
TABLE 1, line 1722 - "1722" should read -- 1742 --.

Signed and Sealed this

Eleventh Day of April, 2006

JON W. DUDAS
*Director of the United States Patent and Trademark Office*

SEQUENCE LISTING

<160> NUMBER OF SEQ ID NOS: 10

<210> SEQ ID NO 1
<211> LENGTH: 2418
<212> TYPE: DNA
<213> ORGANISM: Homo sapiens

<400> SEQUENCE: 1

```
tggggctcca ccccggtggc ggccgctcta gaactagtgg atccccgggg ctgcaggaat    60
tcggcacgag cacggtgaag agacatgaga ggtgtagaat ccgtgggagg cccccggcgc   120
cccccggtg tccccgcgag gggcccgggg cggggtccgc cggccctgcg ggccgccggt   180
gaaataccac tactcttatc gttttttcac tgacccggtc gagcgggggg gcgagccccg   240
aggggctctc gcttctggcg ccaagcgccc ggccgcgcgc cggccgggcg cgacccgctc   300
cggggacagt gccaggtggg gagtttgact ggggcggtac acctgtcaaa cggtaacgca   360
ggtgtcctaa ggcgagctca gggaggacag aaacctcccg tggagcagaa gggcaaaagc   420
tcgcttgatc ttgattttca gtacgaatac agaccgtgta agcggggcct cacgatcctt   480
ctgaccttt gggttttaag caggaggtgt cagaaaagtt accacaggga taactggctt   540
gtggcggcca agcgttcatt aggacgtcgc tttttgatcc ttcgatgtcg gctcttccta   600
tcattgtgta gcagaattca ccaagcgttg gattgttcac ccactaatag ggaacgtgag   660
ctgggtttag accgtcgtga gacaggttat tttacccta ctgatgattg tttgttgcca   720
tggttatcct gctcagtacg agaggaaccg caggttcaga catttggtgt atgtgcttgg   780
```

-continued

```
ctgaggagcc aatggggcga agctaccatc tgtgggatta tgactgacgc tctaagtcat    840
gaatcccgcc caggcggaac gatacggcag cgccgcggag cctcggttgg cctcggatta    900
gccggtcccc cgcctgtccc cgccggcggg ccgccccccc ccctccacgc gccccgcgcg    960
cgcgggaggg cgcgtgcccc gccgcgcgcc gggaccgggg tccggtgcgg agtgcccttc   1020
gtcctgggaa acggggcgcg gccggaaagg cggccgcccc ctcgcccgtc acgcaccgca   1080
cgttcgtgct cgtgccgaat tcggcacgag tgcacccatt cacaatatac atacaagtgc   1140
atgtatcttt atgatataat gaattctttt cctttgggta gatatccagt agtgggattg   1200
ctagatcacc tggtagttct atttctggtt tatttagaaa tcttcatact gatttccata   1260
gaggttgtac aaatttacat ccctaccaaa gtgattttt taaatatgaa agaatggtct   1320
ggagaaatgc ccctcattag tatccccctt ttacctctct actgcagaat gacttcaagg   1380
ggtacaggta tttacaagtt tcattataca gacaaattga atattgaaat tttctgcata   1440
agaggcacag attttaggat tcaaagttgt atgaacaagg acaagtgctc tagggacttg   1500
caaagctgga attggaaatc tcagatgaaa tacatttcta gtagtaccac cagcatatat   1560
tctactgaat tggcttttgt gatcatcatt aatacctact tattaaaact aatgaaaagg   1620
gtttatatca aatatacttt aaggtataaa atcaaatta taggtaaagc tgttttcttt   1680
agcattttaa tttcaaaaca taaaatagct accgtctatt gggcatttat actgtacgag   1740
acactgtgtt tgtcacattt caaaaatgtt ctcatggtaa tgttcacaat aattctgtcg   1800
ggtgagaaaa tagtcttacc gtagtaagac tattcagtaa aacgaaacct ctgaaccttg   1860
gagttcaact tgcgcaaagt tagtaacagg actaggactt gaacctgaac catcacactc   1920
gagatctctc cataccacac tgctagcaca tgtgcctgtc atcttattcc tggctcccctt   1980
ttttatttcc tttcccttcc tcccacaacc ccttttccc cccatttctt tctttctttt   2040
tatttgttaa ttacataact aatacatgtt tatgagaaca attgatatag cacaaaagga   2100
tataaagtac gggggagtga tagctcatcc ctgtaatcct agcactttgg aaggccaagg   2160
caggcagatc actttgagtc cagagttcga accagcctg gcaacatgg tgaaaccctg   2220
tctctacaaa aaaatacaaa aaatttagcc gggcgtgctg gcacagacct gtagtctcag   2280
ctactctgag gctgaggtg ggaagattga ttgagcccag gaggtggaag ctgcagcagt   2340
gcgctgagat tgcgccattg cactccagcc tgggtgagag agagacccc tgtctccaaa   2400
aaaaaaaaaa aaaaaaaa                                                  2418
```

<210> SEQ ID NO 2
<211> LENGTH: 2326
<212> TYPE: DNA
<213> ORGANISM: Homo sapiens

<400> SEQUENCE: 2

```
cggcacgagc acggtgaaga gacatgagag gtgtagaata agtgggaggc ccccggcgcc     60
ccccgggtgt cccgcgagg ggcccgcggg tccgccggcc cgcggcgcc ggtgaaatac    120
cactactctg atcgttttt cactgacccg gtgaggcggg gggcgagccc cgagggctc    180
tcgcttctgg cgccaagcgc ccggccgcgc gcggccgggg cgcgacccgc tccgggaca    240
gtgccagtgg ggagtttgac tggggcggta cacctgtcaa acggtaacgc aggtgtccta   300
aggcgagctc aggaggaca aaacctcccg tggagcagaa gggcaaaatg atcttgattt    360
tcagtacgaa tacagaccgt gaaagcgggg cctcagatct tctgaccttt tgggttttaa    420
```

```
gcaggaggtg tcagaaaagt taccacaggg ataactggct tgtggcggcc aagcgttcaa      480
agcgacgtcg cttttttgatc cttcgatgtc ggctcttcct atcattggga agcagaattc      540
accaagcgtt ggattgttca cccactaata gggaacgtga gctgggttta gaccgtcgtg      600
agacaggttt gtttacccta ctgatgatgt gttgttgcca tggtaatcct gctcagtacg      660
agaggaaccg caggttcaga catttggtgt atgtgcttgg ctggggagcc aatgggcga      720 agctaccatc tgtgggatta ttactgaacg cctctaagtc agaatcccgc ccaggcggaa      780
cgatacggca gcgccgcgga gcctcggttg gcctcggatg gccggtcccc cgcctgtccc      840
cgccggcggc gcccccccc cctccacgcg ccccgcgcgc gcgggagggc gcgtgccccg      900
ccgcgcgccg ggaccggggt ccggtgcgga gtgcccttcg tcctgggaaa cggggcgcgg      960
ccggaaaggc ggccgcccc tcgcccgtca cgcaccgcac gttcgtgctc gtgccgaatt      1020
cggcacgagt agcaccattc acaatagaca tacaagtgca tgtatctttta ttatataatg      1080 aattcttttc ctttggggag atatccagta gtgggattgc tagatcacct ggtagttcta      1140
tttctggttt attgagaaat cttcatactg atttccatag aggttgtaca aatttacatc      1200
cctaccaagt gatttttta aatatgaaag aatggtctgg agaaatgccc tcattagta      1260 tccccctttt acctctctac tgcagaatga cttcaagggg tacaggtatt tacaagtttc      1320
attatacaga caaattgaat attgaaattt ctgcattaga ggcacagatt ttaggattca      1380
aagttgtaag aacaaggaca agtgctctag ggacttgcaa agctggaatt ggaaatctca      1440
gaagaaatac atttctagta gtaccaccag catatattct actgaattgg ctttgtgatc      1500
atcatttata cctacttatt aaaactaatg aaaagggttt atatcaaata tactttaagg      1560
taaaaaaatc aaattatagg aaaagctgtt ttcttttgca ttttaatttc aaaacaaaaa      1620
atagctaccg tctattgggc atttatactg taccagacac tgtgtttgtc acatttcaaa      1680
aatgttctca tggtaatgtt cacaataatt ctgtagggtg gagaaatagt cttaccgtag      1740
taagactatt cagaaacgaa acctctgaac cttggagttc aacttgcgca aagttagtaa      1800
caggactagg acttgaacct gaaccatcac actccagatc tctccatacc acactgctag      1860
cacatgtgcc tgtcatctta ttcctggctc cctkyttatt tcctttccct tcctcccaca      1920
accccttttt cccccatt cttttctttc tttttatttg ttaattacat aactaataca      1980
tgtttatcag aacaattgat atagcacaaa aggatataaa gtacgggtga gtgatagctc      2040
atccctgtaa tctagcactt tggaaggcca aggcaggcag atcacttgat ccagagttcg      2100
agaccagcct gggcaacatg gtgaaaccct gtctctacaa aaaatacaa aaatttagcc      2160 gggcgtgctg gcacacacct gtagtctcag ctactctgag ggctgaggtg gaagattga      2220 ttgagcccag gaggtggaag ctgcagcagt gcgctgagat tgcgccattg cactccagcc      2280
tgggtgagag agagagaccc tgtcttcaaa aaaaaaaaaa aaaaaa      2326
```

<210> SEQ ID NO 3
<211> LENGTH: 2355
<212> TYPE: DNA
<213> ORGANISM: Homo sapiens

<400> SEQUENCE: 3

```
gaattcggca cgagcacggt gaagagacat gagaggtgta gaataagtgg gaggcccccg       60 gcgcccccc ggtgtccccg cgagggccc ggggcgggt ccgccggccc tgcgggccgc      120
cggtgaaata ccactactct gatcgttttt tcactgaccc ggtgaggcgg ggggcgagc      180 cccgagggc tctcgcttct ggcgccaagc gcccggccgc gcgccggccg ggcgcgaccc      240
```

-continued

```
gctccgggga cagtgccagg tgggagttt gactgggcg gtacacctgt caaacggtaa      300
cgcaggtgtc ctaaggcgag ctcagggagg acagaaacct cccgtggagc agaagggcaa     360
aagctcgctt gatcttgatt ttcagtacga atacagaccg tgaaagcggg gcctcacgat     420
ccttctgacc ttttgggttt taagcaggag gtgtcagaaa agttaccaca gggataactg     480
gcttgtggcg gccaagcgtt catagcgacg tcgcttttg atccttcgat gtcggctctt     540
cctatcattg tgaagcagaa ttaccaagc gttggattgt tcacccacta ataggaacg      600 tgagctgggt ttagaccgtc gtgagacagg ttagttttac cctactgatg atgtgttgtt    660
gccatggtaa tcctgctcag tacgagagga accgcaggtt cagacatttg gtgtatgtgc    720
ttggctgagg agccaatggg gcgaagctac catctgtggg attatgactg aacgcctcta    780
agtcagaatc ccgcccaggc ggaacgatac ggcagcgccg cggagcctcg gttggcctcg    840
gatagccggt ccccgcctg tccccgccgg cgggccgccc cccccctcc acgcgccccg      900 cgcgcgcggg agggcgcgtg cccgccgcg cgccgggacc ggggtccggt gcggagtgcc     960
cttcgtcctg ggaacgggg gcggccgga aggcggccg cccctcgcc cgtcacgcac       1020 cgcacgttcg tgctcgtgcc gaattcggca cgagtagcac cattcacaat agacatacaa    1080
gtgcatgtat ctttatgata taatgaattc ttttccttg ggtagatatc cagtagtggg    1140
attgctagat cacctggtag ttctatttct ggtttattga gaaatcttca tactgatttc    1200
catagaggtt gtacaaattt acatccctac caagtgattt ttttaaatat gaaagaatgg    1260
tctggagaaa tgcccctcat tagtatcccc cttttacctc tctactgcag aatgacttca    1320
aggggtacag gtatttacaa gtttcattat acagacaaat tgaatattga aatttctgca    1380
taagaggcac agattttagg attcaaagtt gtatgaacaa ggacaagtgc tctagggact    1440
tgcaaagctg gaattggaaa tctcagatga aatacatttc tagtagtacc accagcatat    1500
attctactga attggctttg tgatcatcat taatacctac ttattaaaac taatgaaaag    1560
ggtttatatc aaatatactt taaggtataa aaatcaaatt ataggtaaag ctgttttctt    1620
tagcatttta atttcaaaac ataaaatagc taccgtctat tgggcattta tactgtacca    1680
gacactgtgt ttgtcacatt tcaaaaatgt tctcatggta atgttcacaa taattctgta    1740
gggtgagaaa tagtcttacc gtagtaagac tattcagtaa acgaaacctc tgaaccttgg    1800
agttcaactt gcgcaaagtt agtaacagga ctaggacttg aacctgaacc atcacactcc    1860
agatctctcc ataccacact gctagcacat gtgcctgtca tcttattcct ggctcctgtt    1920 atttccctt ttatttcctt tcccttcctc ccacaacccc ttttccccc catttctttt     1980 ctttcttttt aattgttaat tacataacta atacatgctt atcagaacaa ttgatatagc    2040
acaaaaggat ataaagtacg ggtgagtgat agctcatccc tgtaatccta gcactttgga    2100
aggccaaggc aggcagatca cttgagtcca gagttcgaga ccagcctggg caacatggtg    2160
aaaccctgtc tctacaaaaa aatacaaaaa tttagccggg cgtgctggca cacacctgta   2220
gtctcagcta ctctgagggc tgaggtggga agattgattg agcccaggag gtggaagctg    2280
cagcagtgcg ctgagattgc gccattgcac tccagcctgg gtgagagaga gagaccctgt    2340
ctcaaaaaaa aaaaa                                                     2355
```

<210> SEQ ID NO 4
<211> LENGTH: 2333
<212> TYPE: DNA
<213> ORGANISM: Homo sapiens

<400> SEQUENCE: 4

```
gcacgagatt cccactgtcc ctacctacta tccagcgaaa ccacagccaa gggaacgggc      60
ttggcggaat cagcggggaa agaagaccct gttgagcttg gcccccggc gcccccgg       120
tgtccccgcg aggggcccgg ggcggggtcc gccggcctg cgggccgccg gtgaaatacc     180
actactctga tcgttttttc actgacccgg tgaggcgggg gggcgagccc cgaggggctc    240
tcgcttctgg cgccaagcgc ccggccgcgc gccggccggg cgcgacccgc tccggggaca    300
gtgccaggtg gggagtttga ctgggcggt acacctgtca aacggtaacg caggtgtcct     360
aaggcgagct cagggaggac agaaacctcc cgtggagcag aagggcaaaa gctcgcttga    420
tcttgatttt cagtacgaat acagaccgtg aaagcggggc ctcacgatcc ttctgacctt    480
ttgggtttta agcaggaggt gtcagaaaag ttaccacagg gataactggc ttgtggcggc    540
caagcgttca tagcgacgtc gcttttgat ccttcgatgt cggctcttcc tatcattgtg     600
aagcagaatt caccaagcgt tggattgttc acccactaat agggaacgtg agctgggatt    660
agaccgtcgt gagacaggtt agttttaccc tactgatgat gtgttgttgc catggtaatc    720
ctgctcagta cgagaggaac cgcaggttca gacatttggt gtatgtgctt ggctgaggag    780
ccaatggggc gaagctacca tctgtgggat tatgactgaa cgcctctaag tcagaatccc    840
gcccaggcgg aacgatacgg cagcgccgcg gagcctcgt tggcctcgga tagccggtcc     900
cccgcctgtc cccgccggcg ggccgccccc ccctccacgc gccccgcgcg cgcgggaggg    960
cgcgtgcccc gccgcgcgcc gggaccgggg tccggtgcgg agtgcccttc gtcctgggaa   1020
acggggcgcg gccggaaagg cggccgcccc ctcgcccgtc acgcaccgca cgttcgtggg   1080
gaacctggcg ctaaaccacc tccatctcca gtcctcagcc tggcaagctg aggagcccct   1140
tcctgcagaa gcagctcacc caaccagaga cccactttgg cagagagcca gctgctgcca   1200
tctcaaggcc cagggcagat ctccctgctg aggagccggc gcccagcact cctccatgtc   1260
tggtgcaggc agaagaggag gctgtgtatg aggaacctcc agagcaggag accttctacg   1320
agcagccccc actggtgcag cagcaaggtg ctggctctga gcacattgac caccacattc   1380
agggccaggg gctcagtggg caagggctct gtgcccgtgc cctgtacgac taccaggcag   1440
ccgacgacac agagatctcc tttgacccg agaacctcat cacgggcatc gaggtgatcg    1500
acgaaggctg gtggcgtggc tatgggccgg atggccattt tggcatgttc cctgccaact   1560
acgtggagct cattgagtga ggctgagggc acatcttgcc cttcccctct cagacatggc   1620
ttccttattg ctggaagagg aggcctggga gttgacattc agcactcttc caggaatagg   1680
accccccagtg aggatgaggc ctcagggctc cctccggctt ggcagactca gcctgtcacc   1740
ccaaatgcag caatggcctg gtgattccca cacatccttc ctgcatcccc cgaccctccc   1800
agacagcttg gctcttgccc ctgacaggat actgagccaa gccctgcctg tggccaagcc   1860
ctgagtggcc actgccaagc tgcggggaag ggtcctgagc aggggcatct gggaggctct   1920
ggctgccttc tgcatttatt tgccttttt cttttctct tgcttctaag gggtggtggc     1980
caccactgtt tagaatgacc cttgggaaca gtgaacgtag agaattgttt ttagcagagt   2040
ttgtgaccaa agtcagagtg gatcatggtg gtttggcagc agggaatttg tcttgttgga   2100
gcctgctctg tgctccccac tccatttctc tgtccctctg cctgggctat gggaagtggg   2160
gatgcagatg gccaagctcc caccctgggt attcaaaaac ggcagacaca acatgttcct   2220
ccacgcggct cactcgatgc ctgcaggccc cagtgtgtgc ctcaactgat tctgacttca   2280
ggaaaagtaa aaaaaaaaaa aaaaaactcg agaagctttg gacttcttcg cca           2333
```

<210> SEQ ID NO 5
<211> LENGTH: 21
<212> TYPE: DNA
<213> ORGANISM: Homo sapiens

<400> SEQUENCE: 5
gcgccggccg ggcgcgaccc g                                          21

<210> SEQ ID NO 6
<211> LENGTH: 21
<212> TYPE: DNA
<213> ORGANISM: Homo sapiens

<400> SEQUENCE: 6
gcaatctcag cgcactgctg c                                          21

<210> SEQ ID NO 7
<211> LENGTH: 2843
<212> TYPE: DNA
<213> ORGANISM: Homo sapiens

<400> SEQUENCE: 7

```
ctttggagg ccgaggccgt aggatccctc gaggaatcgc ctaaccctgg ggaggttgag     60
gttgcagtga gtgagccata gttgtgtcac tgtgctccag tctgggcgaa agacagaatg   120
aggccctgcc acaggcaggc aggcaggcag gcaggcagaa agacaacagc tgtattatgt   180
tcttctcagg gtaggaagca aaataacag aatacagcac ttaattaatt tttttttttt    240
ccttcggacg gagtttcact cttggtgccc acgctggagt gcagtggcac catctcggct   300
caccgcaacc tccacctccc gcgttcaagc gattctcctg cctcagcctc ctgagtagct   360
gggattacag ggaggagcca ccacacccag ctgattttgt attgttagta gagacggcat   420
ttctccatgt gggtcaggct ggtctcgaac tggcgacccc agtggatctg cccgccccgg   480
cctcccaaag tgctggggtg acaggcgtga gccatcgtga ctggccggct acgtttattt   540
atttattttt ttaattattt tactttttt tagttttcca ttttaatcta tttatttat    600
tacatttatt tatttattta tttatttact tatttattta ttttcgagac agactctcgc   660
tctgctgccc aggctggagt gcagcggcgt gatctcggct cactgcaacg tccgcctccc   720
gggttcacgc cattctcctg cctcagcctc ccaagtagct gggactacag gcgcccgcca   780
ccgtgcccgg ctaacttttt gtattttgag tagagatggg gtttcactgt ggtagccagg   840
atggtctcga tctcctgacc ccgtgatccg tccacctcgg cctcccaaag tgctgggatg   900
acaggcgtga gccaccggcc ccggcctatt tatctattta ttaactttga gtccaggtta   960
tgaaaccagt tagttttgt aattttttt tttttttttt ttttttgaga cgaggtttca   1020
ccgtgttgcc aaggcttgga ccgagggatc caccggccct cggcctccca aaagtgcggg   1080
gatgacaggc gcgagcctac cgcgcccgga cccccctttt cccttcccc cgcttgtctt   1140
cccgacagac agtttcacgg cagagcgttt ggctggcgtg cttaaactca ttctaaatag   1200
aaatttggga cgtcagcttc tggcctcacg gactctgagc cgaggagtcc cctggtctgt   1260
ctatcacagg accgtacacg taaggaggag aaaaatcgta acgttcaaag tcagtcattt   1320
tgtgatacag aaatacacgg attcacccaa aacacagaaa ccagtctttt agaaatggcc   1380
ttagccctgg tgtccgtgcc agtgattctt ttcggtttgg accttgactg agaggattcc   1440
cagtcggtct ctcgtctctg gacggaagtt ccagatgatc cgatgggtgg gggacttagg   1500
```

```
ctgcgtcccc ccaggagccc tggtcgatta gttgtgggga tcgccttgga gggcgcggtg    1560
acccactgtg ctgtgggagc ctccatcctt ccccccaccc cctccccagg gggatcccaa    1620
ttcattccgg gctgacacgc tcactggcag gcgtcgggca tcacctagcg gtcactgtta    1680
ctctgaaaac ggaggcctca cagaggaagg gagcaccagg ccgcctgcgc acagcctggg    1740
gcaactgtgt cttctccacc gccccgccc ccacctccaa gttcctccct cccttgttgc     1800
ctaggaaatc gccactttga cgaccgggtc tgattgacct ttgatcaggc aaaaacgaac    1860
aaacagataa ataaataaaa taacacaaaa gtaactaact aaataaaata agtcaataca    1920
acccattaca atacaataag atacgatacg ataggatgcg ataggatacg ataggataca    1980
atacaatagg atacgataca atacaataca atacaataca atacaataca atacaataca    2040
atacaataca atacaatacg ccgggcgcgg tggctcatgc ctgtcatccc gtcactttgg    2100
gatgccgagg tggacgcatc acctgaagtc gggagttgga acaagcccg accaacatgg     2160 agaaatcccg tctcaattga aaatacaaaa ctagccgggc gcggtggcac atgcctataa    2220
tcccagctgc taggaaggct gaggcaggag aatcgcttga acctgggaag cggaggttgc    2280
agtgagccga gattgcgcca tcgcactcca gtctgagcaa caagagcgaa actccgtctc    2340
aaaaataaat acataaataa atacatacat acatacatac atacatacat acatacatac    2400
ataaattaaa ataaataaat aaaataaaat aaataaatgg ccctgcgcg gtggctcaag     2460 cctgtcatcc cctcactttg ggaggccaag gccggtggat caagaggcgg tcagaccaac    2520
agggccagta tggtgaaacc ccgtctctac tcacaataca caacattagc cgggcgctgt    2580
gctgtgctgt actgtctgta atcccagcta ctcgggaggc cgagctgagg caggagaatc    2640
gcttgaacct gggaggcgga ggttgcagtg agccgagatc gcgccactgc aacccagcct    2700
gggcgacaga gcgagactcc gtctccaaaa aatgaaaatg aaaatgaaac gcaacaaaat    2760
aattaaaaag tgagtttctg gggaaaaaga agaaaagaaa aagaaaaaa acaacaaaac      2820 agaacaaccc caccgtgaca tac                                             2843
```

<210> SEQ ID NO 8
<211> LENGTH: 1331
<212> TYPE: DNA
<213> ORGANISM: Homo sapiens

<400> SEQUENCE: 8

```
atggcggcga acctgagccg gaacgggcca gcgctgcaag aggcctacgt gcgggtggtc      60
accgagaagt ccccgaccga ctgggctctc tttacctatg aaggcaacag caatgacatc     120
cgcgtggctg gcacagggga gggtggcctg gaggagatgg tggaggagct caacagcggg    180
aaggtgatgt acgccttctg cagagtgaag gaccccaact ctggactgcc caaatttgtc    240
ctcatcaact ggacaggcga gggcgtgaac gatgtgcgga agggagcctg tgccagccac    300
gtcagcacca tggccagctt cctgaagggg gcccatgtga ccatcaacgc acgggccgag    360
gaggatgtgg agcctgagtg catcatggag aaggtggcca aggcttcagg tgccaactac    420
agctttcaca aggagagtgg ccgcttccag gacgtgggac cccaggcccc agtgggctct    480
gtgtaccaga agaccaatgc cgtgtctgag attaaagggg ttggtaaaga cagcttctgg    540
gccaaagcag agaaggagga ggagaaccgt cggctggaga aaagcgcg ggccgaggag      600 gcacagcggc agctggagca ggagcgccgg gagcgtgagc tgcgtgaggc tgcacgccgg    660
gagcagcgct atcaggagca gggtggcgag gccagccccc agaggacgtg ggagcagcag    720
caagaagtgg tttcaaggaa ccgaaatgag caggagtctg ccgtgcaccc gagggagatt    780
```

-continued

```
ttcaagcaga aggagagggc catgtccacc acctccatct ccagtcctca gcctggcaag    840
ctgaggagcc ccttcctgca gaagcagctc acccaaccag agacccactt tggcagagag    900
ccagctgctg ccatctcaag gcccagggca gatctccctg ctgaggagcc ggcgcccagc    960
actcctccat gtctggtgca ggcagaagag gaggctgtgt atgaggaacc tccagagcag   1020
gagaccttct acgagcagcc cccactggtg cagcagcaag gtgccggctc tgagcacatt   1080
gaccaccaca ttcagggcca ggggctcagt gggcaagggc tctgtgcccg tgccctgtac   1140
gactaccagg cagccgacga cacagagatc tcctttgacc ccgagaacct catcacgggc   1200
atcgaggtga tcgacgaagg ctggtggcgt ggctatgggc cggatggcca ttttggcatg   1260
ttccctgcca actacgtgga gctcattgag tgaggctgag ggcggccgct agactagtct   1320
agagaaaaaa c                                                        1331
```

```
<210> SEQ ID NO 9
<211> LENGTH: 793
<212> TYPE: PRT
<213> ORGANISM: Homo sapiens
<220> FEATURE:
<221> NAME/KEY: UNSURE
<222> LOCATION: (16)..(17)
<223> OTHER INFORMATION: Xaa is any amino acid or may be absent
<220> FEATURE:
<221> NAME/KEY: UNSURE
<222> LOCATION: (42)
<223> OTHER INFORMATION: Xaa is any amino acid or may be absent
<220> FEATURE:
<221> NAME/KEY: UNSURE
<222> LOCATION: (45)
<223> OTHER INFORMATION: Xaa is any amino acid or may be absent
<220> FEATURE:
<221> NAME/KEY: UNSURE
<222> LOCATION: (49)
<223> OTHER INFORMATION: Xaa is any amino acid or may be absent
<220> FEATURE:
<221> NAME/KEY: UNSURE
<222> LOCATION: (65)..(66)
<223> OTHER INFORMATION: Xaa is any amino acid or may be absent
<220> FEATURE:
<221> NAME/KEY: UNSURE
<222> LOCATION: (82)
<223> OTHER INFORMATION: Xaa is any amino acid or may be absent
<220> FEATURE:
<221> NAME/KEY: UNSURE
<222> LOCATION: (99)
<223> OTHER INFORMATION: Xaa is any amino acid or may be absent
<220> FEATURE:
<221> NAME/KEY: UNSURE
<222> LOCATION: (115)..(116)
<223> OTHER INFORMATION: Xaa is any amino acid or may be absent
<220> FEATURE:
<221> NAME/KEY: UNSURE
<222> LOCATION: (122)
<223> OTHER INFORMATION: Xaa is any amino acid or may be absent
<220> FEATURE:
<221> NAME/KEY: UNSURE
<222> LOCATION: (132)
<223> OTHER INFORMATION: Xaa is any amino acid or may be absent
<220> FEATURE:
<221> NAME/KEY: UNSURE
<222> LOCATION: (136)
<223> OTHER INFORMATION: Xaa is any amino acid or may be absent
<220> FEATURE:
<221> NAME/KEY: UNSURE
<222> LOCATION: (149)
<223> OTHER INFORMATION: Xaa is any amino acid or may be absent
<220> FEATURE:
<221> NAME/KEY: UNSURE
<222> LOCATION: (165)..(166)
<223> OTHER INFORMATION: Xaa is any amino acid or may be absent
<220> FEATURE:
```

-continued

```
<221> NAME/KEY: UNSURE
<222> LOCATION: (174)
<223> OTHER INFORMATION: Xaa is any amino acid or may be absent
<220> FEATURE:
<221> NAME/KEY: UNSURE
<222> LOCATION: (179)
<223> OTHER INFORMATION: Xaa is any amino acid or may be absent
<220> FEATURE:
<221> NAME/KEY: UNSURE
<222> LOCATION: (182)
<223> OTHER INFORMATION: Xaa is any amino acid or may be absent
<220> FEATURE:
<221> NAME/KEY: UNSURE
<222> LOCATION: (199)
<223> OTHER INFORMATION: Xaa is any amino acid or may be absent
<220> FEATURE:
<221> NAME/KEY: UNSURE
<222> LOCATION: (205)
<223> OTHER INFORMATION: Xaa is any amino acid or may be absent
<220> FEATURE:
<221> NAME/KEY: UNSURE
<222> LOCATION: (215)..(216)
<223> OTHER INFORMATION: Xaa is any amino acid or may be absent
<220> FEATURE:
<221> NAME/KEY: UNSURE
<222> LOCATION: (232)
<223> OTHER INFORMATION: Xaa is any amino acid or may be absent
<220> FEATURE:
<221> NAME/KEY: UNSURE
<222> LOCATION: (236)
<223> OTHER INFORMATION: Xaa is any amino acid or may be absent
<220> FEATURE:
<221> NAME/KEY: UNSURE
<222> LOCATION: (249)
<223> OTHER INFORMATION: Xaa is any amino acid or may be absent
<220> FEATURE:
<221> NAME/KEY: UNSURE
<222> LOCATION: (265)..(266)
<223> OTHER INFORMATION: Xaa is any amino acid or may be absent
<220> FEATURE:
<221> NAME/KEY: UNSURE
<222> LOCATION: (274)
<223> OTHER INFORMATION: Xaa is any amino acid or may be absent
<220> FEATURE:
<221> NAME/KEY: UNSURE
<222> LOCATION: (282)
<223> OTHER INFORMATION: Xaa is any amino acid or may be absent
<220> FEATURE:
<221> NAME/KEY: UNSURE
<222> LOCATION: (287)
<223> OTHER INFORMATION: Xaa is any amino acid or may be absent
<220> FEATURE:
<221> NAME/KEY: UNSURE
<222> LOCATION: (299)
<223> OTHER INFORMATION: Xaa is any amino acid or may be absent
<220> FEATURE:
<221> NAME/KEY: UNSURE
<222> LOCATION: (313)
<223> OTHER INFORMATION: Xaa is any amino acid or may be absent
<220> FEATURE:
<221> NAME/KEY: UNSURE
<222> LOCATION: (315)..(316)
<223> OTHER INFORMATION: Xaa is any amino acid or may be absent
<220> FEATURE:
<221> NAME/KEY: UNSURE
<222> LOCATION: (332)
<223> OTHER INFORMATION: Xaa is any amino acid or may be absent
<220> FEATURE:
<221> NAME/KEY: UNSURE
<222> LOCATION: (349)
<223> OTHER INFORMATION: Xaa is any amino acid or may be absent
<220> FEATURE:
<221> NAME/KEY: UNSURE
<222> LOCATION: (365)..(366)
<223> OTHER INFORMATION: Xaa is any amino acid or may be absent
<220> FEATURE:
<221> NAME/KEY: UNSURE
<222> LOCATION: (380)
<223> OTHER INFORMATION: Xaa is any amino acid or may be absent
```

```
<220> FEATURE:
<221> NAME/KEY: UNSURE
<222> LOCATION: (382)
<223> OTHER INFORMATION: Xaa is any amino acid or may be absent
<220> FEATURE:
<221> NAME/KEY: UNSURE
<222> LOCATION: (399)
<223> OTHER INFORMATION: Xaa is any amino acid or may be absent
<220> FEATURE:
<221> NAME/KEY: UNSURE
<222> LOCATION: (415)..(416)
<223> OTHER INFORMATION: Xaa is any amino acid or may be absent
<220> FEATURE:
<221> NAME/KEY: UNSURE
<222> LOCATION: (432)
<223> OTHER INFORMATION: Xaa is any amino acid or may be absent
<220> FEATURE:
<221> NAME/KEY: UNSURE
<222> LOCATION: (449)
<223> OTHER INFORMATION: Xaa is any amino acid or may be absent
<220> FEATURE:
<221> NAME/KEY: UNSURE
<222> LOCATION: (465)..(466)
<223> OTHER INFORMATION: Xaa is any amino acid or may be absent
<220> FEATURE:
<221> NAME/KEY: UNSURE
<222> LOCATION: (482)
<223> OTHER INFORMATION: Xaa is any amino acid or may be absent
<220> FEATURE:
<221> NAME/KEY: UNSURE
<222> LOCATION: (499)
<223> OTHER INFORMATION: Xaa is any amino acid or may be absent
<220> FEATURE:
<221> NAME/KEY: UNSURE
<222> LOCATION: (515)..(516)
<223> OTHER INFORMATION: Xaa is any amino acid or may be absent
<220> FEATURE:
<221> NAME/KEY: UNSURE
<222> LOCATION: (532)
<223> OTHER INFORMATION: Xaa is any amino acid or may be absent
<220> FEATURE:
<221> NAME/KEY: UNSURE
<222> LOCATION: (542)
<223> OTHER INFORMATION: Xaa is any amino acid or may be absent
<220> FEATURE:
<221> NAME/KEY: UNSURE
<222> LOCATION: (544)
<223> OTHER INFORMATION: Xaa is any amino acid or may be absent
<220> FEATURE:
<221> NAME/KEY: UNSURE
<222> LOCATION: (549)
<223> OTHER INFORMATION: Xaa is any amino acid or may be absent
<220> FEATURE:
<221> NAME/KEY: UNSURE
<222> LOCATION: (565)..(567)
<223> OTHER INFORMATION: Xaa is any amino acid or may be absent
<220> FEATURE:
<221> NAME/KEY: UNSURE
<222> LOCATION: (575)
<223> OTHER INFORMATION: Xaa is any amino acid or may be absent
<220> FEATURE:
<221> NAME/KEY: UNSURE
<222> LOCATION: (579)
<223> OTHER INFORMATION: Xaa is any amino acid or may be absent
<220> FEATURE:
<221> NAME/KEY: UNSURE
<222> LOCATION: (581)..(582)
<223> OTHER INFORMATION: Xaa is any amino acid or may be absent
<220> FEATURE:
<221> NAME/KEY: UNSURE
<222> LOCATION: (599)
<223> OTHER INFORMATION: Xaa is any amino acid or may be absent
<220> FEATURE:
<221> NAME/KEY: UNSURE
<222> LOCATION: (615)..(616)
<223> OTHER INFORMATION: Xaa is any amino acid or may be absent
<220> FEATURE:
<221> NAME/KEY: UNSURE
<222> LOCATION: (627)
```

```
<223> OTHER INFORMATION: Xaa is any amino acid or may be absent
<220> FEATURE:
<221> NAME/KEY: UNSURE
<222> LOCATION: (632)
<223> OTHER INFORMATION: Xaa is any amino acid or may be absent
<220> FEATURE:
<221> NAME/KEY: UNSURE
<222> LOCATION: (648)..(649)
<223> OTHER INFORMATION: Xaa is any amino acid or may be absent
<220> FEATURE:
<221> NAME/KEY: UNSURE
<222> LOCATION: (665)..(666)
<223> OTHER INFORMATION: Xaa is any amino acid or may be absent
<220> FEATURE:
<221> NAME/KEY: UNSURE
<222> LOCATION: (682)
<223> OTHER INFORMATION: Xaa is any amino acid or may be absent
<220> FEATURE:
<221> NAME/KEY: UNSURE
<222> LOCATION: (699)
<223> OTHER INFORMATION: Xaa is any amino acid or may be absent
<220> FEATURE:
<221> NAME/KEY: UNSURE
<222> LOCATION: (715)..(716)
<223> OTHER INFORMATION: Xaa is any amino acid or may be absent
<220> FEATURE:
<221> NAME/KEY: UNSURE
<222> LOCATION: (732)
<223> OTHER INFORMATION: Xaa is any amino acid or may be absent
<220> FEATURE:
<221> NAME/KEY: UNSURE
<222> LOCATION: (749)
<223> OTHER INFORMATION: Xaa is any amino acid or may be absent
<220> FEATURE:
<221> NAME/KEY: UNSURE
<222> LOCATION: (765)
<223> OTHER INFORMATION: Xaa is any amino acid or may be absent
<220> FEATURE:
<221> NAME/KEY: UNSURE
<222> LOCATION: (782)
<223> OTHER INFORMATION: Xaa is any amino acid or may be absent
<220> FEATURE:
<221> NAME/KEY: UNSURE
<222> LOCATION: (793)
<223> OTHER INFORMATION: Xaa is any amino acid or may be absent

<400> SEQUENCE: 9

His Glu Ile Pro Thr Val Pro Thr Tyr Tyr Pro Ala Lys Pro Gln Xaa
  1               5                  10                  15

Xaa Glu Arg Ala Trp Arg Asn Gln Arg Gly Lys Lys Thr Leu Leu Ser
             20                  25                  30

Thr Leu Val Trp His Gly Glu Glu Thr Xaa Glu Val Xaa Asn Lys Trp
         35                  40                  45

Xaa Ala Pro Gly Ala Pro Pro Val Ser Pro Arg Gly Ala Arg Gly Gly
     50                  55                  60

Xaa Xaa Arg Pro Cys Gly Pro Pro Val Lys Tyr His Tyr Ser Asp Arg
 65                  70                  75                  80

Phe Xaa Thr Asp Pro Val Arg Arg Gly Gly Glu Pro Arg Gly Ala Leu
                 85                  90                  95

Ala Ser Xaa Ala Lys Arg Pro Ala Ala Arg Arg Pro Gly Ala Thr Arg
            100                 105                 110

Ser Gly Xaa Xaa Ala Arg Trp Gly Val Xaa Leu Gly Arg Tyr Thr Cys
            115                 120                 125

Gln Thr Val Xaa Gln Val Ser Xaa Gly Glu Leu Arg Glu Asp Arg Asn
        130                 135                 140

Leu Pro Trp Ser Xaa Arg Ala Lys Ala Arg Leu Ile Leu Ile Phe Ser
145                 150                 155                 160

Thr Asn Thr Asp Xaa Xaa Ser Gly Ala Ser Arg Ser Phe Xaa Pro Phe
```

-continued

```
                  165                 170                 175
Gly Phe Xaa Ala Gly Xaa Val Arg Lys Val Thr Thr Gly Ile Thr Gly
            180                 185                 190
Leu Trp Arg Pro Ser Val Xaa Ser Asp Val Ala Phe Xaa Ser Phe Asp
        195                 200                 205
Val Gly Ser Ser Tyr His Xaa Xaa Ala Glu Phe Thr Lys Arg Trp Ile
    210                 215                 220
Val His Pro Leu Ile Gly Asn Xaa Ser Trp Asp Xaa Thr Val Val Arg
225                 230                 235                 240
Gln Val Ser Phe Thr Leu Leu Met Xaa Cys Cys Cys His Gly Asn Pro
            245                 250                 255
Ala Gln Tyr Glu Arg Asn Arg Xaa Xaa His Leu Val Tyr Val Leu
        260                 265                 270
Gly Xaa Gly Ala Asn Gly Ala Lys Leu Xaa Ser Val Gly Leu Xaa Leu
    275                 280                 285
Asn Ala Ser Lys Ser Glu Ser Arg Pro Gly Xaa Thr Ile Arg Gln Arg
290                 295                 300
Arg Gly Ala Ser Val Gly Leu Gly Xaa Pro Xaa Xaa Arg Leu Ser Pro
305                 310                 315                 320
Pro Ala Gly Arg Pro Pro Leu His Ala Pro Arg Xaa Arg Gly Arg Ala
            325                 330                 335
Arg Ala Pro Pro Arg Ala Gly Thr Gly Val Arg Cys Xaa Val Pro Phe
        340                 345                 350
Val Leu Gly Asn Gly Ala Arg Pro Glu Arg Arg Pro Xaa Xaa Arg Pro
    355                 360                 365
Ser Arg Thr Ala Arg Ser Trp Gly Thr Trp Arg Xaa Thr Xaa Ser Ile
370                 375                 380
Ser Ser Pro Gln Pro Gly Lys Leu Arg Ser Pro Phe Leu Gln Xaa Gln
385                 390                 395                 400
Leu Thr Gln Pro Glu Thr His Phe Gly Arg Glu Pro Ala Ala Xaa Xaa
            405                 410                 415
Ser Arg Pro Arg Ala Asp Leu Pro Ala Glu Glu Pro Ala Pro Ser Xaa
        420                 425                 430
Pro Pro Cys Leu Val Gln Ala Glu Glu Ala Val Tyr Glu Glu Pro
    435                 440                 445
Xaa Glu Gln Glu Thr Phe Tyr Glu Gln Pro Pro Leu Val Gln Gln Gln
450                 455                 460
Xaa Xaa Gly Ser Glu His Ile Asp His Ile Gln Gly Gln Gly Leu
465                 470                 475                 480
Ser Xaa Gln Gly Leu Cys Ala Arg Ala Leu Tyr Asp Tyr Gln Ala Ala
            485                 490                 495
Asp Asp Xaa Glu Ile Ser Phe Asp Pro Glu Asn Leu Ile Thr Gly Ile
        500                 505                 510
Glu Val Xaa Xaa Glu Gly Trp Trp Arg Gly Tyr Gly Pro Asp Gly His
    515                 520                 525
Phe Gly Met Xaa Pro Ala Asn Tyr Val Glu Leu Ile Glu Xaa Gly Xaa
530                 535                 540
Gly His Ile Leu Xaa Phe Pro Ser Gln Thr Trp Leu Pro Tyr Cys Trp
545                 550                 555                 560
Lys Arg Arg Pro Xaa Xaa Xaa His Ser Ala Leu Phe Gln Glu Xaa Asp
            565                 570                 575
Pro Gln Xaa Gly Xaa Xaa Leu Arg Ala Pro Ser Gly Leu Ala Asp Ser
        580                 585                 590
```

-continued

```
Ala Cys His Pro Lys Cys Xaa Asn Gly Leu Val Ile Pro Thr His Pro
            595                 600                 605

Ser Cys Ile Pro Arg Pro Xaa Xaa Thr Ala Trp Leu Leu Pro Leu Thr
        610                 615                 620

Gly Tyr Xaa Ala Lys Pro Cys Xaa Trp Pro Ser Pro Glu Trp Pro Leu
625                 630                 635                 640

Pro Ser Cys Gly Glu Gly Ser Xaa Xaa Gly Ala Ser Gly Arg Leu Trp
                645                 650                 655

Leu Pro Ser Ala Phe Ile Cys Leu Xaa Xaa Phe Ser Leu Ala Ser Lys
            660                 665                 670

Gly Trp Trp Pro Pro Leu Phe Arg Met Xaa Leu Gly Asn Ser Glu Arg
        675                 680                 685

Arg Glu Leu Phe Leu Ala Glu Phe Val Thr Xaa Val Arg Val Asp His
690                 695                 700

Gly Gly Leu Ala Ala Gly Asn Leu Ser Cys Xaa Xaa Leu Leu Cys Ala
705                 710                 715                 720

Pro His Ser Ile Ser Leu Ser Leu Cys Leu Gly Xaa Gly Lys Trp Gly
            725                 730                 735

Cys Arg Trp Pro Ser Ser His Pro Gly Tyr Ser Lys Xaa Ala Asp Thr
        740                 745                 750

Thr Cys Ser Ser Thr Arg Leu Thr Arg Cys Leu Gln Xaa Xaa Val Cys
        755                 760                 765

Ala Ser Thr Asp Ser Asp Phe Arg Lys Ser Lys Lys Xaa Lys Lys
770                 775                 780

Leu Glu Lys Leu Trp Thr Ser Ser Xaa
785                 790

<210> SEQ ID NO 10
<211> LENGTH: 784
<212> TYPE: PRT
<213> ORGANISM: Homo sapiens
<220> FEATURE:
<221> NAME/KEY: UNSURE
<222> LOCATION: (10)
<223> OTHER INFORMATION: Xaa is any amino acid or may be absent
<220> FEATURE:
<221> NAME/KEY: UNSURE
<222> LOCATION: (13)
<223> OTHER INFORMATION: Xaa is any amino acid or may be absent
<220> FEATURE:
<221> NAME/KEY: UNSURE
<222> LOCATION: (16)
<223> OTHER INFORMATION: Xaa is any amino acid or may be absent
<220> FEATURE:
<221> NAME/KEY: UNSURE
<222> LOCATION: (33)
<223> OTHER INFORMATION: Xaa is any amino acid or may be absent
<220> FEATURE:
<221> NAME/KEY: UNSURE
<222> LOCATION: (49)..(50)
<223> OTHER INFORMATION: Xaa is any amino acid or may be absent
<220> FEATURE:
<221> NAME/KEY: UNSURE
<222> LOCATION: (66)
<223> OTHER INFORMATION: Xaa is any amino acid or may be absent
<220> FEATURE:
<221> NAME/KEY: UNSURE
<222> LOCATION: (83)
<223> OTHER INFORMATION: Xaa is any amino acid or may be absent
<220> FEATURE:
<221> NAME/KEY: UNSURE
<222> LOCATION: (90)
<223> OTHER INFORMATION: Xaa is any amino acid or may be absent
<220> FEATURE:
<221> NAME/KEY: UNSURE
```

-continued

```
<222> LOCATION: (99)..(100)
<223> OTHER INFORMATION: Xaa is any amino acid or may be absent
<220> FEATURE:
<221> NAME/KEY: UNSURE
<222> LOCATION: (104)
<223> OTHER INFORMATION: Xaa is any amino acid or may be absent
<220> FEATURE:
<221> NAME/KEY: UNSURE
<222> LOCATION: (116)
<223> OTHER INFORMATION: Xaa is any amino acid or may be absent
<220> FEATURE:
<221> NAME/KEY: UNSURE
<222> LOCATION: (133)
<223> OTHER INFORMATION: Xaa is any amino acid or may be absent
<220> FEATURE:
<221> NAME/KEY: UNSURE
<222> LOCATION: (142)
<223> OTHER INFORMATION: Xaa is any amino acid or may be absent
<220> FEATURE:
<221> NAME/KEY: UNSURE
<222> LOCATION: (147)
<223> OTHER INFORMATION: Xaa is any amino acid or may be absent
<220> FEATURE:
<221> NAME/KEY: UNSURE
<222> LOCATION: (149)..(150)
<223> OTHER INFORMATION: Xaa is any amino acid or may be absent
<220> FEATURE:
<221> NAME/KEY: UNSURE
<222> LOCATION: (166)
<223> OTHER INFORMATION: Xaa is any amino acid or may be absent
<220> FEATURE:
<221> NAME/KEY: UNSURE
<222> LOCATION: (173)
<223> OTHER INFORMATION: Xaa is any amino acid or may be absent
<220> FEATURE:
<221> NAME/KEY: UNSURE
<222> LOCATION: (183)
<223> OTHER INFORMATION: Xaa is any amino acid or may be absent
<220> FEATURE:
<221> NAME/KEY: UNSURE
<222> LOCATION: (199)..(200)
<223> OTHER INFORMATION: Xaa is any amino acid or may be absent
<220> FEATURE:
<221> NAME/KEY: UNSURE
<222> LOCATION: (204)
<223> OTHER INFORMATION: Xaa is any amino acid or may be absent
<220> FEATURE:
<221> NAME/KEY: UNSURE
<222> LOCATION: (216)
<223> OTHER INFORMATION: Xaa is any amino acid or may be absent
<220> FEATURE:
<221> NAME/KEY: UNSURE
<222> LOCATION: (233)
<223> OTHER INFORMATION: Xaa is any amino acid or may be absent
<220> FEATURE:
<221> NAME/KEY: UNSURE
<222> LOCATION: (242)
<223> OTHER INFORMATION: Xaa is any amino acid or may be absent
<220> FEATURE:
<221> NAME/KEY: UNSURE
<222> LOCATION: (249)..(250)
<223> OTHER INFORMATION: Xaa is any amino acid or may be absent
<220> FEATURE:
<221> NAME/KEY: UNSURE
<222> LOCATION: (255)
<223> OTHER INFORMATION: Xaa is any amino acid or may be absent
<220> FEATURE:
<221> NAME/KEY: UNSURE
<222> LOCATION: (266)
<223> OTHER INFORMATION: Xaa is any amino acid or may be absent
<220> FEATURE:
<221> NAME/KEY: UNSURE
<222> LOCATION: (281)
<223> OTHER INFORMATION: Xaa is any amino acid or may be absent
<220> FEATURE:
<221> NAME/KEY: UNSURE
<222> LOCATION: (283)
<223> OTHER INFORMATION: Xaa is any amino acid or may be absent
<220> FEATURE:
```

-continued

```
<221> NAME/KEY: UNSURE
<222> LOCATION: (299)..(300)
<223> OTHER INFORMATION: Xaa is any amino acid or may be absent
<220> FEATURE:
<221> NAME/KEY: UNSURE
<222> LOCATION: (316)
<223> OTHER INFORMATION: Xaa is any amino acid or may be absent
<220> FEATURE:
<221> NAME/KEY: UNSURE
<222> LOCATION: (333)
<223> OTHER INFORMATION: Xaa is any amino acid or may be absent
<220> FEATURE:
<221> NAME/KEY: UNSURE
<222> LOCATION: (349)..(350)
<223> OTHER INFORMATION: Xaa is any amino acid or may be absent
<220> FEATURE:
<221> NAME/KEY: UNSURE
<222> LOCATION: (366)..(368)
<223> OTHER INFORMATION: Xaa is any amino acid or may be absent
<220> FEATURE:
<221> NAME/KEY: UNSURE
<222> LOCATION: (378)
<223> OTHER INFORMATION: Xaa is any amino acid or may be absent
<220> FEATURE:
<221> NAME/KEY: UNSURE
<222> LOCATION: (382)..(383)
<223> OTHER INFORMATION: Xaa is any amino acid or may be absent
<220> FEATURE:
<221> NAME/KEY: UNSURE
<222> LOCATION: (386)
<223> OTHER INFORMATION: Xaa is any amino acid or may be absent
<220> FEATURE:
<221> NAME/KEY: UNSURE
<222> LOCATION: (398)..(401)
<223> OTHER INFORMATION: Xaa is any amino acid or may be absent
<220> FEATURE:
<221> NAME/KEY: UNSURE
<222> LOCATION: (416)
<223> OTHER INFORMATION: Xaa is any amino acid or may be absent
<220> FEATURE:
<221> NAME/KEY: UNSURE
<222> LOCATION: (427)
<223> OTHER INFORMATION: Xaa is any amino acid or may be absent
<220> FEATURE:
<221> NAME/KEY: UNSURE
<222> LOCATION: (433)
<223> OTHER INFORMATION: Xaa is any amino acid or may be absent
<220> FEATURE:
<221> NAME/KEY: UNSURE
<222> LOCATION: (449)..(450)
<223> OTHER INFORMATION: Xaa is any amino acid or may be absent
<220> FEATURE:
<221> NAME/KEY: UNSURE
<222> LOCATION: (456)
<223> OTHER INFORMATION: Xaa is any amino acid or may be absent
<220> FEATURE:
<221> NAME/KEY: UNSURE
<222> LOCATION: (466)
<223> OTHER INFORMATION: Xaa is any amino acid or may be absent
<220> FEATURE:
<221> NAME/KEY: UNSURE
<222> LOCATION: (483)
<223> OTHER INFORMATION: Xaa is any amino acid or may be absent
<220> FEATURE:
<221> NAME/KEY: UNSURE
<222> LOCATION: (499)..(500)
<223> OTHER INFORMATION: Xaa is any amino acid or may be absent
<220> FEATURE:
<221> NAME/KEY: UNSURE
<222> LOCATION: (507)
<223> OTHER INFORMATION: Xaa is any amino acid or may be absent
<220> FEATURE:
<221> NAME/KEY: UNSURE
<222> LOCATION: (515)..(518)
<223> OTHER INFORMATION: Xaa is any amino acid or may be absent
<220> FEATURE:
<221> NAME/KEY: UNSURE
<222> LOCATION: (527)
<223> OTHER INFORMATION: Xaa is any amino acid or may be absent
```

-continued

```
<220> FEATURE:
<221> NAME/KEY: UNSURE
<222> LOCATION: (533)..(534)
<223> OTHER INFORMATION: Xaa is any amino acid or may be absent
<220> FEATURE:
<221> NAME/KEY: UNSURE
<222> LOCATION: (543)
<223> OTHER INFORMATION: Xaa is any amino acid or may be absent
<220> FEATURE:
<221> NAME/KEY: UNSURE
<222> LOCATION: (549)..(550)
<223> OTHER INFORMATION: Xaa is any amino acid or may be absent
<220> FEATURE:
<221> NAME/KEY: UNSURE
<222> LOCATION: (566)
<223> OTHER INFORMATION: Xaa is any amino acid or may be absent
<220> FEATURE:
<221> NAME/KEY: UNSURE
<222> LOCATION: (573)
<223> OTHER INFORMATION: Xaa is any amino acid or may be absent
<220> FEATURE:
<221> NAME/KEY: UNSURE
<222> LOCATION: (577)
<223> OTHER INFORMATION: Xaa is any amino acid or may be absent
<220> FEATURE:
<221> NAME/KEY: UNSURE
<222> LOCATION: (583)
<223> OTHER INFORMATION: Xaa is any amino acid or may be absent
<220> FEATURE:
<221> NAME/KEY: UNSURE
<222> LOCATION: (597)
<223> OTHER INFORMATION: Xaa is any amino acid or may be absent
<220> FEATURE:
<221> NAME/KEY: UNSURE
<222> LOCATION: (599)..(600)
<223> OTHER INFORMATION: Xaa is any amino acid or may be absent
<220> FEATURE:
<221> NAME/KEY: UNSURE
<222> LOCATION: (613)
<223> OTHER INFORMATION: Xaa is any amino acid or may be absent
<220> FEATURE:
<221> NAME/KEY: UNSURE
<222> LOCATION: (615)..(616)
<223> OTHER INFORMATION: Xaa is any amino acid or may be absent
<220> FEATURE:
<221> NAME/KEY: UNSURE
<222> LOCATION: (633)
<223> OTHER INFORMATION: Xaa is any amino acid or may be absent
<220> FEATURE:
<221> NAME/KEY: UNSURE
<222> LOCATION: (649)..(650)
<223> OTHER INFORMATION: Xaa is any amino acid or may be absent
<220> FEATURE:
<221> NAME/KEY: UNSURE
<222> LOCATION: (666)
<223> OTHER INFORMATION: Xaa is any amino acid or may be absent
<220> FEATURE:
<221> NAME/KEY: UNSURE
<222> LOCATION: (679)
<223> OTHER INFORMATION: Xaa is any amino acid or may be absent
<220> FEATURE:
<221> NAME/KEY: UNSURE
<222> LOCATION: (683)..(684)
<223> OTHER INFORMATION: Xaa is any amino acid or may be absent
<220> FEATURE:
<221> NAME/KEY: UNSURE
<222> LOCATION: (689)..(690)
<223> OTHER INFORMATION: Xaa is any amino acid or may be absent
<220> FEATURE:
<221> NAME/KEY: UNSURE
<222> LOCATION: (699)..(700)
<223> OTHER INFORMATION: Xaa is any amino acid or may be absent
<220> FEATURE:
<221> NAME/KEY: UNSURE
<222> LOCATION: (716)
<223> OTHER INFORMATION: Xaa is any amino acid or may be absent
<220> FEATURE:
<221> NAME/KEY: UNSURE
<222> LOCATION: (731)
```

```
<223> OTHER INFORMATION: Xaa is any amino acid or may be absent
<220> FEATURE:
<221> NAME/KEY: UNSURE
<222> LOCATION: (733)
<223> OTHER INFORMATION: Xaa is any amino acid or may be absent
<220> FEATURE:
<221> NAME/KEY: UNSURE
<222> LOCATION: (747)
<223> OTHER INFORMATION: Xaa is any amino acid or may be absent
<220> FEATURE:
<221> NAME/KEY: UNSURE
<222> LOCATION: (749)..(750)
<223> OTHER INFORMATION: Xaa is any amino acid or may be absent
<220> FEATURE:
<221> NAME/KEY: UNSURE
<222> LOCATION: (753)
<223> OTHER INFORMATION: Xaa is any amino acid or may be absent
<220> FEATURE:
<221> NAME/KEY: UNSURE
<222> LOCATION: (764)
<223> OTHER INFORMATION: Xaa is any amino acid or may be absent
<220> FEATURE:
<221> NAME/KEY: UNSURE
<222> LOCATION: (766)
<223> OTHER INFORMATION: Xaa is any amino acid or may be absent
<220> FEATURE:
<221> NAME/KEY: UNSURE
<222> LOCATION: (774)
<223> OTHER INFORMATION: Xaa is any amino acid or may be absent
<220> FEATURE:
<221> NAME/KEY: UNSURE
<222> LOCATION: (783)
<223> OTHER INFORMATION: Xaa is any amino acid or may be absent

<400> SEQUENCE: 10

Ile Arg His Glu His Gly Glu Glu Thr Xaa Glu Val Xaa Asn Lys Xaa
  1               5                  10                  15

Glu Ala Pro Gly Ala Pro Pro Val Ser Pro Arg Gly Ala Arg Gly Gly
             20                  25                  30

Xaa Arg Arg Pro Cys Gly Pro Pro Val Lys Tyr His Tyr Ser Asp Arg
         35                  40                  45

Xaa Xaa Thr Asp Pro Val Arg Arg Gly Gly Glu Pro Arg Gly Ala Leu
     50                  55                  60

Ala Xaa Gly Ala Lys Arg Pro Ala Ala Arg Arg Pro Gly Ala Thr Arg
 65                  70                  75                  80

Ser Gly Xaa Ser Ala Arg Trp Gly Val Xaa Leu Gly Arg Tyr Thr Cys
             85                  90                  95

Gln Thr Xaa Xaa Gln Val Ser Xaa Gly Glu Leu Arg Glu Asp Arg Asn
            100                 105                 110

Leu Pro Trp Xaa Arg Arg Ala Lys Ala Arg Leu Ile Leu Ile Phe Ser
            115                 120                 125

Thr Asn Thr Asp Xaa Glu Ser Gly Ala Ser Arg Ser Phe Xaa Pro Phe
        130                 135                 140

Gly Phe Xaa Ala Xaa Xaa Val Arg Lys Val Thr Thr Gly Ile Thr Gly
145                 150                 155                 160

Leu Trp Arg Pro Ser Xaa His Ser Asp Val Ala Phe Xaa Ser Phe Asp
                165                 170                 175

Val Gly Ser Ser Tyr His Xaa Glu Ala Glu Phe Thr Lys Arg Trp Ile
            180                 185                 190

Val His Pro Leu Ile Gly Xaa Xaa Ser Trp Val Xaa Thr Val Val Arg
            195                 200                 205

Gln Val Ser Phe Thr Leu Leu Xaa Met Cys Cys Cys His Gly Asn Pro
        210                 215                 220

Ala Gln Tyr Glu Arg Asn Arg Arg Xaa Arg His Leu Val Tyr Val Leu
```

-continued

```
            225                 230                 235                 240
Gly Xaa Gly Ala Asn Gly Ala Lys Xaa Xaa Ser Val Gly Leu Xaa Leu
                245                 250                 255
Asn Ala Ser Lys Ser Glu Ser Arg Pro Xaa Gly Thr Ile Arg Gln Arg
            260                 265                 270
Arg Gly Ala Ser Val Gly Leu Gly Xaa Pro Xaa Pro Arg Leu Ser Pro
        275                 280                 285
Pro Ala Gly Arg Pro Pro Ser Thr Arg Xaa Xaa Arg Ala Gly Gly
    290                 295                 300
Arg Val Pro Arg Ala Pro Gly Pro Gly Ser Xaa Ala Glu Cys Pro
305                 310                 315                 320
Ser Ser Trp Glu Thr Gly Arg Gly Arg Lys Gly Gly Xaa Pro Leu Ala
                325                 330                 335
Arg His Ala Pro His Val Arg Ala Arg Ala Glu Phe Xaa Xaa Ser Ser
            340                 345                 350
Thr Ile His Asn Arg His Thr Ser Ala Cys Ile Phe Met Xaa Xaa Xaa
        355                 360                 365
Ile Leu Phe Leu Trp Val Asp Ile Gln Xaa Trp Asp Cys Xaa Xaa Thr
370                 375                 380
Trp Xaa Phe Tyr Phe Trp Phe Ile Glu Lys Ser Ser Tyr Xaa Xaa Xaa
385                 390                 395                 400
Xaa Arg Leu Tyr Lys Phe Thr Ser Leu Pro Ser Asp Phe Phe Lys Xaa
        405                 410                 415
Glu Arg Met Val Trp Arg Asn Ala Pro His Xaa Tyr Pro Pro Phe Thr
            420                 425                 430
Xaa Leu Leu Gln Asn Asp Phe Lys Gly Tyr Arg Tyr Leu Gln Val Ser
        435                 440                 445
Xaa Xaa Arg Gln Ile Glu Tyr Xaa Asn Phe Cys Ile Arg Gly Thr Asp
    450                 455                 460
Phe Xaa Ile Gln Ser Cys Met Asn Lys Asp Lys Cys Ser Arg Asp Leu
465                 470                 475                 480
Gln Ser Xaa Asn Trp Lys Ser Gln Met Lys Tyr Ile Ser Ser Ser Thr
            485                 490                 495
Thr Ser Xaa Xaa Ser Thr Glu Leu Ala Leu Xaa Ser Ser Leu Ile Pro
        500                 505                 510
Thr Tyr Xaa Xaa Xaa Xaa Lys Gly Phe Ile Ser Asn Ile Leu Xaa Gly
        515                 520                 525
Ile Lys Ile Lys Xaa Xaa Val Lys Leu Phe Ser Leu Ala Phe Xaa Phe
    530                 535                 540
Gln Asn Ile Lys Xaa Xaa Pro Ser Ile Gly His Leu Tyr Cys Thr Arg
545                 550                 555                 560
His Cys Val Cys His Xaa Ser Lys Met Phe Ser Trp Xaa Cys Ser Gln
                565                 570                 575
Xaa Phe Cys Arg Val Arg Xaa Ser Leu Thr Val Val Arg Leu Phe Ser
        580                 585                 590
Lys Arg Asn Leu Xaa Thr Xaa Xaa Phe Asn Leu Arg Lys Val Ser Asn
        595                 600                 605
Arg Thr Arg Thr Xaa Thr Xaa Xaa Ile Thr Leu Gln Ile Ser Pro Tyr
            610                 615                 620
His Thr Ala Ser Thr Cys Ala Cys Xaa Leu Ile Pro Gly Ser Cys Tyr
625                 630                 635                 640
Phe Pro Phe Tyr Phe Leu Ser Leu Xaa Xaa Thr Thr Pro Phe Ser Pro
                645                 650                 655
```

-continued

```
His Phe Phe Ser Phe Phe Leu Ile Val Xaa Tyr Ile Thr Asn Thr Cys
            660                 665                 670

Leu Ser Glu Gln Leu Ile Xaa His Lys Arg Xaa Xaa Ser Thr Gly Glu
        675                 680                 685

Xaa Xaa Leu Ile Pro Val Ile Leu Ala Leu Xaa Xaa Ala Lys Ala Gly
    690                 695                 700

Arg Ser Leu Glu Ser Arg Val Arg Asp Gln Pro Xaa Gln His Gly Glu
705                 710                 715                 720

Thr Leu Ser Leu Gln Lys Asn Thr Lys Ile Xaa Pro Xaa Val Leu Ala
                725                 730                 735

His Thr Cys Ser Leu Ser Tyr Ser Glu Gly Xaa Gly Xaa Xaa Ile Asp
            740                 745                 750

Xaa Ala Gln Glu Val Glu Ala Ala Val Arg Xaa Asp Xaa Ala Ile
        755                 760                 765

Ala Leu Gln Pro Gly Xaa Glu Arg Glu Thr Leu Ser Gln Lys Xaa Lys
    770                 775                 780
```